United States Patent [19]

Okano et al.

[11] Patent Number: 5,438,045

[45] Date of Patent: Aug. 1, 1995

[54] 1,4-DIAZEPINE DERIVATIVE AND ITS PHARMACEUTICAL USE

[75] Inventors: Kazuo Okano; Shuhei Miyazawa; Richard S. J. Clark; Shinya Abe; Tetsuya Kawahara; Naoyuki Shimomura; Osamu Asano; Hiroyuki Yoshimura; Mitsuaki Miyamoto; Yoshimori Sakuma; Kenzo Muramoto; Hiroshi Obaishi; Koukichi Harada; Hajime Tsunoda; Satoshi Katayama; Kouji Yamada; Shigeru Souda; Yoshimasa Machida; Kouichi Katayama; Isao Yamatsu, all of Ibaraki, Japan

[73] Assignee: Eisai Co., Ltd., Tokyo, Japan

[21] Appl. No.: 52,721

[22] Filed: Apr. 27, 1993

Related U.S. Application Data

[60] Division of Ser. No. 778,563, Oct. 17, 1991, Pat. No. 5,221,671, which is a division of Ser. No. 751,632, Aug. 26, 1991, which is a continuation of Ser. No. 506,928, Apr. 10, 1990, abandoned, which is a continuation-in-part of Ser. No. 421,929, Oct. 16, 1989, abandoned.

[30] Foreign Application Priority Data

| Oct. 31, 1988 | [JP] | Japan | 63-275460 |
| Nov. 24, 1988 | [JP] | Japan | 63-297068 |
| Dec. 16, 1988 | [JP] | Japan | 63-318016 |
| Dec. 28, 1988 | [JP] | Japan | 63-331622 |

[51] Int. Cl.⁶ .................. A61K 31/55; C07D 495/22
[52] U.S. Cl. .................. 514/81; 514/219; 540/542; 540/555
[58] Field of Search ............ 540/555, 542; 514/219, 514/81

[56] References Cited

U.S. PATENT DOCUMENTS

| 4,959,361 | 9/1990 | Walser | 514/220 |
| 4,960,770 | 10/1990 | Moriwaki et al. | 514/219 |
| 4,968,794 | 11/1990 | Weber et al. | 540/560 |
| 5,049,559 | 9/1991 | Braquet et al. | 514/219 |
| 5,049,560 | 9/1991 | Esanu et al. | 514/219 |

FOREIGN PATENT DOCUMENTS 254245  1/1988  European Pat. Off. .
2229723 10/1990 United Kingdom .

OTHER PUBLICATIONS

Tsunoda et al, Chemical Abstract, vol. 114, No. 55582u (1990).

*Primary Examiner*—Mukund J. Shah
*Assistant Examiner*—Philip I. Datlow
*Attorney, Agent, or Firm*—Birch, Stewart, Kolasch & Birch

[57] ABSTRACT

A triazolo-1,4-di-azepine compound of the below given formula and a pharmacologically acceptable salt thereof are disclosed and useful in the pharmaceutical field, especially to allergic diseases.

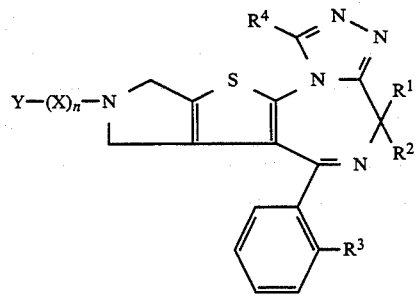

in which R1 and R2 are hydrogen or an alkyl, R3 is hydrogen or a halogen, R4 is hydrogen or an alkyl, X is —OOO—, —NHCO—, —CO— or others and Y is a cycloalkyl, a cycloalkylalkyl, an alkynyl or others.

12 Claims, No Drawings

1,4-DIAZEPINE DERIVATIVE AND ITS PHARMACEUTICAL USE

This application is a divisional of application Ser. No. 07/778,563, filed on Oct. 17, 1991, now U.S. Pat. No. 5,221,671, which is a divisional application under 37 CFR 1.60 of Ser. No. 07/751,632 filed on Aug. 26, 1991, still pending which is a continuation application under 37 CFR 1.62 of Ser. No. 07/506,928 filed on Apr. 10, 1990, now abandoned, which is a CIP of Ser. No. 07/421,929 filed on Oct. 16, 1989, now abandoned for 1,4-Diazephine Derivative and its Pharmaceutical Use, the entire contents of which are hereby incorporated by reference.

The invention provides a new 1,4-diazepine derivative and a pharmacologically acceptable salt thereof, a process for preparing it and the pharmaceutical use. The compound and the salt have an excellent medical activity.

PRIOR ARTS

In recent years, a platelet activating factor (hereinafter referred to simply as PAF) has attracted much attention and its relationship with various diseases is now being clarified. Now, it has been assumed that PAF takes part in not only inflammation, but also DIC, endotoxin shock, asthma, ulcers in alimentary canal, hepatisis and the rejection at the time of organ transplantation. In addition, attention has been drawn to as a mediator which is one of allergic reactions.

Under these circumstances, there have been made investigations on compounds having the anti-PAF activity. Among these compounds, a 1,4-diazepine compound having the anti-PAF action has been proposed, for example, in Japanese Laid-open Patent Application No. 63-33382. However, a satisfactory anti-PAF agent which is adapted, particularly, for allergies such as asthma has not been developed yet.

Accordingly, we have continued investigations and studies over a long term with respect to 1,4-diazepine derivatives which have not only an excellent PAF-inhibiting activity, but also a long activity.

SUMMARY OF THE INVENTION

We made intensive studies over a long term in order to attain the above object and, as a result, found that the purpose could be achieved by 1,4-diazephine derivatives defined below or pharmacologically acceptable salts thereof. The present invention has been accomplished based on the above finding.

The invention provides a triazolo-1,4-di-azepine compound of the below given formula and a pharmacologically acceptable salt thereof.

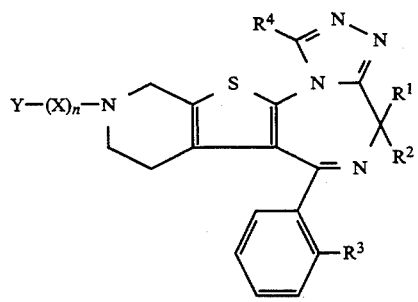

wherein $R^1$ and $R^2$ are the same or different and represent a hydrogen atom or a lower alkyl group, $R^3$ represents a hydrogen atom or a halogen atom, $R^4$ represents a hydrogen atom or a lower alkyl group, X represents (a) a group of the formula,

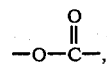

(b) a group of the formula,

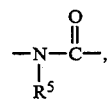

wherein $R^5$ represents a hydrogen atom or a lower alkyl group, (c) a group of the formula,

(d) a group of the formula,

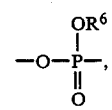

(wherein $R^6$ represents a lower alkyl group.

(e) a group of the formula,

n is an integer of 0 or 1.
and Y represents (1) a cycloalkyl group which may have a substituent(s),
(2) a cycloalkylalkyl,
(3) an alkynyl group,
(4) a group of the formula

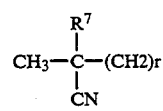

in which R7 is hydrogen or methyl and r is zero, 1 or 2, (5) a group of the formula, $NC-(CH_2)_p-$, wherein p is an integer of from 1 to 6, (6) a group of the formula, $A-(CH_2)_q-$ wherein A represents a group selected from a pyridyl group, a pyranyl group and a morpholino group and q is an integer of from 0 to 6, (7) an alkynyl group having from 1 to 6 carbon atoms wherein a phenyl group or a cycloalkyl group is joined to any carbon atom.

(8) a group of the formula,

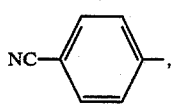

(9) a group of the formula,

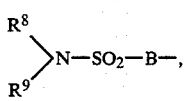

wherein R⁸ and
R⁹ are the same or different and represent a hydrogen atom n lower alkyl group, a pyridylmethyl group or a cycloalkyl group or R⁸ and R⁹ may be joined along with a nitrogen atom to form a ring, and B represents a phenylene group or a lower alkylene group having from 1 to 3 carbon atoms,

(10) a group of the formula,

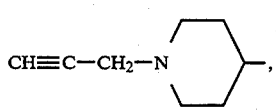

(11) a group of the formula,

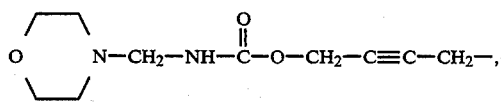

(12) a group of the formula,

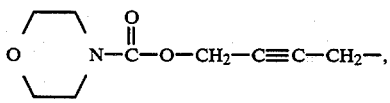

(13) a group of the formula,

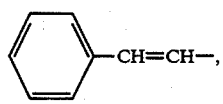

(14) a group of the formula,

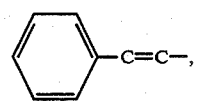

(15) a lower alkyl group, or
(16) a cycloalkylalkenyl group,
(17)

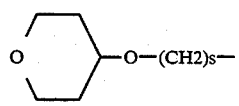

in which s is 1 or 2, (18)

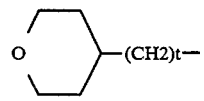

in which t is 1 or 2, (19)

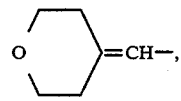

(20) an arylalkyl,
(21) an arylalkenyl,
(22)

in which $R^{10}$ is hydrogen or phenyl, $R^{11}$ is hydrogen or a lower alkyl, E is an alkenylene and u is zero or 1, or (23)

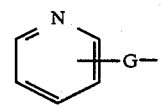

in which G is an alkenylene or —J—(CH2)k—, J is oxygen or sulfur, k is zero, 1 or 2, provided that when X is (a) $-O-\overset{O}{\underset{\|}{C}}-$, (b) $-\underset{\underset{R^5}{|}}{N}-\overset{O}{\underset{\|}{C}}-$, (c) $-\overset{O}{\underset{\|}{C}}-$, or (e) $-\overset{O}{\underset{\underset{\|}{O}}{\overset{\|}{S}}}-$, Y is a group selected from (1) to (14) and (16) to (23) and when X is (d) $-O-\overset{OR^6}{\underset{\underset{O}{\|}}{P}}-,$ Y is a group of (15) and that when n=O, Y is an alkynyl group of (3).

In the formula of the invention it is preferable that X is (a), (b) or (c). It is more preferable that X is (c) —CO—.

It is preferable that n is 1 when X is (a), (b) or (c).

It is prefeable that Y is one of (1) to (16), more preferably (4), (3), (16) and (2). Most preferable examples for Y include a cycloalkyl, in particular one having 3 to 7 carbon atoms, such as cyclopropyl and HC≡C—C(CH3)2—.

It is preferable that R1 is hydrogen and R2 is methyl. Preferable compounds have the formula in which R3 is chlorine, R1 is hydrogen, R4 is methyl, n is 1, and Y—X— and R2 are defined with one of the following combinations:

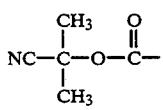 H

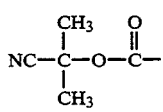 CH3

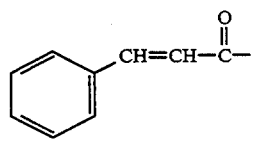 H

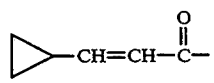 H

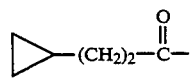 H

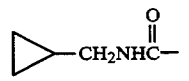 H

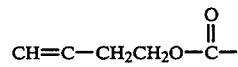 CH3

 CH3

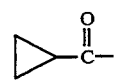 H

 H

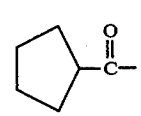 H

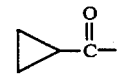 CH3

The invention provides another compound, a triazolo-1,4-di-azepine compound of the below given formula and a pharmacologically acceptable salt thereof in which Y, X, n, R1, R2, R3, R4 are defined in the same manner as shown above:

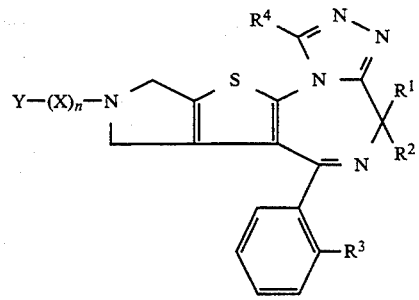

A third compound of the invention is a triazolo-1,4-di-azepine compound of the below given formula and a pharmacologically acceptable salt thereof in which Y, X, n, R1, R2, R3, R4 are defined in the same manner as shown above:

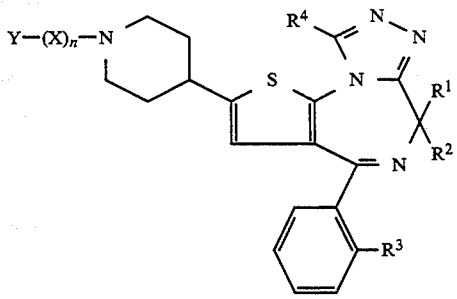

The invention provides the pharmacological use of the compound as defined above and its salt. In the invention a pharmaceutical composition comprises a pharmacologically effective amount of the compound of the salt thereof, defined above, and a pharmacologically acceptable carrier. A method for treating a disease against which anti-PAF activity is effective, which comprises administering a pharmacologically effective amount of the compound or the salt thereof as defined above. The disease is an allergic disease such as asthma.

The 1,4-diazepine derivatives of the general formula (I) have good PAF-inhibiting efficacy and good persistency with high safety.

Accordingly, an object of the invention is to provide novel 1,4-diazepine derivatives or pharmacologically acceptable salts thereof which have good anti-PAF action. Another object of the invention is to provide a process for preparing the same. A further object of the invention is to provide an agent comprising the same.

In the compounds (I) of the invention, the lower alkyl group for R1, R2, R4, R5, R8, R9 and R11 is a linear or branched alkyl group having from 1 to 6 carbon atoms and includes, for example, a methyl group, an ethyl group, a propyl group, an isopropyl group, a butyl group, an isobutyl group, a sec-butyl group, a tert-butyl group, a pentyl group (amyl group), an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethybutyl group, a 1,1,2-trimethylpropyl group, a 1,2,2-trimethylpropyl group, a 1-ethyl-1-methylpropyl group, a 1-ethyl-2-methylpropyl group or the like. Of these, preferable groups include a methyl group, an ethyl group, a propyl group and an isopropyl group, of which the methyl group is most preferred.

The cycloalkyl group defined by Y is a cycloalkyl group having from 3 to 7 carbon atoms such as, for example, cyclopropyl, cyclobutyl, cyclopentyl, cyclohexyl or cycloheptyl. Of these, cyclopropyl, cyclobutyl and cyclopentyl are most preferred. The cycloalkyl may have a substituent such as methyl.

The cycloalkylalkyl group is a group which is derived from the above-indicated cycloalkyl group. Typical examples include cyclopentylmethyl, cyclopropylmethyl, cyclohexylmethyl, and cyclohexylethyl groups.

The cycloalkylalkenyl group is a group which is derived from the above-indicated cycloalkylalkyl group. Typical and preferable groups include, for example, those of the following formulae

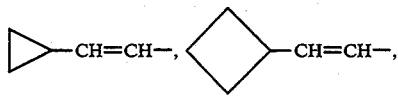

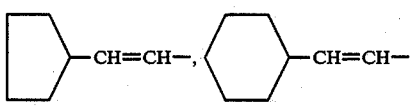

The alkynyl group is a group which has from 1 to 6 carbon atoms and a triple bond at any portion thereof. Typical alkynyl groups include, for example, CH≡C—CH$_2$—, CH≡C—CH$_2$—CH$_2$—, CH≡C—CH$_2$—CH$_2$—CH$_2$—, CH≡C—CH$_2$—CH$_2$—CH$_2$—CH$_2$—,

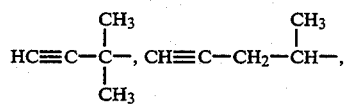

CH$_3$—C≡C—CH$_2$—CH$_2$—, and CH$_3$—CH≡C—CH$_2$—. Of these, CH≡C—C$_2$—, CH≡C—CH$_2$—CH$_2$—, CH≡C—CH$_2$—CH$_2$—CH$_2$— and CH≡C—CH$_2$—CH$_2$—CH$_2$—CH$_2$— are most preferred.

In the formula (4),

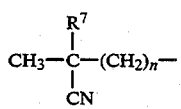

for Y, $R^7$ is most preferably a methyl group.

In the formula (5), p is from 1 to 6 m preferably from 1 to 4.

In the formula (6), q is from 0 to 6.

In the formula (7), an alkynyl group having from 1 to 6 carbon atoms wherein a phenyl group or a cycloalkyl group is joined to any carbon atom of the group includes, for example, those groups of the following formulae

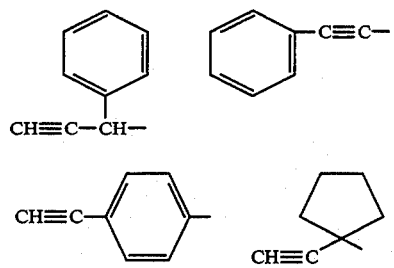

In (9), $R^8$ and $R^9$ may form a ring along with a nitrogen atom. Specific examples of the ring are shown below.

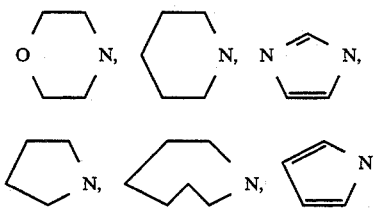

As described before, when X represents a group of the formula,

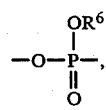

Y is a lower alkyl group, preferably a methyl or ethyl group.

The arylalkyl preferably includes benzyl, phenethyl, a benzyl having on the phenyl a substituent such as an alkyl, such as methyl and a halogen such as chlorine, bromine and fluorine. The arylalkenyl preferably includes the following two:

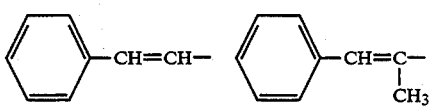

The group (22) for Y preferably includes the following three:

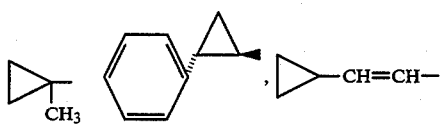

The group (23) for Y preferably includes the following two:

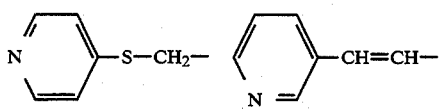

In the practice of the invention, the most preferably group represented by X is a group of the formula (a)

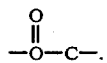

A more preferably group is of the formula (b),

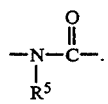

Preferably, groups of the formula (c),

or the formula (d),

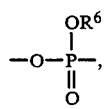

are used. When n=O, good results are obtained.

In the present invention, a first preferably group of compounds are those of the following chemical, structural formula

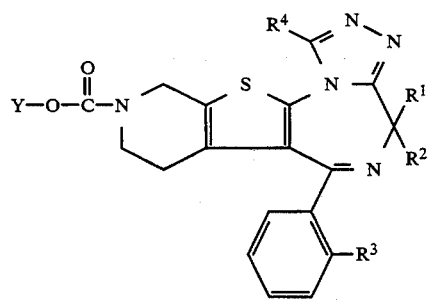

wherein $R^1$, $R^2$, $R^3$, $R^4$ and Y have, respectively, the same meanings as defined before where the most preferable group represented by U is a group of the formula,

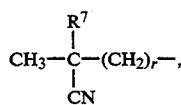

in which $R^7$ is hydrogen or methyl, r is zero, 1 or 2, a group of the formula, $NC-(CH_2)_p-$ wherein p is an integer of from 1 to 6, or an alkynyl group. Most preferably, $R^3$ is a halogen atom such as a chlorine atom and $R^4$ is a methyl group.

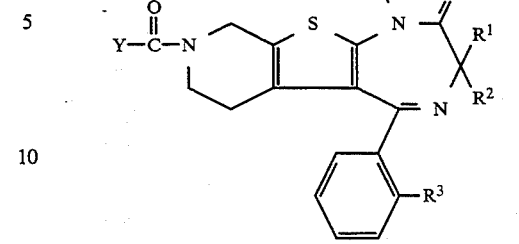

wherein $R^1$, $R^2$, $R^3$, $R^4$ and Y have, respectively, the same meanings as defined before where the most preferable group for Y is a cycloalkyl such as cyclopropyl, an alkynyl, a cycloalkylalkyl group, a cycloalkylalkenyl group, a group of the formula,

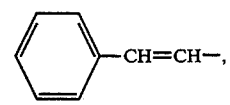

or a group represented by the formula, $NC-(CH_2)_p-$ wherein p is an integer of from 1 to 6.

In the compound (B), it is preferable that Y is cyclopropyl, R4 is methyl, R1 is methyl, R2 is hydrogen and R3 is chlorine.

A second preferable group of compounds are those of the chemical, structural formula (C)

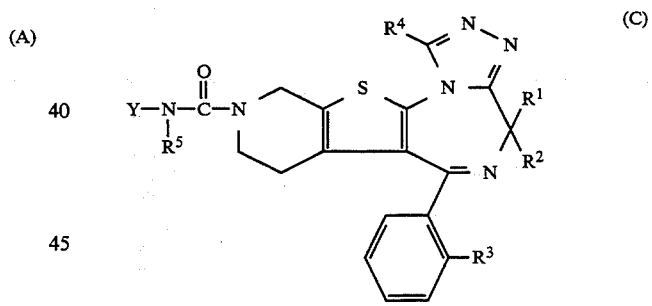

wherein $R^1$, $R^2$, $R^3$, $R^4$, $R^5$ and Y have, respectively, the same meanings as defined before where the most preferable group represented by Y is a group of the formula,

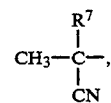

wherein $R^7$ represents a hydrogen atom or a methyl group, a group of the formula, $NC-(CH_2)_p-$ wherein p is an integer of from 1 to 6, or alkynyl group.

Taking notice of $R^1$ and $R^2$ in the compounds are those of the the invention, it is most preferable that $R^1$ is a hydrogen atom and $R^2$ is a lower alkyl group, particularly a methyl group. This is more particularly shown by the following general formula

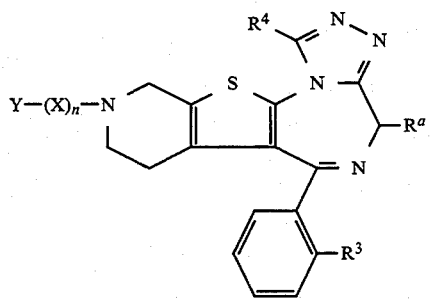 (D)

wherein R² represents a lower alkyl group, R³ represents a hydrogen atom or a halogen atom, R⁴ represents a hydrogen atom or a lower alkyl group, X represents (a) a group of the formula,

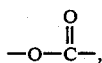

(b) a group of the formula,

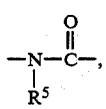

wherein R⁵ represents a hydrogen atom or a lower alkyl group, (c) a group of the formula,

or (d) a group of the formula,

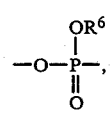

wherein R⁵ represents a lower alkyl group,

Y represents
(1) a cycloalkyl group
(2) a cycloalkylalkyl group,
(3) an alkynyl group.
(4) a group of the formula,

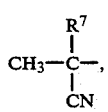

wherein R⁷ represents a hydrogen atom or a methyl group.

(5) a group of the formula, NC—(CH₂)$_p$—, wherein p is an integer of from 1 to 6.

(6) a group of the formula, A—(CH₂)$_p$— wherein A represents a group selected from a pyridyl group, a pyranyl group and a morpholino group and q is an integer of from 0 to 6.

(7) an alkyl group having from 1 to 6 carbon atoms wherein a phenyl group or a cycloalkyl group is joined to any carbon atom).

(8) a group of the formula,

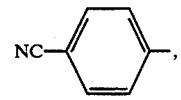

(9) a group of the formula,

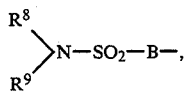

wherein R⁸ and
R⁹ are the same or different and represent a hydrogen atom, a lower alkyl group, a pyridylmethyl group or a cycloalkyl group or R⁸ and R⁹ may be joined along with a nitrogen atom to form a ring, and B represents a phenylene group or a lower alkylene group having 1 to 3 carbon atoms.

(10) a group of the formula,

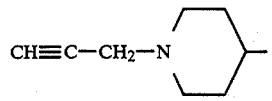

(11) a group of the formula,

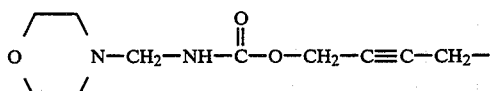

(12) a group of the formula,

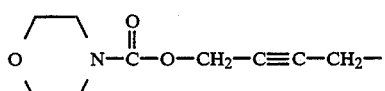

(13) a group of the formula,

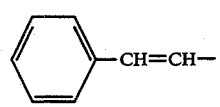

(14) a group of the formula,

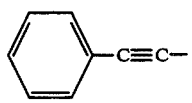

(15) a lower alkyl group, or
(16) a cycloalkylalkenyl group, provided that when X is

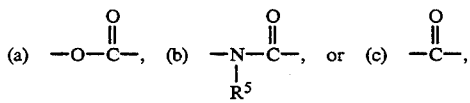

Y is a group selected from (1) to (14), and when X is

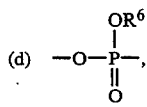

Y is a group of (15) and that when n=O, Y is an alkynyl group of (3). In addition, Y includes (17) to (23) defined before.

In the above general formula (D), R² represents a lower alkyl group having from 1 to 6 carbon atoms as set forth for the definition of R¹ and R² and is most preferably a methyl group.

The most preferable compound group where R² is a methyl group is represented by the following general formula (E)

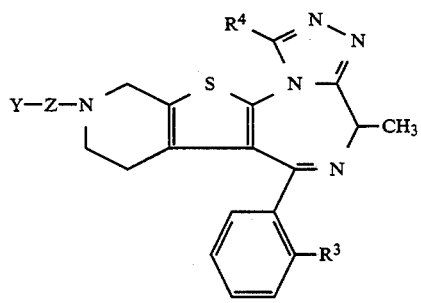

(E)

wherein Y, R³ and R⁴ have, respectively, the same meanings as defined before, Z represents a group of the formula,

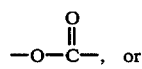

a group of the formula

In the above general formula (E), the case where R³ is a halogen atom is most preferable. The most preferable halogen atom is a chlorine atom.

R⁴ is preferably an alkyl group and most preferably a methyl group.

Y is most preferably a group of the formula,

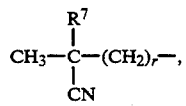

in which R7 is hydrogen or methyl and r is zero, 1 or 2, a group of the formula, NC—(CH₂)$_p$—, wherein p is an integer of from 1 to 6, a cycloalkyl group, a cycloalkylalkyl group, a cycloalkylalkenyl group, or a group, of the formula

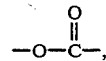

Especially, when Z is a group of the formula,

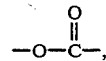

Y is most preferably an alkynyl group such as, for example, CH≡C—CH₂—, CH≡C—CH₂—CH₂—, CH≡C-2—CH₂—CH₂— or CH≡C—CH₂—CH₂—CH-2—CH₂—. A group of the formula,

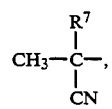

wherein R⁷ has the same meaning as defined before, or a group of the formula, NC—(CH₂)$_p$— wherein p has the same meaning as defined before.

When Z is a group of the formula,

Y is most preferably a cycloalkyl group such as a cycloalkylalkenyl cyclobutyl group, a cycloalkylalkyl group, a cycloalkylalkenyl group, an alkynyl group, a group of the formula

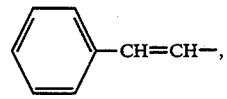

or a group of the formula, NC—(CH₂)$_p$— wherein p is an integer of from 1 to 6.

These compounds (E) and particularly, those compounds wherein the methyl group is introduced into the diazepine ring exhibit unexpectedly better anti-PAF action than known 1,4-diazepine compounds as will be described hereinafter.

The pharmacologically acceptable salts used in the present invention are ordinarily employed innoxious salts such as, for example, in organic salts such as hydrochlorides, hydrobromides, sulfates, phosphates and the like, organic salts such as acetates, maleates, succinates, methanesulfonates and the like, and salts of amino acids such as alginine, aspartic acid, glutamic acid and the like.

The compounds of the invention have asymmetric carbon in the molecule and may take various steric isomers. In the practice of the invention, the individual isomers and mixtures thereof are all within the scope of the invention. For example, the compound (D) defined above has an asymmetric carbon attached to Ra being methyl and therefore includes stereoisomers. The isomers can be obtained according to any usual process for preparation.

Moreover, some compounds may form hydrates, which are also within the scope of the invention.

The compounds of the invention are prepared by usual procedures, among which typical processes are described below.

Preparation Process 1

For the preparation of compounds of the formula (I) wherein X is of the formula (a),

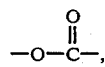     (a)

or of the formula (b),

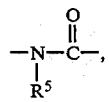     (b)

and n=1.

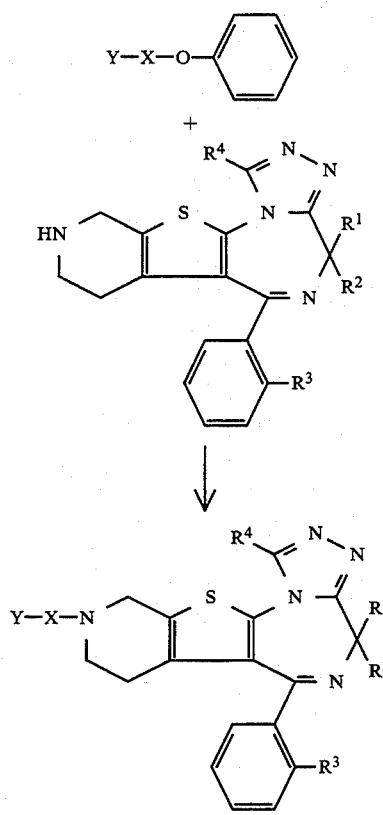

wherein X, n, Y, $R^1$, $R^2$, $R^3$ and $R^4$ have, respectively, the same meaning as defined before.

The compound of the formula (II) and the compound of the formula (III) are subjected to condensation reaction to obtain the compound of the general formula (I') which is one of intended substances.

This reaction is performed by usual manner in a solvent-free condition or in a solvent inert to the reaction and selected from chloroform, tetrahydrofuran, diethyl ether, acetone, benzene, toluene and dimethylformamide. The reaction temperature is generally from room temperature to approximately 150° C. and most preferably from 100° to 130° C.

In the above reaction, the compound of the general formula (II) which is used as the starting material is prepared, for example, according to the following process.

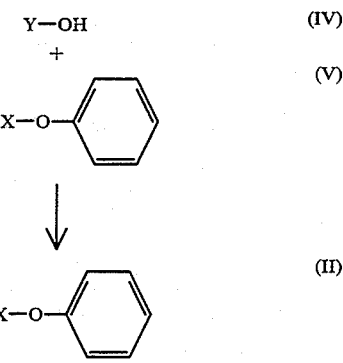

wherein Y, X and n have, respectively, the same meanings as defined before, and Hal represents a halogen atom.

In the above reaction, the compound of the general formula (IV) is subjected to a condensation reaction with the halide of the general formula (V) to obtain the compound of the general formula (II).

The reaction should preferably be effected in the presence of bases including amines such as triethylamine, pyridine and the like, alkali hydrides such as sodium hydride, potassium hydride and the like, and alkali hydroxides such as sodium hydroxide, potassium hydroxide and the like.

This reaction may be performed in the absence of solvent or in a solvent. Examples of the solvent include ethers such as tetrahydrofuran, dioxane and the like, halogen-based compounds such as methylene chloride, chloroform and the like, benzene compounds such as benzene, toluene, xylene and the like, and compounds such as dimethylformamide, dimethylsulfoxide and the like.

Preparation Process 2

For the preparation of compounds wherein X is of the formula,

and n=1.

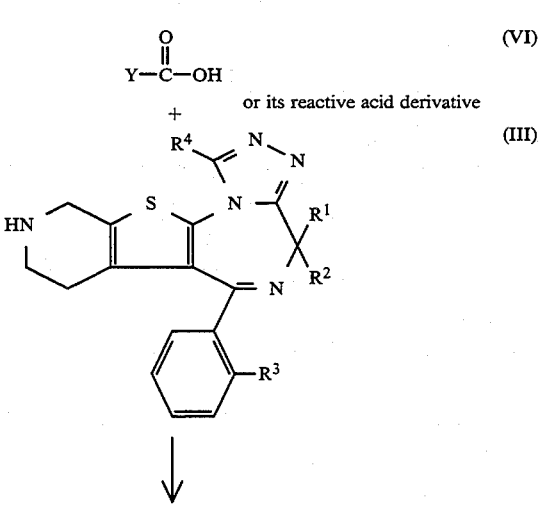

-continued

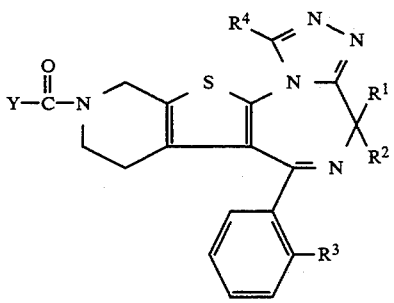 (I″)

More particularly, the carboxylic acid of the general formula (VI) or its reactive derivative and the compound of the general formula (III) are subjected to condensation reaction to obtain the compound of the general formula (I″) which is one of the intended substances.

This condensation reaction is carried out by the usual manner. The reactive derivatives include: acid halides such as acid chlorides, acid bromides and the like; acid azides; N-hydroxybenzotriazole; active esters such as N-hydroxysuccinimide; symmetric acid anhydrides; mixed acid anhydrides with alkali carbonates, p-toluenesulfonic acid and the like.

This reaction is carried out by heating in a solvent-free condition or in a solvent not taking part in the reaction, e.g. benzene, toluene, xylene, tetrahydrofuran, chloroform, carbon tetrachloride, dimethylformamide or the like, thereby causing, for example, a dehalogenation reaction. Better results are obtained when the reaction is effected in the presence of inorganic salts such as sodium hydrogencarbonate, potassium carbonate, sodium carbonate, caustic soda and the like or organic bases such as triethylamine, pyridine, pyrimidine, diethylaniline and the like.

When free carboxylic acids are used, better results are obtained for the reaction in the presence of a condensing agent such as dicyclohexylcarbodiimide, 1,1′-carbonyldiimidazole or the like.

Preparation Process 3

For the preparation of compounds wherein X is of the formula,

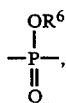

and n—1,

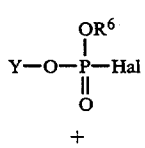 (VII)

+

-continued

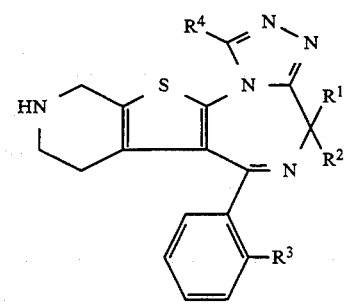 (III)

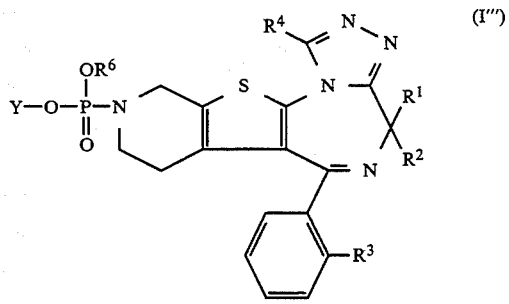 (I‴)

wherein Y, $R^1$, $R^2$, $R^3$, $R^4$ and $R^6$ have, respectively, the same meanings as defined before, and Hal represents a halogen atom.

The halide compound of the general formula (VII) and the compound of the general formula (III) are reacted to obtain compound (I‴) which is an intended substance.

The reaction is a dehydrohalogenation reaction which is effected by the usual manner under heating conditions in a solvent-free condition or in a solvent not taking part in the reaction and selected, for example, from benzene, toluene, xylene, tetrahydrofuran, chloroform, carbon tetrachloride and dimethylformamide. Better results are obtained when the reaction is carried out in the presence of inorganic salts such as sodium hydrogencarbonate, potassium carbonate, sodium carbonate and caustic soda or organic bases such as triethylamine, pyridine, pyrimidine, diethylaniline and the like.

Preparation Process 4

For the preparation of compounds of the formula (I) where n=0,

 (VIII)

+

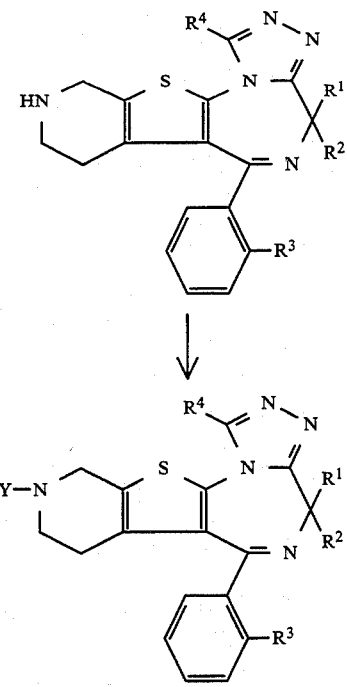

(III)

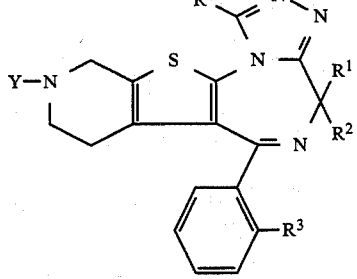

(I'''')

wherein Y, R¹, R², R³, and R⁴ have, respectively, the same meanings as defined before, and Hal represents a halogen atom.

The halide compound of the general formula (VIII) and the compound of the general formula (III) are reacted to obtain compound (I'''') which is an intended substance.

The reaction is a dehydrohalogenation reaction which is effected by usual manner under heating conditions in a solvent-free condition or in a solvent no taking part in the reaction and selected, for example, from benzene, toluene, xylene, tetrahydrofuran, chloroform, carbon tetrachloride and dimethylformamide. Better results are obtained when the reaction is carried out in the presence of inorganic salts such as sodium hydrogencarbonate, potassium carbonate, sodium carbonate and caustic soda or organic bases such as triethylamine, pyridine, pyrimidine, diethylaniline and the like.

The starting compound (III) used in the above Preparation Processes 1 to 4 can be prepared, for example, according to the following procedure.

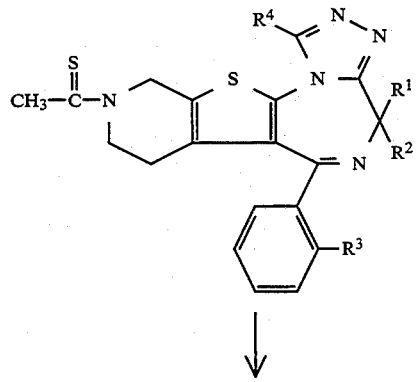

(IX)

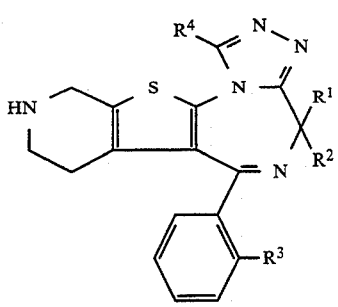

(III)

wherein R¹, R², R³, and R⁴ have, respectively, the same meanings as defined before.

In the above reaction, the thioamide compound of the general formula (IX) is subjected to hydrolysis reaction to obtain the compound of the general formula (III).

The present reaction is carried out by usual manner wherein the compound of the general formula (III) can be obtained by heating in the presence, for example, of sodium hydroxide, potassium hydroxide, sodium ethoxide, sodium methoxide, potassium ethoxide, potassium methoxide or the like. For the reaction, there may be used a solvent such as, for example, an alcohol solvent such as methyl alcohol, ethyl alcohol or the like, tetrahydrofuran, dimethoxyethane, or a hydrous solvent.

With the above starting compound (III) wherein R' is a hydrogen atom, R² is a methyl group and R⁴ is a methyl group, the preparation process can e more particularly described as follows.

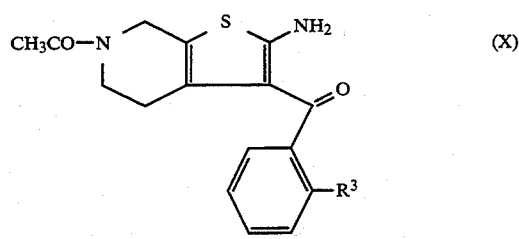

(X)

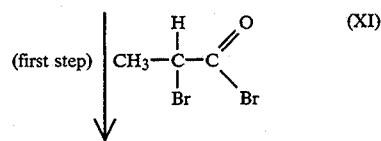

(XI)

(first step)

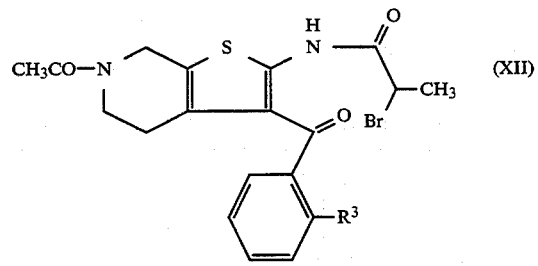

(XII)

(second step)

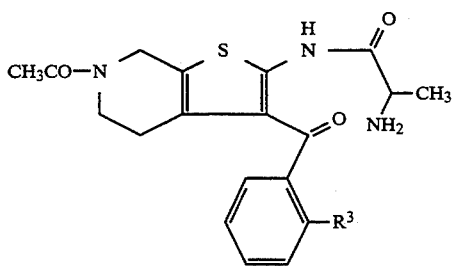 (XIII)

(third step) ↓

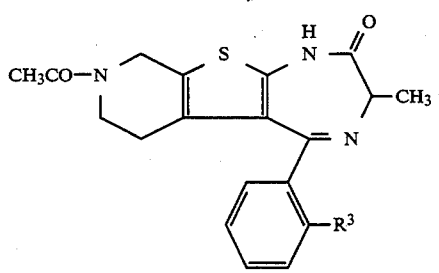 (XIV)

(fourth step) ↓ P₂S₅

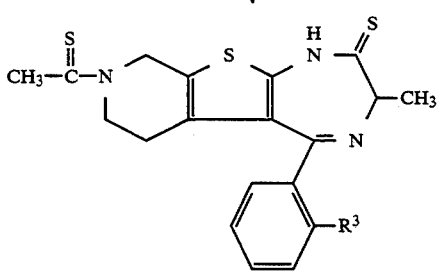 (XV)

(fifth step) ↓

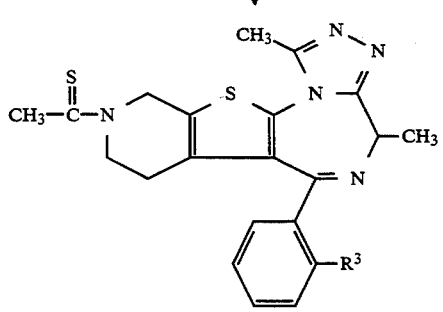 (XVI)

(sixth step) ↓

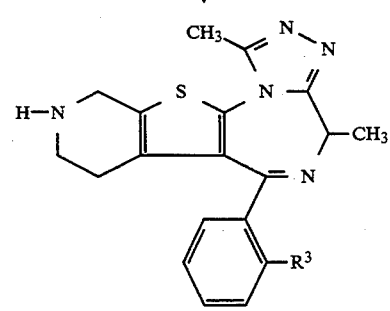 (XVII)

-continued

↓

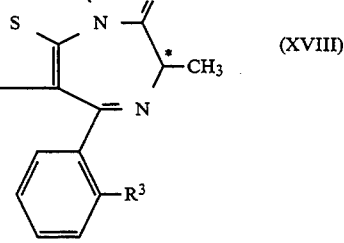 (XVIII)

wherein the mark "*" represents asymmetric carbon and (XVIII) represents the respective enanethiomer.

The respective steps indicated above are briefly illustrated in the following.

First Step

2-Bromopropionyl bromide of the formula (XI) is subjected to condensation reaction with the compound of the general formula (X) by usual manner to obtain the compound of the general formula (XII).

This reaction is carried out in a two-phase system (under Schotten-Bauimann conditions) of an organic solvent such as, for example, toluene, benzene, xylene or the like in the presence of either an alkali hydroxide such as sodium hydroxide, potassium hydroxide or the like or a base such as sodium hydrogencarbonate, potassium hydrogencarbonate or the like.

Alternatively, the reaction may be performed in the presence of a base including an amine such as triethylamine, pyridine or the like, an alkali hydroxide such as sodium hydroxide, potassium hydroxide or the like, or an alkali hydride such as sodium hydride, potassium hydride or the like, in a solvent not taking part in the reaction such as, for example, dichloromethane, dichloroethane, tetrahydrofuran, toluene, benzene, xylene, dimethylformamide or the like.

Second Step

In this step, ammonia gas is introduced into the compound of the general formula (XII) by usual manner to obtain the compound (XIII).

This reaction should preferably be effected at low temperatures ranging, for example, from 30° C. to 100° C.

The reaction is carried out in a solvent-free condition or by the use of an appropriate solvent which does not take part in the reaction and is selected from ethers such as tetrahydrofuran, dioxane and the like, ethyl acetate, chloroform, methanol, ethanol, pyridine and dichloroethane.

Third Step

In this step, the compound of the general formula (XII) is subjected to dehydration reaction by the usual manner thereby causing cyclization to obtain the compound of the general formula (XIV).

One of the procedures is particularly described. The compound is dissolved in an appropriate solvent not taking part in the reaction such as, for example, benzene, toluene, xylene, pyridine or the like, to which one equivalent of an acid catalyst such as acetic acid, silica gel or the like. While removing the water produced as the reaction proceeds by the use of a dehydrator or by means of the Dean Stark apparatus, the reaction system is heated.

Fourth Step

This step is one wherein phosphorus pentasulfide is added to the compound of the general formula (XIV) for reaction to obtain the compound of the general formula (XV).

This reaction is carried out in a solvent such as pyridine, dimethoxyethane, diglymes, tetrahydrofuran, toluene, benzene, xylene or the like. The reagent may be, aside from phosphorus pentasulfide, the Lauson reagent, (2,4-bis(4-methoxyphenyl9-1,3-dithia-2,4-diphosphetan-2,4-disulfide). In some case, the reaction is carried out in the presence of a base such as sodium hydrogencarbonate.

Fifth Step

This step involves the reaction wherein acetohydrazide is reacted with the compound of the general formula (XV) to cause the cyclization reaction, thereby obtaining compound of the general formula (XVI).

This reaction is effected by heating acetohydrazide in a solvent which does not take part in the reaction such as, for example, dioxane, dimethoxyethane, diglymes or the like or in a solvent-free condition. Alteratively, hydrazide hydrate is reacted in a solvent such as methanol or ethanol and the resultant hydrazide is reacted to ethyl ortho-acetate to obtain an intended product. Still alternatively, hydrazide may be reacted with acetyl chloride or acetic anhydride and the resultant product is dehydrated to obtain compound (XVI).

Sixth Step

This step is one wherein the compound of the general formula (XIV) is hydrolyzed by usual manner to obtain the compound of the general formula (XVII).

This reaction proceeds according to known procedures. For instance, heating in the presence of potassium hydroxide, sodium hydroxide, sodium ethoxide, sodium methoxide, potassium ethoxide, potassium methoxide or the like results in the compound of the general formula (XVII).

For the reaction, solvents may be used including alcohol solvents such as methyl alcohol or ethyl alcohol, tetrahydrofuran, dimethoxyethane or hydrous solvents.

A particular example of obtaining the compound of the general formula (XVII) through the above-described series of the reactions is illustrated in Preparatory Example appearing hereinafter wherein $R^3$ is a chlorine atom.

The compound of the general formula (XVII) is a novel compound and is an important intermediate for obtaining final compounds having good anti-PAF activity. More specifically, the final compound prepared through the intermediate (i.e. compounds of the general formula (I) wherein $R^1$ is a hydrogen atom and $R^2$ is a methyl group) exhibits unexpectedly high anti-PAF activity than known 1,4-diazepine compound. In this sense, the compounds of the general formula (III), of which those of the formula wherein $R^1$ is a hydrogen atom and $R^2$ is a lower alkyl group, particularly a methyl group, are very valuable as intermediates.

The intermediates have asymmetric carbon and thus optical isomers exist. In the practice of the invention, dl products may be resolved into optically active products, if desired.

Th resolution may be performed at the stage of the compound of the general formula (XIII) wherein an optical resolving agent such as (+)-tartaric acid, (+)-camphoric acid, (+)-dibenzoyltartaric acid, (+)-10-camphorsulfonic acid, (+)-mandelic acid or the like may be used for the resolution. Alternatively, at the stage of the compound of the general formula (III) or (XVII), the resolution may be possible using an optical resolving agent such as dibenzoyl-D-tartaric acid or dibenzoyl-L-tartaric acid. Still alternatively, when using a column for optical isomer resolution such as, for example, a chiral(?) polyamide silica gel HPLC (elute: tetrahydrofuran-hexane), the resolution at the stage of the compound of the general formula (XIII), (XVII) or (III) is possible.

The other compounds than those described for the processes for their preparations can be obtained in the same way, except for changing starting materials.

The effects of the invention are more particularly described by way of experimental example.

EXPERIMENTAL EXAMPLE

PAF Recepteor Binding Assay to the Human Platelet (Method)

Platelets are obtained from healthy men according to usual method and suspended at a concentration of $10^8$ platelets/460 μl in a binding buffer (10 mM phosphate-buffers saline (pH 7.0), with 0.1% (w/V) BSA and 0.9 mM $CaCl_2$). Platelets ($10^8$) in 460 μl of the buffer were added to polypropylene tubes and preincubated with test compounds (20 μl), after vortexing, for 6 min at 37° C. Subsequently, 20 μl of a binding buffer solution of $^3$H-PAF (final $^3$H-PAF concentration 0.6–1 nM) was added to the tubes, which were incubated for 6 minutes. The binding reaction was stopped by adding of 3 ml of an ice-cold washing solution (saline containing 0.1% (w/v) BSA). Platelets were isolated by vacuum filtration on glass filters (Whatman GF/C). After drying the glass filter, radioactivity on the glass filter was measured in scintilator with a liquid scintillation counter.

The inhibition percent is calculated according to the following equation and the value of IC is determined by interpolation from the figure.

$$\text{Inhibition \%} = \frac{\text{(total binding)} - \text{(total binding with compound)}}{\text{(total binding)} - \text{(non-specific binding total)}}$$

binding : radioactivity of binding in the absence of cold PAF or test compounds non-specific binding : radioactivity of binding in the presence of $10^{-5}$ M PAF These results are shown in Table I.

non-specific binding : radioactivity (dpm) after the incubation with $10^{-5}$ M of cold PAF.

The results are shown in Table 1.

The mark " " indicates asymmetric carbon and the marks "(+)" and "(−)" indicate specific rotation.

As shown in Table 1, it is obvious that these invented compounds have anti-PAF activity. Moreover, it has been found that the compounds possess more potent and long-acting anti-PAF activity, and show better safety properties than known compounds. Thus, the present invention has a great merit.

Accordingly, the compounds will be effective for the therapy and prophylaxis of all diseases mediated by PAF.

Typical diseases for which the compounds are useful as a therapeutic and prophylactic agent include allergic diseases, asthma, thrombosis, cerebral apoplexy (cerebral hemorrhage, cerebral thrombosis), myocardial infarction, (angina pectoris), human disseminated intravascular coagulation syndrome (DIC), thrombophlebitis, glomerular heptitis, anaphylactic shock, hemorrhagic shock and the like. The invented compounds will be particularly useful as an anti-allergic agent and an anti-asthmatic agent.

When these compounds are administered as an anti-PAF agent, they may be useful to orally dose in the form of a tablet, powder, granule, capsule, syrup or the like. Alternatively,they may be parenterally dosed as a suppositoty, injection, external remedy or drip. In the case of the invention, the compounds should preferably be used as an oral agent.

The dosage may depend on the type of disease, the degree of symptom and the age. When these compounds are orally administered, the doses of 0.001–10 mg/kg, preferably 0.01–0.5 mg/kg, will be benefitial.

For the preparations to use as peroral and parenteral dose, they are made using ordinary, pharmaceutically acceptable additives. For the preparation of injections or drips, pH modifiers, buffer solutions, stabilizers and solubilizers are added to the principal ingredient, if necessary. The mixture can be freeze-dried, if necessary, to made injections for subcutaneous, intramuscular or intervenous or drip administrations.

TABLE 1

| Test compound | PAF receptor binding assay IC$_{50}$ ($\mu$M) |
|---|---|
| [structure] | 0.0033 |
| [structure] | 0.0027 |
| [structure] | 0.0035 |

TABLE 1-continued

| Test compound | PAF receptor binding assay IC$_{50}$ (μM) |
|---|---|
| (structure: cyclobutyl-C(O)-N-piperidine fused thieno ring with 2-CH$_3$-triazole and 2-chlorophenyl imine) | 0.0018 |
| (structure: phenyl-C≡C-C(O)-N- thienopiperidine with triazole and 2-chlorophenyl) | 0.00056 |
| (structure: HC≡C-(CH$_2$)$_4$-O-C(O)-N- thienopiperidine with triazole and 2-chlorophenyl) | 0.00022 |
| (structure: C$_2$H$_5$-C≡C-CH$_2$-O-C(O)-N- thienopiperidine with triazole and 2-chlorophenyl) | 0.00074 |

TABLE 1-continued
| Test compound | PAF receptor binding assay IC$_{50}$ (μM) |
|---|---|
| 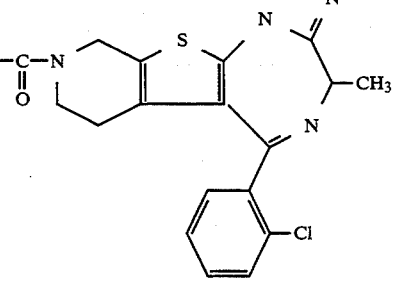 | 0.0015 |
| 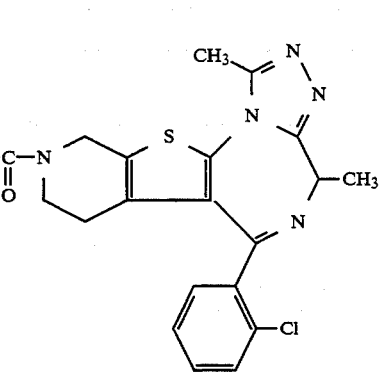 | 0.0044 |
| 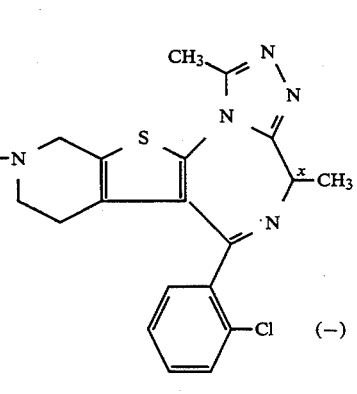 (−) | 0.5 |
| 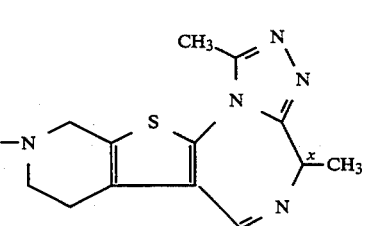 (+) | 0.0031 |

TABLE 1-continued

| Test compound | PAF receptor binding assay IC$_{50}$ (μM) |
|---|---|
| 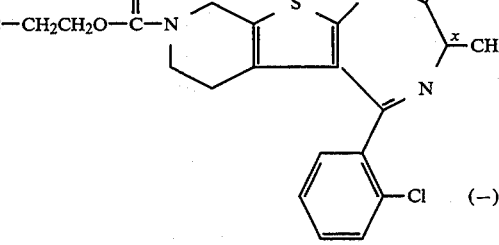 (−) | 0.082 |
| 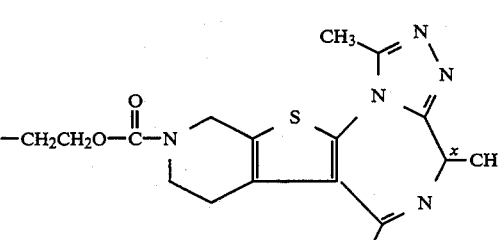 (+) | 0.00034 |
| 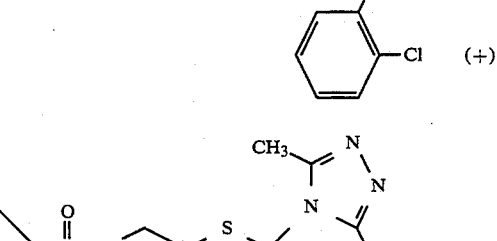 (−) | 0.42 |
| 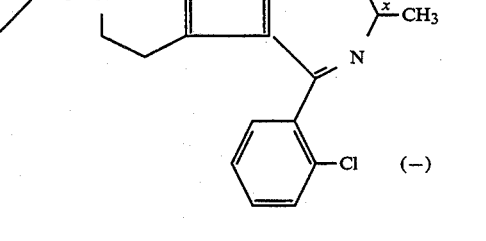 (+) | 0.0028 |

EXAMPLES

Typical examples of the invention are described, which should not be construed as limiting the present invention.

(A) Examples 1 to 77 and Preparation Examples 1 to 29, (B) Examples 78 to 104 and Preparation Examples 30 to 34, (C) Examples 105 to 120 and Preparation Examples 35 to 43, and (D) Examples 121 to 137 and Preparation Examples 44 to 52 are disclosed hereinafter.

It will be noted that the preparation of starting compounds or substances will be described as Preparatory Examples.

EXAMPLE 1

6-(2-Chlorophenyl)-3-(1-cyano-1-methylethoxycarbonyl)-11-m-ethyl-2,3,4,5-tetrahydro-8H-pyrido[4',3':4,5]thieno[3,2-f][1,2,4]triazolo[4,3-a][1,4]diazepine

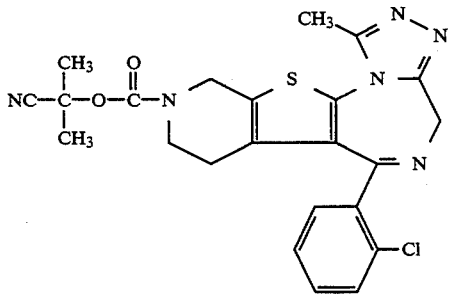

(1) Synthesis of 1-cyano-1-methylethyl phenyl carbonate

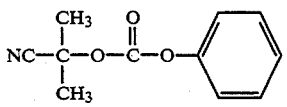

1.40 g (9 mmols) of phenyl chloroformate was dropped into a pyridine solution (20 ml) of 0.85 g (10 mmols) of acetone cyanohydrin under ice-cooling conditions, followed by agitation for 30 minutes. After completion of the reaction, the solvent was distilled off to obtain a residue, which was dissolved in chloroform, followed by washing with N hydrochloric acid and a saturated sodium hydrogencarbonate aqueous solution and drying with magnesium sulfate. The resultant product was purified by silica gel column chromatography (elution solvent: ethyl acetate:n-hexane=1:49), thereby quantitatively obtaining the intended compound in the form of a colorless solid matter.

(2) Synthesis of 6-(2-chlorophenyl)-3-(1-cyano-1-methylethoxycarbonyl)-11-methyl-2,3,4,5-tetrahydro-8H-pyrido[4',3':4,5]thieno[3,2-f][1,2,4]triazolo[4,3-a][1,4]diazepine

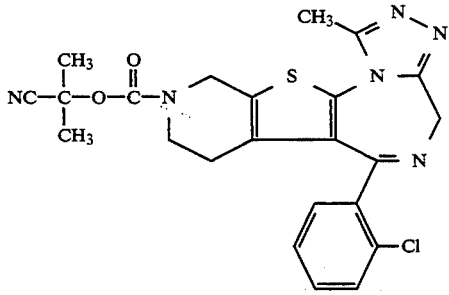

0.15 g of 1-cyano-1-methylethyl phenyl carbonate and 0.15 g of 6-(2-chlorophenyl)-11-methyl-2,3,4,5-tetrahydro-8H-pyrido[4',3':4.5]thieno[3,2-f][1,2,4]trizolo[4,3-a][1,4]diazepine were dissolved in chloroform and made uniform, after which the solvent was distilled off. The resultant mixture was agitated at a bath temperature of 120° C. for 1 hour. After cooling, purification by silica gel column chromatography (elution solvent: chloroform:methanol=99:1) could yield 0.18 g of the intended product as amorphous.

$^1$H-NMR (90MHz, CDCl$_3$) δ1.77(6H,s), 180-2.20(2H,m), 2.68(3H,s), 3.10-3,60(2H,m), 4.22(1H,m), 4.50-4.88(2H,m), 5.60(1H,m), 7.35(4H,m)
FABMS (M+H+) m/z:481

EXAMPLE 2

6-(2-Chlorophenyl)-3-(3-cyanopropoxycarbonyl)-11-methyl-2,3,4,5-tetrahydro-8H-pyrido[4',3':4.5]-thieno[3,2-f][1,2,4]triazolo[4,3-a][1,4]diazepine

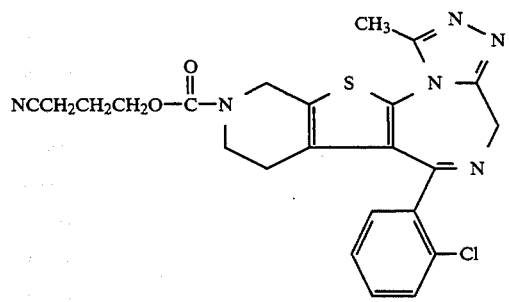

(1) Synthesis of 3-cyanopropyl phenyl carbonate

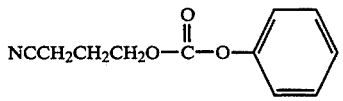

1.50 g of phenyl chloroformate was dropped into a chloroform solution (20 ml) of 0.85 g of 4-hydroxybutyronitrile and 1.50 g of pyridine under ice-cooling conditions, followed by agitation for 30 minutes. After completion of the reaction, the reaction mixture was washed with a saturated sodium hydrogencarbonate aqueous solution and dried with magnesium sulfate, after which the solvent was distilled off, followed by purification by silica gel column chromatography (elution solvent: ethyl acetate: n-hexane=3: 17), thereby obtaining 1.20 g of the intended compound.

(2) Synthesis of 6-(2-chlorophenyl)-3-(3-cyanopropoxycarbonyl)-11-methyl-2,3,4,5-tetrahydro-8H-pyrido[4',3':4,5]thieno[3,2-f][1,2,4]triazolo[4,3-a][1,4]diazepine

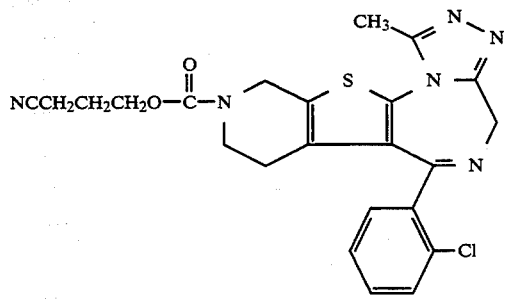

0.11 g of 1-cyanopropyl phenyl carbonate and 0.13 g of 6-(2-chlorophenyl)-11-methyl-2,3,4,5-tetrahydro-8H-pyrido[4',3':4,5]thieno[3,2-f][]1,2,4]triazolo[4,3-a][1,4]diazepine were dissolved in chloroform and made uniform, after which the solvent was distilled off. The resultant mixture was agitated at a bath temperature of 110° C. for 1 hour. After cooling, purification by silica gel column chromatography (elution solvent: chloroform:methanol=49:1) could yield 0.10 g of the intended product.

$^1$H-NMR (90MHz, CDCl$_3$) δ1.41–1.80(m, 2H), 1.80–2.17(m, 2H), 2.22–2.52(m,2H), 2.60(s, 3H), 2.80–5.76(m, 6H), 4.20(t, J=7Hz, 2H), 7.30(m, 4H)

FABMS (M+H+) m/z:481

EXAMPLE 3

3-(3-Butynyloxycarbonyl)-6-(2-chlorophenyl)-11-methyl-2,3,4,5-tetrahydro-8H-pyrido[4′,3′:4.5]thieno[3,2-f][1,2,4]triazolo[4,3-a][1,4]diazepine

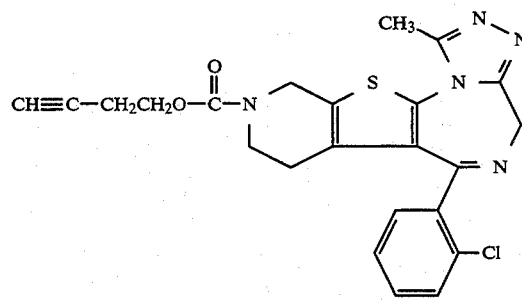

(1) Synthesis of 3-butynyl phenyl carbonate

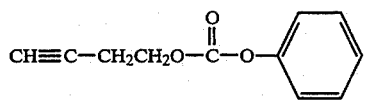

1.70 g of phenyl chloroformate was dropped in to a dichloromethane solution (20 ml) of 0.70 g of 3-butyn-1-ol and 1.50 g of pyridine under ice-cooling conditions, followed by agitation for 30 minutes. After completion of the reaction, the reaction mixture was washed with a saturated sodium hydrogen carbonate aqueous solution and dried with magnesium sulfate, after which the solvent was distilled off, followed by purification by silica gel column chromatography (elution solvent: ethyl acetate: n-hexane=1: 49), thereby obtaining the intended compound as a colorless oil at a quantitative yield.

(2) Synthesis of 3-(3-butynyloxycarbonyl)-6-(2-chlorophenyl-propoxycarbon)-11-methyl-2,3,4,5-tetrahydro-8H-pyrido[4′,3′:4,5]thieno[3,2-f][1,2,4]triazolo[4,3-a][1,4]diazepine

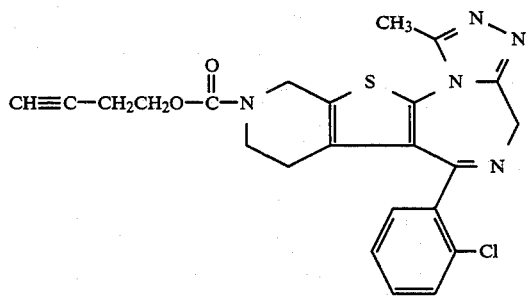

0.10 g of 3butynyl phenyl carbonate and 0.18 g of 6-(2-chlorophenyl)-11-methyl-2,3,4,5-tetrahydro-8H-pyrido[4′,3′:4,5]thieno[2,3-f[]1,2,4]triazolo[4,3-a][1,4]diazepine were dissolved in chloroform and made uniform, after which the solvent was distilled off. The resultant mixture was agitated at a temperature of 100° C. for 1 hour. After cooling, purification by silica gel column chromatography (elution solvent: chloroform:methanol=99:1) could yield 0.17 g of the intended product.

$^1$H-NMR (90MHz, CDCl$_3$) δ1.60–2.16(m, 2H), 1.94 (s,3H), 2.50(dt, J=2Hz, 7Hz, 2H), 2.66(s, 3H), 2.86–5.74(m, 6H), 4.17(t, J=7Hz, 2H), 7.29(m, 4H)

MS m/z(Pos. Gab):466(M+H)+

EXAMPLE 4

6-(2-Chlorophenyl)-3-(2-cyanoethylaminocarbonyl)-11-methyl-2,3,4,5-tetrahydro-8H-pyrido[4′,8′:4,5]-thieno[3,2-f][1,2,4]triazolo[4,3-a][1,4]diazepine

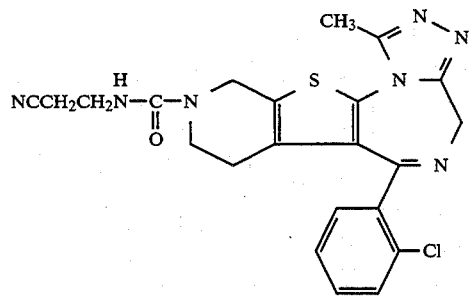

(1) Synthesis of N-(2-cyanoethyl)carbamate

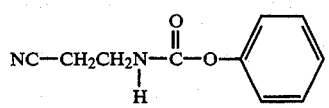

1.40 g of phenyl chloroformate was dropped in to a dichloroethane solution (20 ml) of 0.70 g of 3-aminopropionitrile and 1.20 g of triethylamine under ice-cooling conditions, followed by agitation for 30 minutes.

After completion of the reaction, the reaction mixture was washed with saturated sodium hydrogen carbonate and dried with magnesium sulfate, after which the solvent was distilled off, followed by purification by silica gel column chromatography (elution solvent: ethyl acetate: n-hexane=1:9), thereby obtaining 1.30 g of the intended compound.

(2) Synthesis of 6-(2-chlorophenyl)-3-(2-cyanoethylaminocarbonyl)-11-methyl-2,3,4,5-tetrahydro-8H-pyrido[4′,3′:4,3]thieno[3,2-f][1,2,4]triazolo[4,3-a[]1,4-diazepine

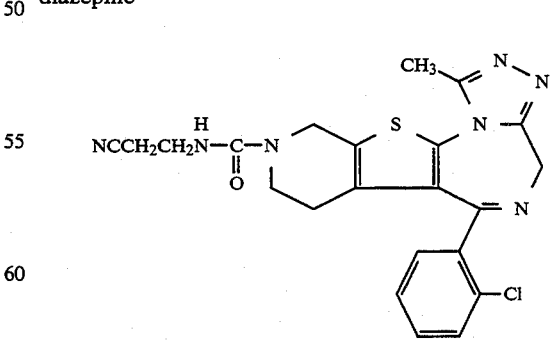

0.09 g of N-(2-cyanoethyl)carbamate and 0.18 g of 6-(2-chlorophenyl)-11-methyl-2,3,4,5-tetrahydro-8H-pyrido[4′,3′:4,5]thieno[3,2-f][1,2,4]triazolo[4,3-a][1,4]diazepine were dissolved in chloroform and made uniform, after which the solvent was distilled off. The resultant mixture was agitated at 140° C. for 1 hour. After cooling, purification by silica gel column chromatography (elution solvent: chloroform:methanol=19:1) could yield 0.12 g of the intended product.

¹H-NMR (90MHz, CDCl₃) δ: 1.45–2.23(m, 2H), 2.60(t, J=7Hz, 2H), 2.64(s,3H), 2.80–5.69(m, 9H), 7.29(m, 4H)

MS m/z(Pos, Fab):466 (M+H)⁺

EXAMPLE 5

6-(2-Chlorophenyl)-11-methyl-2-(2-propynyl)-2,3,4,5-tetrahydro-8H-pyrido[4',3',:4.5]thieno[3,2-f][1,2,4]triazolo[4,3-a][1,4]diazepine

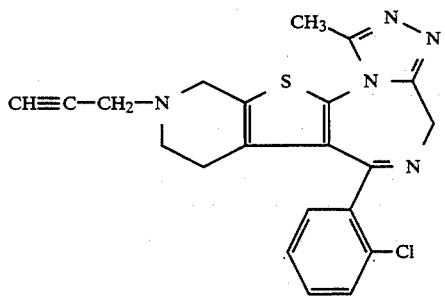

30 mg of sodium hydride (60%) was added to a dimethylformamide (20 ml) solution of 0.12 g of 6-(2-chlorophenyl)-11-methyl-2,3,4,5-tetrahydro-8H-pyrido[4',3':4,5]thieno[3,2-f][1,2,4]triazolo[4,3-a][1,4]diazepine at room temperature, followed by agitation at 60° C. for 1 hour. Again, 60 mg of 3-bromopropyne was added at room temperature and agitated at 60° C. for 1 hour. After cooling, water was added to the reaction mixture, which was extracted with ethyl acetate and dried with magnesium sulfate, followed by removal of the solvent and purification by silica gel column chromatography (elution solvent:chloroform:methanol=98.5:1.5),thereby obtaining 20 mg of the intended product.

¹H-NMR (90MHz, CDCl₃) δ 1.52–2.12(m, 2H), 2.25(t, J=2Hz, 1H), 2.16–2.84(m, 2H), 2.66(s, 3H), 3.45(d, J=2Hz,2H), 3.74(m, 2H), 3.90–4.40, 5.20–5.76(2m, 2H), 7.27(m, 2H)

MS m/z:407

EXAMPLE 6

6-(2-Chlorophenyl)-11-methyl-3-cyclopropanecarbonyl-11-methyl-2,3,4,5-tetrahydro-8H-pyrido[4',3':4,5]-thieno[3,2-f][1,2,4]triazolo[4,3-a][1,4]diazepine

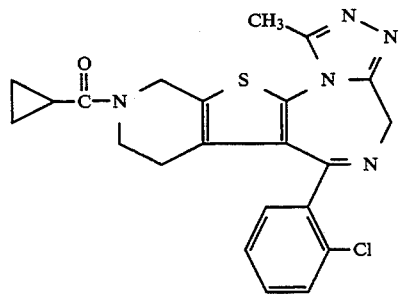

90 mg of cyclopropanecarbonyl chloride was dissolved in 4 ml of N,N-dimethylformamide, into which an N,N-dimethylformamide solution (6 ml) of 150 mg of 6-(2-chlorophenyl)-11-methyl-2,3,4,5-tetrahydro-8H-pyrido[4',3':4,5]thieno[3,2-f]-[1,2,4-triazolo[4,3-a][1,4]diazepine and210 mg of triethylamine was dropped at −60° C. and agitated as it is for 30 minutes. After removal of the solvent by distillation, a saturated sodium hydrogen carbonate aqueous solution was added, followed by extraction with chloroform and drying with anhydrous magnesium sulfate. This was filtered off and, after removal of the solvent by distillation, the resultant residue was subjected to silica gel column chromatography (developing solvent: MeOH:CH₂Cl₂=1:99) to obtain 140 mg of the captioned compound (yield 79%).

¹H-NMR (90MHz, CDCl₃) δ: 0.4–1.3 (m,4H), 1.4–2.7(m, 3H), 2.67(s,3H), 2.8–5.8(m, 6H), 71.–7.6(m, 4H),

MS m/z (Pos. Fab): 438(M+H)⁺

EXAMPLE 7

6-(2-Chlorophenyl)-3-cyclopropanecarbonyl-8,11-dimethyl-2,3,4,5-tetrahydro-8H-pyrido[4',3':4,5]-thieno[3,2-f][1,2,4]triazolo[4,3-a][]1,4]diazepine

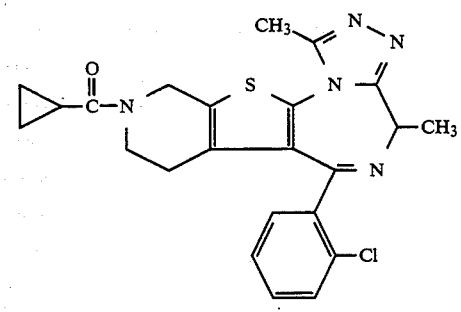

100 mg of 6-(2-chlorophenyl)-3-cyclopropanecarbonyl-11-methyl-2,3,4,5-tetrahydro-8H-pyrido[4',3':4,5]-thieno[3,2-f][1,2,4]triazolo[4,3-a][]1,4]diazepine was dissolved in 4 ml of N,N-dimethylformamide, to which 54 mg of sodium hydride (55%) and 0.5 ml of methyl bromide, followed by agitation for 1 hour at room temperature. The reaction was stopped by addition of water and the solution was neutralized with acetic acid. Subsequently, the solvent was distilled off under reduced pressure and the resultant residue was extracted with 20 ml of dichloromethane. The solution was dried with anhydrous magnesium sulfate, after which the solvent was removed followed by purification with silica gel column chromatography (400 mesh, 10 g) to obtain the captioned product.

¹H-NMR (90MHz, CDCl₃) δ: 0.55–1.15 (m, 4H), 1.45–2.5(m, 3H), 2.10(d, J=6.8 Hz,3H), 2.66(s, 3H), 2.8–4.8(m,3H), 4.26(q, J=6.8Hz, 1H), 4.8–5.2(m,1H), 7.05–7.65(m, 4H)

MS m/z(Pos. Fab.): 452(M+H)⁺

EXAMPLE 8

6-(2-Chlorophenyl)-3-cinnamoyl-11-methyl-2,3,4-tetrahydro-8H-pyrido[4',3':4.5]thieno[3,2-f][1,2,4]triazolo[4,3-a][1,4-diazepine

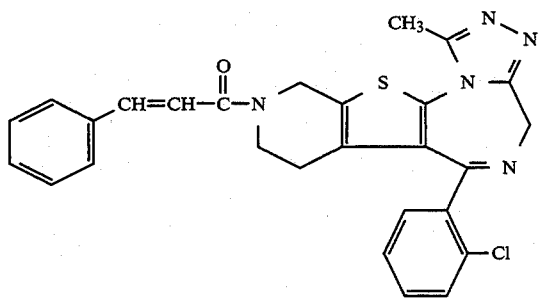

80 mg of cinnamoyl chloride was dissolved in 8 ml of N,N-dimethylformamide, into which 4 ml of an N,N-dimethylformamide solution of 120 mg of 6-(2-chlorophenyl)-11-methyl-2,3,4,5-tetrahydro-8H-pyrido[4',3':4,5]thieno[3,2-f[]1,2,4triazolo[4,3-a[]1,4]diazepine and 160 mg of triethylamine was dropped, followed by agitation as it is, After removal of the solvent by distillation, a saturated sodium hydrogencarbonate aqueous solution was added to, followed by extraction with chloroform and drying with anhydrous magnesium sulfate. The solution was filtered off and, after removal of the solvent by distillation, the resultant residue was subjected to silica gel column chromatography (developing solvent: MeOH:CH$_2$Cl$_2$=1:99) to obtain 11 mg of the captioned compound (yield 68%).

MS m/z(Pos. Fab): 500(M+H)+

EXAMPLE 9

6-(2-Chlorophenyl)-3-cyclobutanecarbonyl-11-methyl-2,3,4,5-tetrahydro-8H-pyrido[4',3':4,5]thieno[2,3-f][1,2,4triazolo[4,3-a][1,4[diazepine

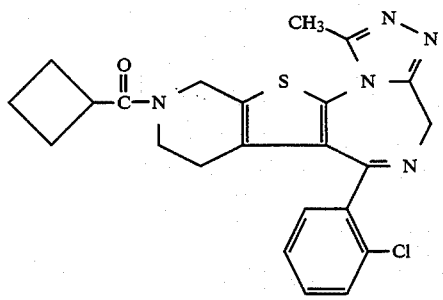

50 mg of cyclobutanecarboxylic acid, 70 mg of 1-hydroxybenzotriazole monohydrate and 150 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine was dissolved in 8 ml of N,N-dimethylformamide, to which 100 mg of N,N'-dicyclohexylcarbodiimide was added under ice-cooling conditions, followed by agitation for about 10 minutes and agitation at 4° C. overnight. Thereafter, after further agitation at room temperature for about 1 hour, the insoluble matter was removed by filtration and the solvent was distilled off. A saturated sodium hydrogencarbonate aqueous solution was added, followed by extraction with chloroform and drying with anhydrous magnesium sulfate. The resultant solution was subjected to filtration and the solvent was distilled off, and the residue was subjected to silica gel column chromatography (developing solvent: MeOH:CH$_2$CL$_2$=1:99) to obtain 180 mg of the intended compound (yield 98%).

$^1$H-NMR (90MHz, CDCl$_3$) δ: 1.4–2.5(m, 9H), 2.67(s, 3H), 2.8–5.9(m,6H), 7.1–7.6(m,4H)

MS m/z(Pos. Fab): 452(M+H)+

EXAMPLE 10

6-(2-Chlorophenyl)-3-diethylphosphoro-11-methyl-2,3,4,5-tetrahydro-8H-pyrido[4',3':4,5]thieno]3,2-f][1,2,4]triazolo[4,3-a][1,4]diazepine

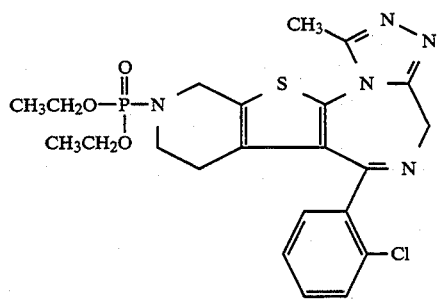

100 mg of 6-(2-chlorophenyl)-11-methyl-2,3,4,5-tetrahydro-8H-pyrido[4',3':4,5]thieno]3,2-f][1,2,4]triazolo[4,3-a][1,4-diazepine was dissolved in 5 ml of tetrahydrofuran and 1 ml of triethylamine, to which 100 mg of diethylchlorophosphate, followed by agitation at room temperature for 1 hour. The reaction solution was added to a saturated sodium bicarbonate aqueous solution, followed by extraction with ethyl acetate and drying with anhydrous magnesium sulfate. The solvent was removed for concentration under reduced pressure and the resultant residue was purified by silica gel column chromatography (developing solvent: CH$_3$OH:CH$_2$Cl$_2$=5:95) to obtain 100 mg of the intended compound (yield 72%).

MS(FAB)(M+H)+ =506

NMR (90MHz): 1.28(t, 6H, J=8.0), 1.44–2.20(m, 2H), 2.69(s, 3H), 3.70–4.60(m,9H), 5.33–5.72(m, 1H), 7.12–7.48(m,5H)

EXAMPLE 11

3-(3-butynyloxycarbonyl)-6-(2-chlorophenyl)-8,11-dimethyl-2,3,4,5-tetrahydro-8H-pyrido[4',3':4,5]-thieno[3,2-f][1,2,4]triazolo[4,3-a][1,4]diazepine

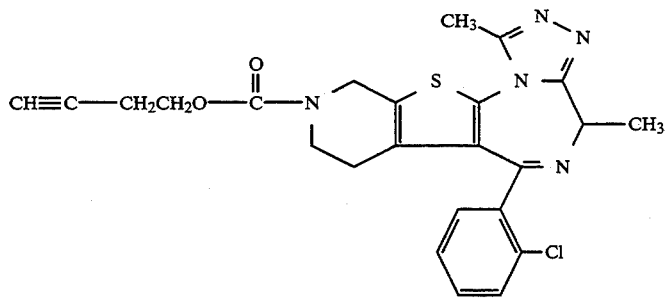

To a solution of 75 mg of 3-(3-butynyloxycarbonyl)-6-(2-chlorophenyl)-11-methyl-2,3,4,5-tetrahydro-8H-pyrido[4',3':4,5]thieno]3,2-f][1,2,4]triazolo[4,3-a][1,4]diazepine dissolved in dimethylformamide (2 ml) were added 28 mg of sodium hydride (55%) and 0.2 ml of methyl bromide, followed by agitation at at room temperature for 1 hour.

Water was added to the solution in order to stop the reaction and the solution was neutralized with acetic acid. The solvent was distilled off under reduced pressure and the resultant residue was extracted with 10 ml of dichloromethylene and then with 20 ml of dichloromethylene. The solution was dried with magnesium sulfate and the solvent was removed, followed by purification with silica gel column chromatography (400 mesh, 10 g, elution solvent: methanol:dichloromethane=1:99), thereby obtaining 25 mg of the intended compound.

NMR (90MHz, CDCl$_3$): 7.4(5H, Ar), 4.9(1H,d,J=18Hz, N—CH$_2$[C-2]), 4.5(1H,d,J=18Hz,N—CH$_2$[C-2]), 4.2(1H,m,C$_8$—H), 4.1(2H,t,J=8Hz,O—CH$_2$), 2.7(3H, s), 2.5(2H,dt,J=1.7Hz≡—CH$_2$), 2.1(3H,d,J=7Hz CHCH$_3$), 3.0–2.0(5H,m)

EXAMPLE 12

6(2-Chlorophenyl)-8,11-dimethyl-3-(3-cyanopropoxycarbonyl)-2,3,4,5-tetrahydro-8H-pyrido[',3':4.5]-thieno[3,2-f][1,2,4]tri-azolo[4,3-a][1,4]diazebine

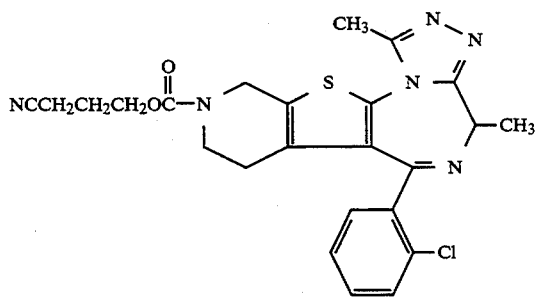

To a solution of 62 mg of 6-(2-chlorophenyl)-3-(3-cyanopropoxycarbonyl)-11-methyl-2,3,4,5-tetrahydro-8H-pyrido[4',3':4,5]thieno[3,2-f][1,2,4]triazolo-[4,3-a][1,4]diazepine dissolved in 2 ml of dimethylformamide at room temperature were added 34 mg of sodium hydride (55%) and 0.2 ml of methyl bromide, followed by agitation at room temperature for 1 hour. Water was added to the solution in order to stop the reaction and the solution was neutralized with acetic acid. The solvent was distilled off under reduced pressure and the resultant residue was extracted with 10 ml of dichloromethylene and then with 20 ml of dichloromethylene. The solution was dried with magnesium sulfate and the solvent was removed, followed by purification with silica gel column chromatography (400 mesh, 10 g, elution solvent: methanol:dichloromethane=1:99), thereby obtaining 21 mg of the intended compound.

NMR (90MHz, CDCl$_3$): 7.4(5H,Ar), 4.9(1H,d,J=18Hz, N—CH$_2$[C-2]), 4.5(1H,d,J=18Hz,N—CH$_2$[C-2]), 4.2(1H,m,C$_9$—H) 4.1(2H,t,J=8Hz,O—CH$_2$), 2.7(3H,s), 2.4(3H,d,J=7Hz), 2.1(3H,d,J=7Hz CHCH$_3$), 3.0–2.0(6H,m)

EXAMPLE 13

6-(2-Chlorophenyl)-8,8-diethyl-3-(3-cyanopropoxycarbonyl)-11-methyl-2,3,4,5-tetrahydro-8H-pyrido[4',3':4,5]thieno[3,2-f][1,2,4]tri-azolo[4,3-a][1,4]diazepine

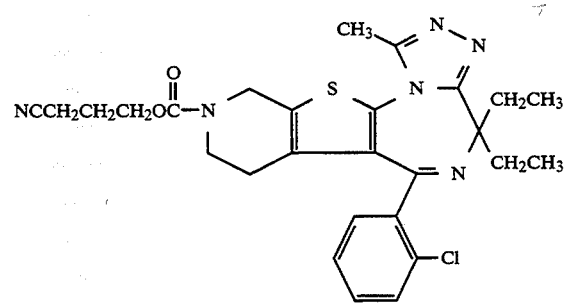

To a solution of 60 mg of 6-(2-chlorophenyl)-3-(3-cyanopropoxycarbonyl)-11-methyl-2,3,4,5-tetrahydro-8H-pyrido[4',3':4,5]thieno[3,2-f][1,2,4]triazolo-[4,3-a][1,4]diazepine dissolved in 2 ml of dimethylformamide at room temperature were added 10 mg of sodium hydride (55%) and 0.03 ml of methyl bromide, followed by agitation at at room temperature for 2 hours.

The thin layer chromatography revealed the presence of the starting compound and two novel products including a monomethyl product and a diethyl product. Accordingly, 10 mg of sodium hydride and 0.03 ml of ethyl bromide were further added and agitated for 2 hours, after which water was added to the solution in order to stop the reaction and the solution was neutralized with acetic acid. The solvent was distilled off under reduced pressure and the resultant residue was extracted with 10 ml of dichloromethylene and then with 20 ml of dichloromethylene. The solution was dried with magnesium sulfate and the solvent was removed, followed by purification with silica gel column chromatography (400 mesh, 13 g, elution solvent: methanol:dichloromethane=1:99), thereby obtaining 41 mg of the intended compound.

NMR (90MHz, CDCl₃): 7.4(5H,Ar), 4.9(1H,d,J=18Mz), N—CH₂(C-2]), 4.5(1H,d,J=18Hz,N—CH₂[C-2]), 4.1(2H,t,J=8H₂O—CH₂), 2.7(3H,s,CH₃), 2.0–2.7(10H,), 1.3(6H,t,J=7Hz,CH₃CH₃)

EXAMPLE 14

3-(3-Butynyloxycarbonyl)-6-(2-chlorophenyl)-8,8-diethyl-11-methyl-2,3,4,5-tetrahydro-8H-pyrido[4',3':4,5]thieno[3,2-f][1,2,4]triazolo[4,3-a][1,4]diazepine

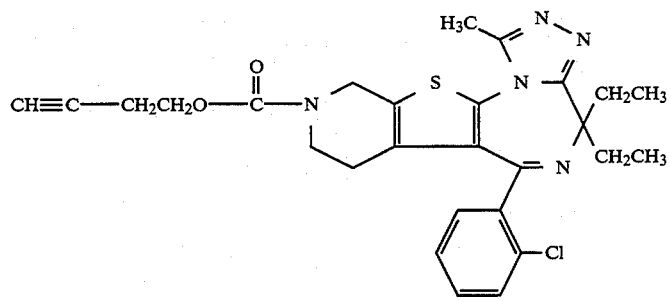

The general procedure of Example 12 was repeated using 65 mg of 3-(3-butynyloxycarbonyl)-6-(2-chlorophenyl-11-methyl-2,3,4,5-tetrahydro-8H-pyrido[4',3':4,5]thieno[3,2-f][1,2,4]triazolo[4,3-a][1,4]diazepine,thereby obtaining 23 mg of the intended product.

NMR (90MHz, CDCl₃):
7.4(5H,Ar), 4.9(1H,d,J=18Hz, N—CH₂(C-2]), 4.5(1H,d,J=18Hz,N—CH₂[C-2]), 4.1(2H,t,J=8H₂,O—CH₂), 2.7(3H,s,CH₃), 2.9–2.7(8H,n,CH₂CH₃ and CH₂CH₃), 1.3(6H,t,J=7Hz,CH₂CH₃)

EXAMPLE 15

6-(2Chlorophenyl)-3-(1-cyano-1-methylethoxycarbonyl)-7,11-dimethyl-2,3,4,5-tetrahydro-8H-pyrido[4',3':4,5]thieno[3,2-f][1,2,4]triazolo[4,3-a][1,4-diazepine

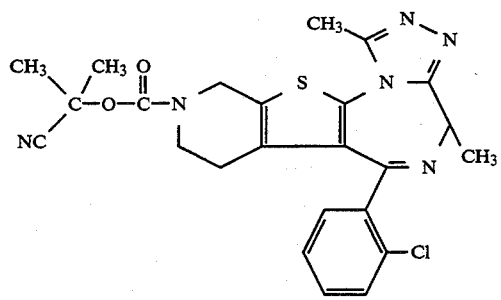

0.24 g of sodium hydride (60%) was added to a solution of 1.12 g of the compound obtained in Example 1 in N,N-dimethylformamide (3 ml) under ice-cooling conditions, followed by agitation for 30 minutes. Thereafter, 0.37 ml of methyl bromide was added to the solution and agitated under ice-cooling conditions for 30 minutes and then at room temperature for 1 hour. After completion of the reaction, water was added, followed by extraction with chloroform and drying with magnesium sulfate. The residue obtained after filtration and concentration was subjected to purification with silica gel column chromatography (elution solvent: chloroform:methanol=99:1), thereby obtaining 0.19 g of the intended compound.

¹H-NMR (90MHz, CDCl₃) δ: 1.76(s,6H), 1.80–2.20(m,2H), 2.10(d,3H), 2.66(s,3H), 3.0–3.9(m,2H), 4.24(q,1H), 4.3–4.9(m,2H), 7.35(m, 4H),

FABMS[M+H⁺] m/z: 495

EXAMPLES 16 TO 71

In the same manner as in the foregoing example, the following compounds were prepared.

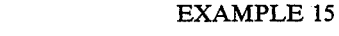

EXAMPLE 15

6-(2-Chlorophenyl)-3-(1-cyano-1-methylethoxycarbonyl)-8,8,11-trimethyl-2,3,4,5-tetrahydro-8H-pyrido[4',3':4,5]thieno[3,2-f][1,2,4-triazolo[4,3-a][1,4]diazepine

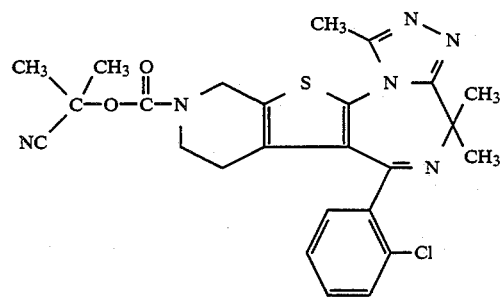

¹H-NMR (90MHz, CDCl₃) δ: 1.8(s,6H), 2.8(s,3H), 3.1(s,3H), 3.0–3.9(m,4H), 3.8(s,3H), 4.4–4.9(m,2H), 7.4(m,4H)

EXAMPLE 17

6-(2-Chlorophenyl)-3-cyclopropylmethylaminocarbonyl-11-methyl-2,3,4,5-tetrahydro-8H-pyrido[4',3':4,5]-thieno[3,2-f][1,2,4triazolo[4,3-a][1,4]diazepine

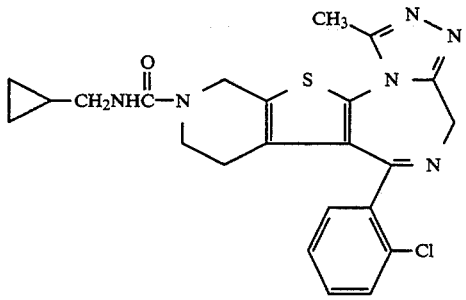

$^1$H-NMR (90MHz, CDCl$_3$) δ: 0.04–0.32(m,2H), 0.36–0.60(m,2H), 0.70–1.16(m,1H), 1.52–2.17(m,2H), 2.66(s,3H), 2.84–5.85(m,7H), 3.04(dd,J=6Hz,7Hz,2H), 7.32(m,4H)
FABMS(M+H$^+$) m/z:467

EXAMPLE 18

6-(2-Chlorophenyl)-3-(1-ethynylcyclohexylaminocarbonyl)-11-methyl-2,3,4,5-tetrahydro-8H-pyrido[4',3':4,5]thieno[3,2-f][1,2,4]triazolo[4,3-a][1,4]diazepine

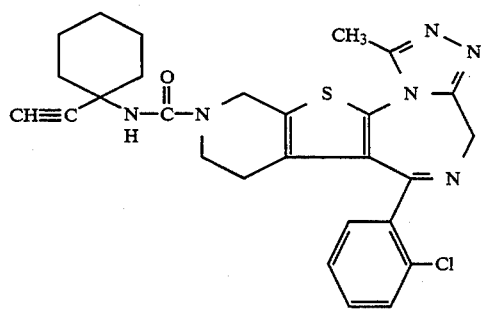

$^1$H-NMR (90MHz, CDCl$_3$) δ: 1.12–2.24(m,12H), 2.37(s,1H), 2.80–5.76(m,7H), 7.29(m,4H)
FABMS(M+H$^+$) m/z:519

EXAMPLE 19

6-(2-chlorophenyl)-3-(5-cyanopentylaminocarbonyl)-11-methyl-2,3,4,5-tetrahydro-8H-pyrido[4',3':4,5]-thieno[3,2-f][1,2,4]triazolo[4,3-a][1,4]diazepine

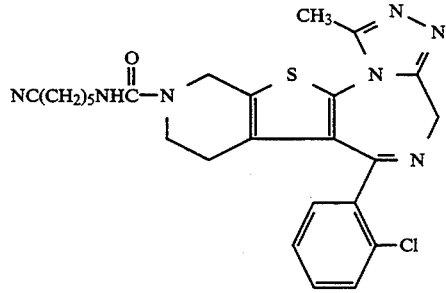

$^1$H-NMR (90MHz, CDCl$_3$) δ: 1.24–2.16(m,8H), 2.32(t,J=7Hz,2H), 2.81–5.68(m,9H), 7.29(m,4H)

FABMS(M+H$^+$) m/z:508

EXAMPLE 20

6-(2-Chlorophenyl)-3-(4-cyanophenylaminocarbonyl)-11-methyl-2,3,4,5-tetrahydro-8H-pyrido[4',3':4,5]-thieno[3,2-f][1,2,4triazolo[4,3-a][1,4]diazepine

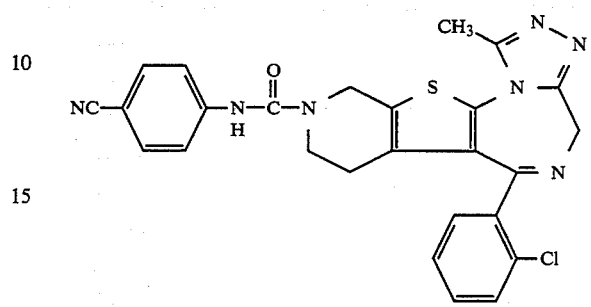

$^1$H-NMR (90MHz, CDCl$_3$) δ: 1.56–2.18(m,2H), 2.67(s,3H), 3.80–5.70(m,6H), 7.32(m,4H), 7.47(m,4H), 8.40(br,s,1H)
FABMS(M+H$^+$) m/z: 514

EXAMPLE 21

6-(2-Chlorophenyl)-3-(3-cyanopentylaminocarbonyl)-11-methyl-2,3,4,5-tetrahydro-8H-pyrido[4',3':4,5]-thieno[3,2-f][1,2,4]triazolo[4,3-a][1,4]diazepine

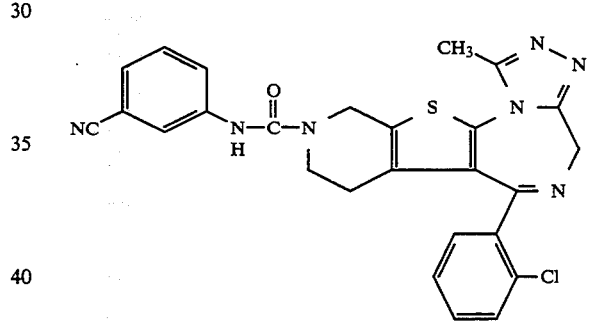

$^1$H-NMR (90MHz, CDCl$_3$) δ: 1.43–2.17(m,2H), 2.63(s,3H), 3.04–5.68(m,6H), 7.05–7.72(m,8H)
FABMS(M+H$^+$) m/z: 514

EXAMPLE 22

6-(2-Chlorophenyl)-3-(3-ethynylphenylaminocarbonyl)-11-methyl-2,3,4,5-tetrahydro-8H-pyrido[4',3':4,5]thieno[3,2-f][1,2,4]trizolo[4,3-a][1,4]diazepine

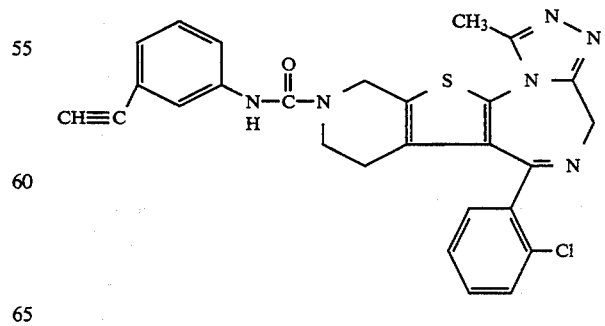

$^1$H-NMR (90MHz, CDCl$_3$) δ: 1.40–2.40(m,2H), 2.66(s,3H), 3.01(s,1H), 3.05–5.08(m,6H), 6.64(br,s,1H), 6.88–7.48(m,8H)

FABMS(M+H+) m/z: 513

EXAMPLE 23

6-(2-chlorophenyl)-11-methyl-3-(morpholin-4-yl)carbonyl-2,3,4,5-tetrahydro-8H-pyrido[4',3':4,5]thieno[3,2-f][1,2,4]triazolo[4,3-a][1,4]diazepine

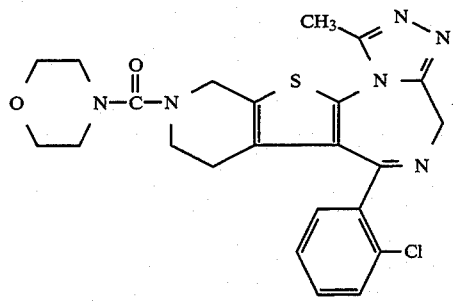

¹H-NMR (90MHz, CDCl₃) δ: 1.32–2.44(m,2H), 2.66(s,3H), 2.92–5.80(m,6H), 3.21(t,J=6Hz,4H), 3.63(t,J=6Hz,4H), 7.29(m,4H)
FABMS(M+H+) m/z: 483

EXAMPLE 24

6-(2-Chlorophenyl)-3-(1-ethynylcyclopentylaminocarbonyl)-11-methyl-2,3,4,5-tetrahydro-8H-pyrido[4',3':4,5]thieno[3,2-f][1,2,4]triazolo[4,3-a][1,4]diazepine

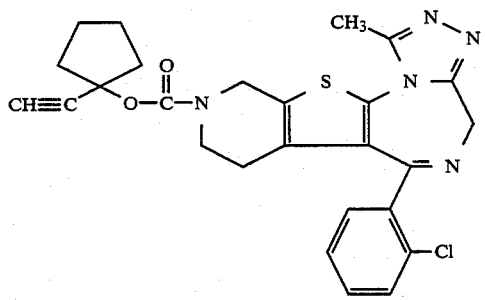

¹H-NMR (90MHz, CDCl₃) δ: 1.40–2.44(m,10H), 2.56(s,1H), 2.67(s,3H), 2.90–5.90(m,6H), 7.29(m,4H)
FABMS(M+H+) m/z: 506

EXAMPLE 25

6-(2-Chlorophenyl)-11-methyl-3-(phenylethylcarbonyl)-2,3,4,5-tetrahydro-8H-pyrido[4',3':4,5]-thieno[3,2-f][1,2,4]triazolo[4,3-a][1,4]diazepine

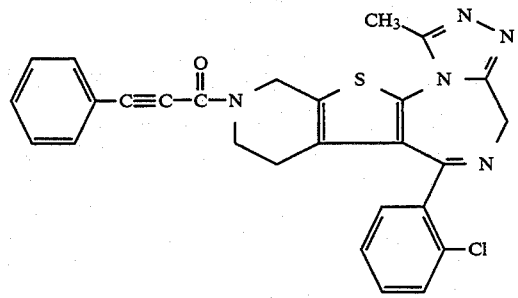

¹H-NMR (90MHz, CDCl₃) δ: 1.67–2.40(m,2H), 2.68(s,3H), 3.04–5.80(m,6H), 7.12–7.60(m,9H)
FABMS(M+H+) m/z: 498

EXAMPLE 26

6-(2-Chlorophenyl)-3-(1,1-dimethyl-2-propynyloxycarbonyl)-11-methyl-2,3,4,5-tetrahydro-8H-pyrido[4',3':4,5]thieno[3,2]-f][1,2,4]triazolo[4,3-a][1,4]diazepine

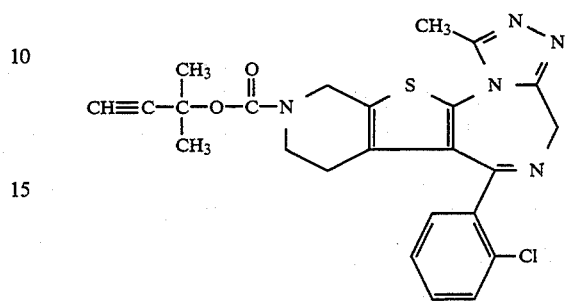

¹H-NMR (90 MHz, CDCl₃) δ: 1.40–2.18(m,2H), 1.68(s,6H), 2.53(s,1H), 2.67(s,3H), 2.90–5.76(m, 6H), 7.30(m,4H)
FABMS (M+H+) m/z:480

EXAMPLE 27

6-(2-Chlorophenyl)-11-methyl-3-(1-methyl-2-propynyloxycarbonyl)-2,3,4,5-tetrahydro-8H-pyrido[4',3':4,5]thieno[3,2-f][1,2,4]triazolo[4,3-a][1,4]diazepine

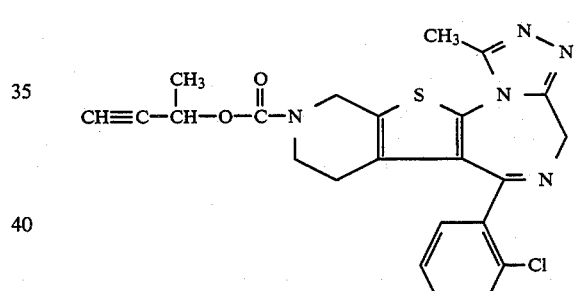

¹H-NMR (90 MHz, CDCl₃) δ: 1.38–2.32(m,2H), 1.50(d,J=7Hz,3H), 2.45(d,J=2Hz,1H), 2.66(s,3H), 2.88–5.70(m,6H), 5.34(dq,J=2Hz,7Hz,1H), 7.29(m,4H)
FABMS (M+H+) m/z: 466

EXAMPLE 28

6-(2-Chlorophenyl)-11-methyl-3-(1-methyl-3-butynyloxycarbonyl)-2,3,4,5-tetrahydro-8H-pyrido[4',3':4,5]thieno[3,2-f][1,2,4]triazolo[4,3-a][1,4]diazepine

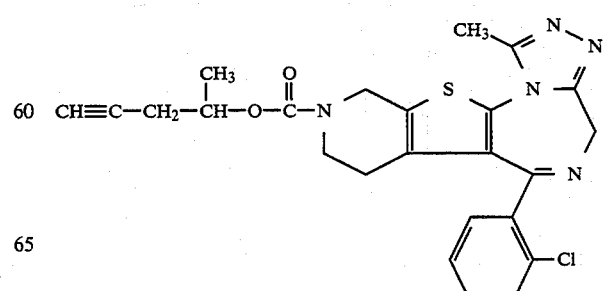

¹H-NMR (90 MHz, CDCl₃) δ: 1.30(d,J=7Hz,3H), 1.50–2.60(m,5H), 2.66(s,3H), 2.88–5.72(m,7H), 7.29(m,4H)

FABMS (M+H⁺) m/z:480

EXAMPLE 29

6-(2-Chlorophenyl)-11-methyl-3-(2-pentyloxycarbonyl)-2,3,4,5-tetrahydro-8H-pyrido[4',3':4,5]-thieno[3,2-f][1,2,4]triazolo[4,3-a][1,4]diazepine

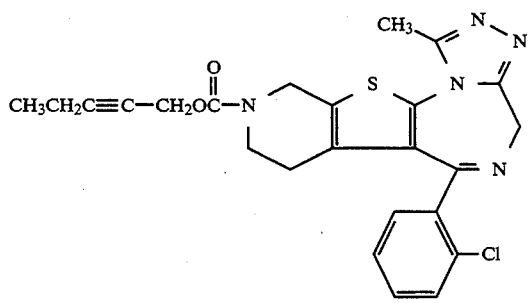

¹H-NMR(90 MHz, CDCl₃) δ: 1.13(d,J=7Hz,3H), 1.54–2.36(m,2H), 2.25(tq,J=2Hz, 7Hz, 2H), 2.67(s,3H), 284–5.76 (m,6m), 4.66(t,J=2Hz,2H), 7.30(m,4H)

FABMS (M+H⁺) m/z:480

EXAMPLE 30

6-(2-Chlorophenyl)-11-methyl-3-(3-pentynyloxycarbonyl)-2,3,4,5-tetrahydro-8H-pyrido[4',3';4,5]-thieno[3,2-f][1,2,4]triazolo[4,3-a][1,4]diazepine

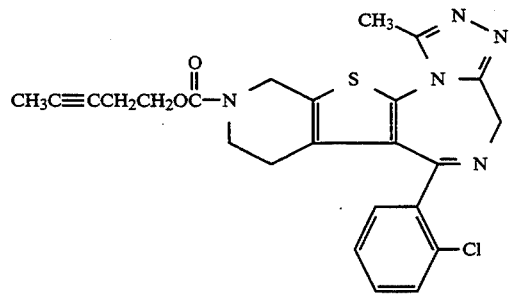

¹H-NMR (90 MHz, CDCl₃) δ: 1.50–2.20(m,2H), 1.74(t,J,=2Hz,3H), 2.42(m,2H), 2.66(s,3H), 2.90–5.70(m,6H), 4.11(t,J=7Hz,2H), 7.30(m,4H)

FABMS (M+H⁺) m/z:480

EXAMPLE 31

6-(2-Chlorophenyl)-3-[2-(imidazol-1-yl)ethoxycarbonyl]-11-methyl-2,3,4,5-tetrahydro-8H-pyrido[4',3':3,5-]thieno[3,2-f][1,2,4]triazolo[4,3-a][1,4]diazepine

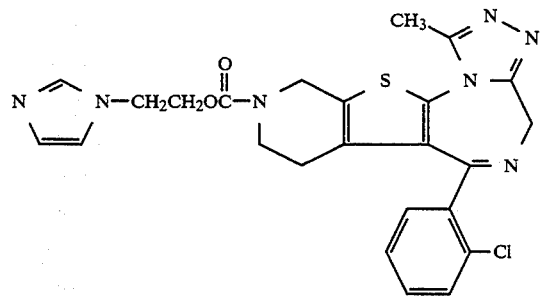

¹H-NMR(90 MHz, CDCl₃) δ: 1.50–2.19(m,2H), 2.66(s,3HH), 2.80–5.80(m,10H), 6.70–6.92(m,1H), 6.92–7.06(m,1H), 7.12–7.54(m, 1H), 7.30(m,4H)

FABMS (M+H⁺) m/z:508

EXAMPLE 32

6-(2-Chlorophenyl)-11-methyl-3-(2,3,5,6-tetrahydropyran-4-yl)oxycarbonyl-2,3,4,5-tetrahydro-8H-pyrido[4',3':4,5]thieno[3,2-f][1,2,4]triazolo[4,3-a][1,4-diazepine

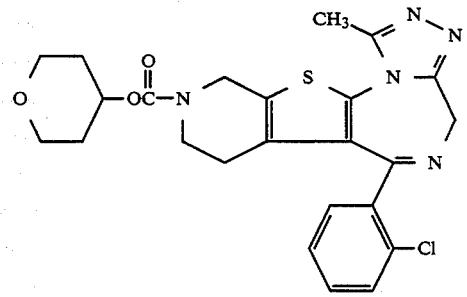

¹H-NMR(90 MHz, CDCl₃) δ: 1.40–2.12(m,6H), 2.67(s,3H), 2.84–5.68(m,11H), 7.29(m,4H)

FABMS (M+H⁺) m/z:498

EXAMPLE 33

6-(2-Chlorophenyl)-3-(5-hexynyloxycarbonyl)-11-methyl-2,3,4,5-tetrahydro-8H-pyrido[4',3':4,5]-thieno[3,2-f][1,2,4]triazolo[4,3-a][1,4]diazepine

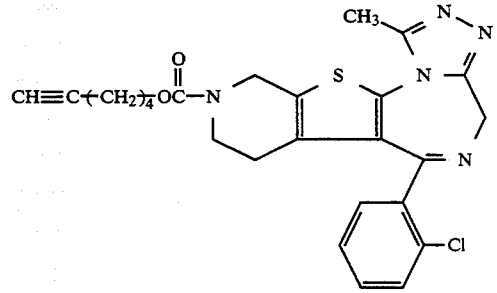

¹H-NMR(90 MHz, CDCl₃) δ: 1.20–2.32(m,6H), 1.94(t,J=2Hz,1H), 2.21(dt,J=2Hz,7Hz,2H), 2.66(s,3H), 2.84–5.76(m,6H), 7.28(m,4H)

FABMS (+H⁺) m/z:494

EXAMPLE 34

6-(2-Chlorophenyl)-3-(3-cyano-1-oxopropyl)-11-methyl-2,3,4,5-tetrahydro-8H-pyrido[4',3':4,5]thieno[3,2-f][1,2,4]triazolo[4,3-a][1,4]diazepine

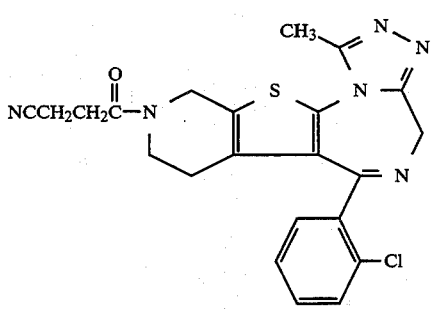

¹H-NMR(90 MHz, CDCl₃) δ: 1.16–2.38(m,2H), 2,42–2.79(m,4H), 2.67(s,3H), 3.20–5.72(m,6H), 7.31(m,4H)
FABMS (M+H⁺) m/z:451

EXAMPLE 35

6-(2-Chlorophenyl)-3-(2-cyano-1-oxoethyl)-11-methyl-2,3,4,5-tetrahydro-8H-pyrido[4',3':4,5]thieno[3,2-f][1,2,4]triazolo[4,3-a][1,4]diazepine

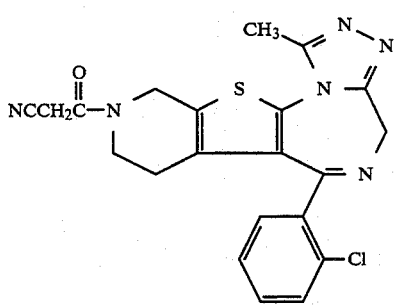

¹H-NMR(90 MHz, CDCl₃) δ: 1.60–2.35(m,2H), 2.66(s,3H), 3.20–5.76(m,8H), 7.30(m,4H)
FABMS (M+H⁺) m/z:437

EXAMPLE 36

6-(2-Chlorophenyl)-3-(3-cyanopropoxycarbonyl)-11-methyl-2,3,4,5-tetrahydro-8H-pyrido[4',3':4,5]-thieno[3,2-f][1,2,4]triazolo[4,3-a][1,4]diazepine

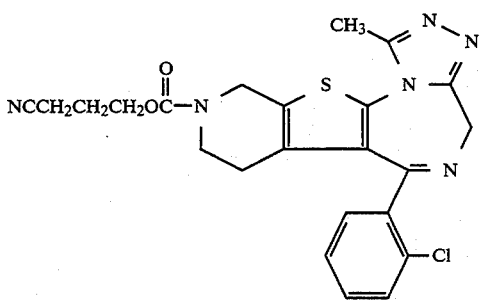

¹H-NMR(90 MHz, CDCl₃) δ: 1.41–1.80(m,2H), 1.80–2.17(m,2H), 2.22–2.52(m2H), 2.66(s,3H), 2.86–5.76(m,6H), 4.20(t,t=7Hz,2H), 7.30 (m,4H)
FABMS (M+H⁺) m/z:481

EXAMPLE 37

6-(2-Chlorophenyl)-11-methyl-3-(1-oxo-4-pentyl)-2,3,4,5-tetrahydro-8H-pyrido[4',3',4,5]thieno[3,2-f][1,2,4]triazolo[4,3-a][1,4]diazepine

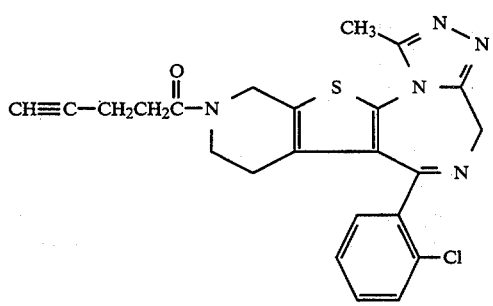

¹H-NMR(90 MHz, CDCl₃) δ: 1.54–2.18(m,2H), 1.96(m,1H), 2.44–2.65(m,4H), 2.71(s,3H), 2.88–5.76(m,6H), 7.42(m,4H)
FABMS (M+H⁺) m/z:450

EXAMPLE 38

6-(2-Chlorophenyl)-11-methyl-3-(1-propargylpiperidin-4-yl)oxycarbonyl-2,3,4,5-tetrahydro-8H-pyrido[4',3':4,5]thieno[3,2-f][1,2,4]triazolo[4,3-a][1,4]diazepine

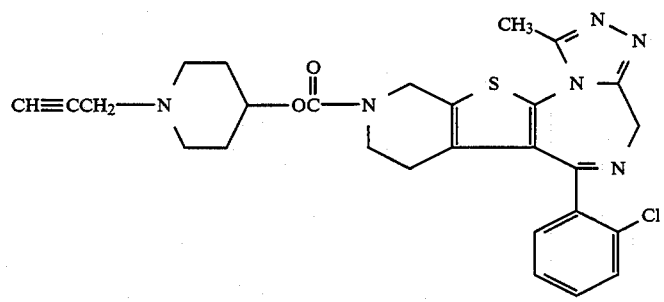

¹H-NMR(90 MHz, CDCl₃) δ: 1.4–2.9(m,11H), 2.25(t,1H), 2.7(s,3H), 3.3(d,2H), 3.0–3.9(m,2H), 4.0–4.9(m,1+2H), 5.4–5.8(m,1H), 7.4(m,4H)

MS m/z(Pos. FD):535

EXAMPLE 39

6-(2-Chlorophenyl)-3-cyclohexyloxycarbonyl-11-methyl-2,3,4,5-tetrahydro-8H-pyrido[4′,3′:4,5]thieno[3,2-f][1,2,4]triazolo[4,3-a][1,4]diazepine

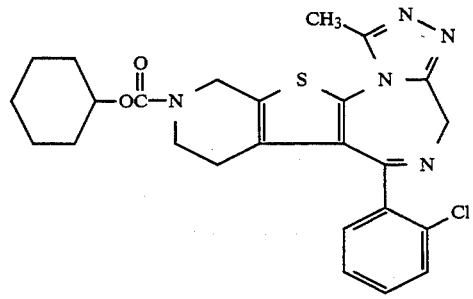

$^1$H-NMR(90 MHz, CDCl$_3$) δ: 1.2–2.3(m,12H), 2.7(s,3H), 3.0–4.0(m,2H), 4.0–4.8(m,1+2H), 5.4–5.8(m,1H), 7.4(m,4H)
MS m/z(Pos. FAB):496

EXAMPLE 40

6-(2-Chlorophenyl)-3-cyclohexylethoxycarbonyl-11-methyl-2,3,4,5-tetrahydro-8H-pyrido[4′,3′:4,5]thieno[3,2-f][1,2,4-triazolo[4,3-a][1,4]diazepine

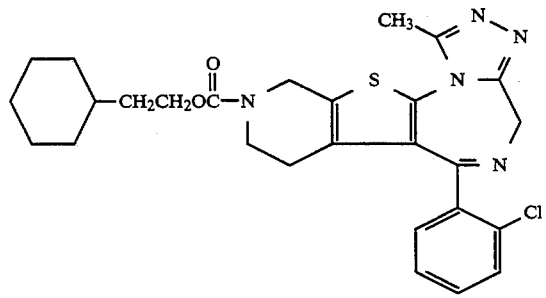

$^1$H-NMR(90 MHz, CDCl$_3$) δ: 0.6–2.7(m,17H), 2.7(s,3H), 3.0–4.0(m,2H), 4.9–4.4(m,1+2H), 4.4–4.8(m,2H), 5.4–5.8(m,1H), 7.4(m,4H)
MS m/z(Pos. FAB):538

EXAMPLE 41

6-(2-Chlorophenyl)-3-cyclopropylmethoxycarbonyl-11-methyl-2,3,4,5-tetrahydro-8H-pyrido[4′,3′:4,5]-thieno[3,2-f][1,2,4]triazolo[4,3-a][1,4]diazepine

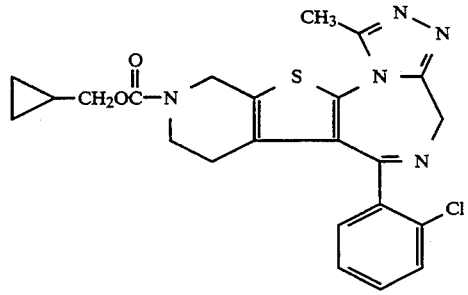

$^1$H-NMR(90 MHz, CDCl$_3$) δ: 0.2–2.0(m,7H), 2.7(s,3H), 3.0–4.0(m,2H), 3.8–4.0(d,2H), 4.4–4.8(m,1+2H), 5.4–5.8(m,1H), 7.4(m,4H)

MS m/z(Pos. FAB):468

EXAMPLE 42

6-(2-Chlorophenyl)-3-cyclohexylmethoxycarbonyl-11-methyl-2,3,4,5-tetrahydro-8H-pyrido[4′,3′:4.5]-thieno]3,2-f][1,2,4]triazolo[4,3-a][1,4]diazepine

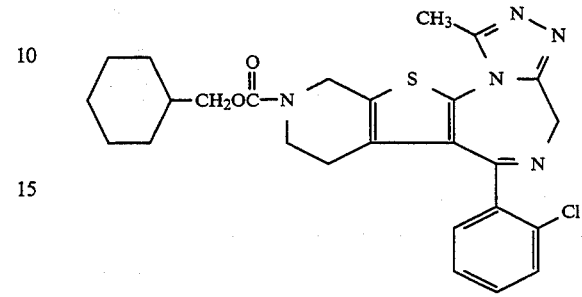

$^1$H-NMR(90 MHz, CDCl$_3$) δ: 0.8–2.2(m,13H), 2.7(s,3H), 3.0–4.0(m,2H), 3.7–4.0(d,2H), 4.1–4.8(m,1+2H), 5.4–5.8(m,1H), 7.4(m,4H)
MS m/z(Pos, FAB):510

EXAMPLE 43

6-(2-Chlorophenyl)-11-methyl-3-(4-pyridylcarbonyl)-2,3,4,5-tetrahydro-8H-pyrido[4′,3′:4.5]thieno[3,2-f][1,2,4]triazolo[4,3-a][1,4]diazepine

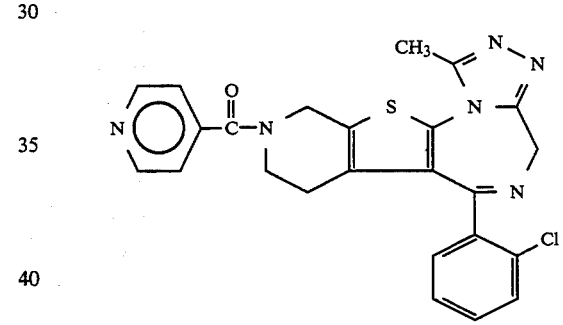

$^1$H-NMR(90 MHz, CDCl$_3$) δ: 1.4–2.5(m,2H), 2.67(s,3H), 3.1–3.75(m,2H), 3.9–5.8(m,4H), 7.0–7.7(m,6H), 8.4–8.8(m,2H)
MS m/z(Pos. FAB):475

EXAMPLE 44

6-(2-Chlorophenyl)-3-cyclohexylmethylcarbonyl-11-methyl-2,3,4,5-tetrahydro-8H-pyrido[4′,3′:4,5]-thieno[3,2-f][1,2,4]triazolo[4,3-a][1,4]diazepine

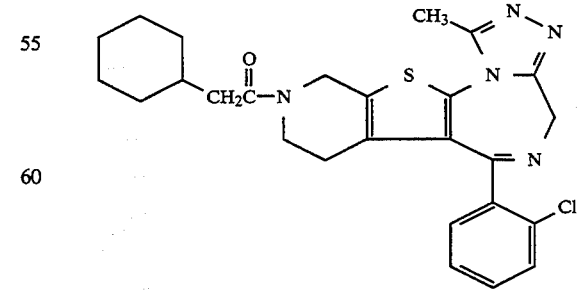

$^1$H-NMR(90 MNz, CDCl$_3$) δ: 0.6–2.4(m,13H), 2.16(d, J=6.5Hz, 2H), 2.67(s,3H), 2.8–5.9(m,6H), 7.1–7.6(m,4H)

MS m/Z(Pos. Fab):494(M+H)+

EXAMPLE 45

6-(2-Chlorophenyl)-3-cyclohexanecarbonyl-11-methyl-2,3,4,5-tetrahydro-8H-pyrido[4',3':4,5]thieno[3,2-f][1,2,4-triazolo[4,3-a][1,4]diazepine

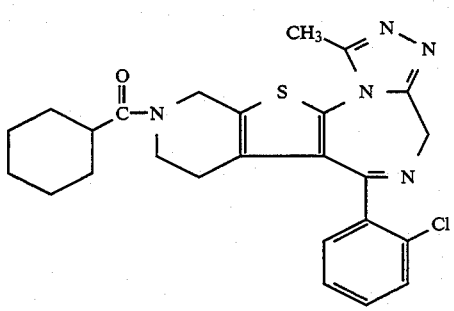

¹H-NMR(90 MHz, CDCl₃) δ: 0.7–2.7(m,13H), 2.67(s,3H), 2.8–5.8(m,6H), 7.1–7.6(m,4H)
MS m/z(Pos. FAB):480(M+H)+

EXAMPLE 46

6-(2-Chlorophenyl)-11-methyl-3-(3-pyridylcarbonyl)-2,3,4,5-tetrahydro-8H-pyrido[4',3':4,5]thieno[3,2-f][1,2,4]triazolo[4,3-a][1,4]diazepine

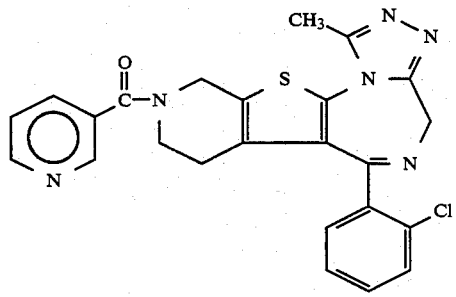

¹H-NMR(90 MHz, CDCl₃) δ: 1.4–2.6(m,2H), 2.66(s,3H), 2.8–6.0(m,6H), 7.1–8.0(m,6H), 8.4–8.8(m,2H)
MS m/z(Pos. FAB): 475(M+H)+

EXAMPLE 47

3-[4'-(morpholin-4-yl-sulfonyl)phenylaminocarbonyl]-6-(2-chlorophenyl)-11-methyl-2,3,4,5-tetrahydro-8H-pyrido[4',3':4,5]thieno[3,2-f][1,2,4]triazolo[4,3-a][1,4]diazepine

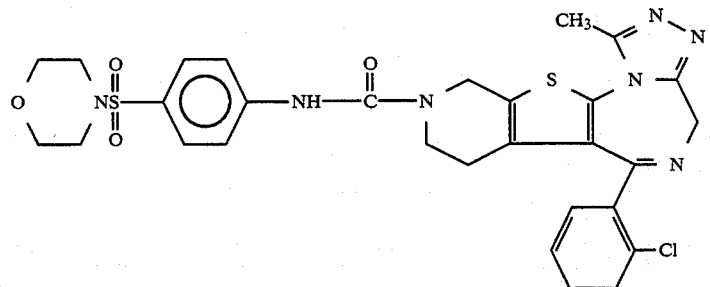

¹H-NMR(90 MHz, CDCl₃) δ: 1.80–2.20(m,4H), 2.63(s,3H), 2.80–3.08(m,4H), 3.24–3.90(m, 9H), 4.60–4.90(m,2H), 7.20–7.42(m,4H), 7.45–7.68(m,4H), 7.75(brs.1H)
MS:m/z 638

EXAMPLE 48

3-[4'-(N-piperidinosulfonyl)phenylaminocarbonyl]-6-(2-chlorophenyl)-11-methyl-2,3,4,5-tetrahydro-8H-pyrido[4',3':4,5]thieno[3,2-f][1,2,4]triazolo[4,3-a][1,4]diazepine

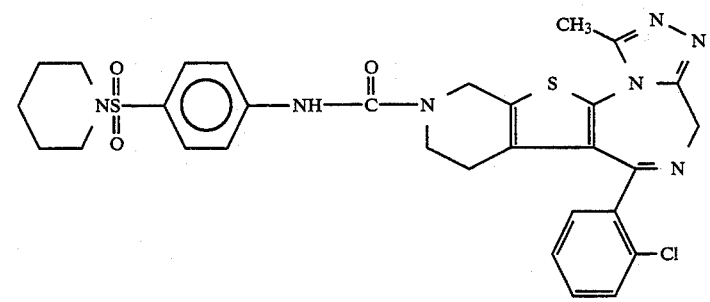

¹H-NMR(90 MHz, CDCl₃) δ: 1.10–2.30(m,10H), 2.64(s,3H), 2.75–3.10(m,4H), 3.30–4.30(m,2H), 4.60–4.92(m,2H), 7.15–7.40(m,4H), 7.42–7.60(m,4H), 7.72(brs,1H)
MS:m/z 636

EXAMPLE 49

3-[4'-(N-imidazolsulfonyl)phenylaminocarbonyl]-6-(2-chlorophenyl)-11-methyl-2,3,4,5-tetrahydro-8H-pyrido[4',3':4,5]thieno[3,2-f][1,2,4]triazolo[4,3-a][1,4]diazepine

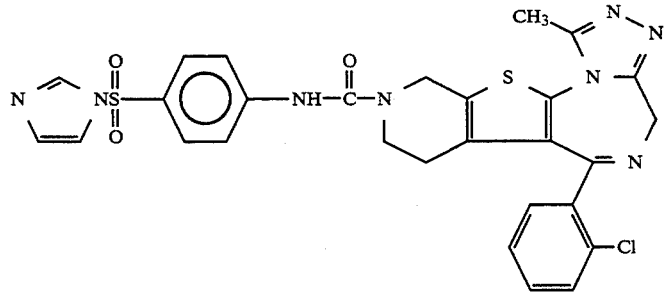

$^1$H-NMR(90 MHz, CDCl$_3$) δ: 1.60–2.40(m,4H), 2.70(s,3H), 3.75–4.30(m,2H), 4.40–5.00(m,2H), 7.00–7.50(m,12H)
MS:m/z 619

EXAMPLE 50

3-[4'-(sulfamoyl)phenylaminocarbonyl]-6-(2-chlorophenyl)-11-methyl-2,3,4,5-tetrahydro-8H-pyrido[4',3':4,5]thieno[3,2-f][1,2,4]triazolo[4,3-a][1,4]diazepine

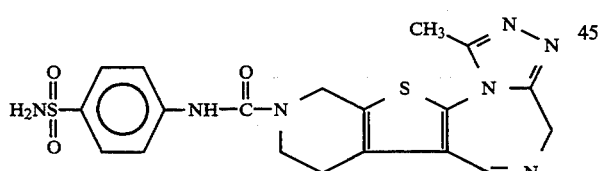

$^1$H-NMR(90 MHz, CDCl$_3$) δ: 1.40–2.20(m,4H), 2.62(s,3H), 3.60–4.40(m,2H), 5.10–5.50(m,2H), 7.10(s2H), 7.30–7.60(m4H), 7.62(ABq,4H,J=9.0Hz) 8.95(s,1H)
MS:m/z 568

EXAMPLE 51

3-[4'-(N,N'-diethylaminosulfonyl)phenylaminocarbonyl]-6-(2-chlorophenyl)-11-methyl-2,3,4,5-tetrahydro-8H-pyrido[440,3':4,5]thieno[3,2-f][1,2,4]triazolo[4,3-a][1,4diazepine

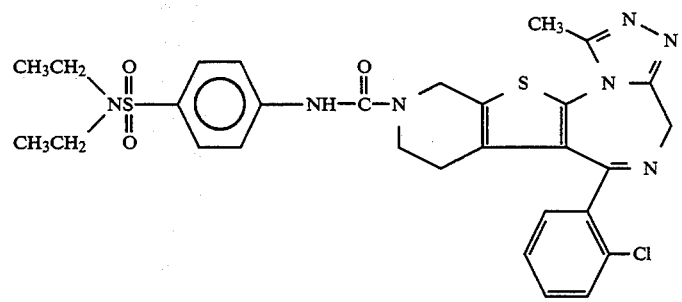

$^1$H-NMR(90 MHz, CDCl$_3$) δ: 1.10(t, 6h,J=7.2H), 1.70–2.30(m,4H), 2.62(s,3H), 3.16(q,4H,J=7.2Hz), 3.40–4.20(m,2H), 3,55–3.60(m,2H), 7.18–74.0(m,4H), 7.54(ABq,4H,J=9.0Hz), 7.70(s,1H)
MS:m/z 624

EXAMPLE 52

3-[4'-(N-cyclohexylaminosulfonyl)phenylaminocarbonyl]-6-(2-chlorophenyl)-11-methyl-2,3,4,5-tetrahydro-8H-pyrido[4',3':4,5]thieno[3,2-f][1,2,4]triazolo[4,3-a][1,4]-diazepine

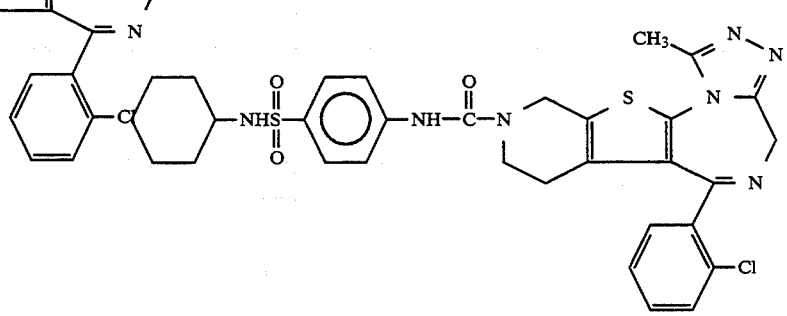

$^1$H-NMR(90 MHz, CDCl$_3$) δ: 0.80–2.20(m,14H), 2.64(s,3H), 2.80–4.30(m,3H), 4.60–4.30(m,3H), 4.60–4.90(m,2H), 5.05(d,1H,J=7.2Hz), 7.20–7.40(m,4H), 7.56(ABq,4H,J=9.0Hz), 7.76(s,1H)
MS:m/z 650

EXAMPLE 53

3-[4'-(2''-pyridylmethylaminosulfonyl)phenylaminocarbonyl]-6-(2-chlorophenyl)-11-methyl-2,3,4,5-tetrahydro-8H-pyrido[4',3':4,5]thieno[3,2-f][1,2,4]triazolo[4,3-a][1,4]diazepine

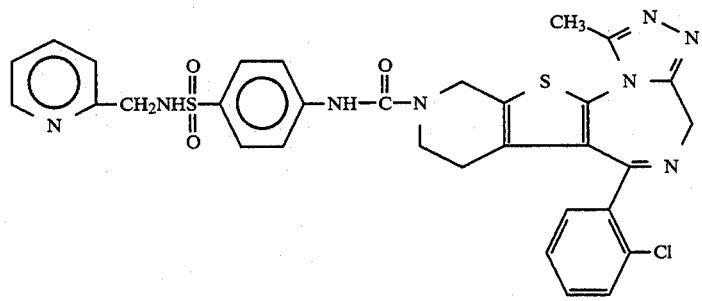

$^1$H-NMR(90 MHz, CDCl$_3$) δ: 1.60–2.20(m,4H), 2.72(s,3H), 3.60–4.50(m,6H), 6.50–6.72(m,2H), 7.00–7.70(m,11H), 8.11–8.28(m,1H)
MS m/z:659

EXAMPLE 54

3-[3-(N-piperidinosulfonyl)-propyloxycarbonyl]-6-(2-chlorophenyl)-11-methyl-2,3,4,5-tetrahydro-8H-pyrido[4',3':4,5]thieno[3,2-f][1,2,4]triazolo[4,3-a][1,4-diazepine

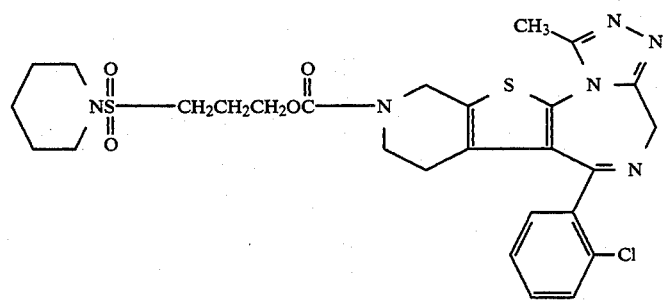

$^1$H-NMR(90 MHz, CDCl$_3$) δ: 1.40–2.30(m,12H), 2.70(s,3H), 2.95(t2, H,J=7.2Hz), 3.10–3.40(m,4H), 3.50–4.20(m,2H), 4.22(t2,H,J=7.2Hz), 4.42–4.82(m,2H), 7.20–7.50(m,4H)
MS:m/z 603

EXAMPLE 55

3-[3-(N-morpholinosulfonyl)-propyloxycarbonyl]-6-(2-chlorophenyl)-11-methyl-2,3,4,5-tetrahydro-8H-pyrido[4',3':4,5]thieno]3,2-f][1,2,4]triazolo[4,3-a][1,4]diazepine

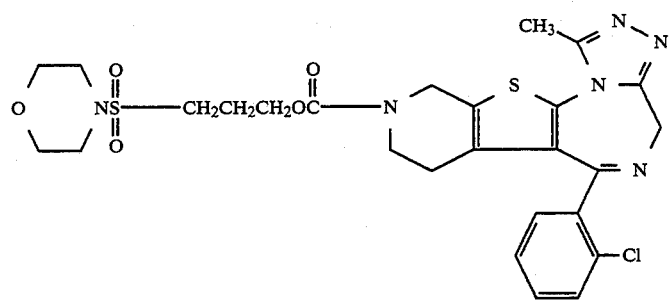

$^1$H-NMR(90 MHz, CDCl$_3$) δ: 1.60–2.40(m,6H), 2.70(s,3H), 2.98(t,2H,J=7.2Hz), 3.60–3.90(m,4H), 2,80–4.40(m,2H), 4.22(t,2H,J=7.2Hz), 4.40–4.84(m,2H), 7.20–7.50(m,4H)
MS:m/z 605

EXAMPLE 56

3-[4'-(N-morpholinosulfonyl)phenyloxycarbonyl]-6-(3-chlorophenyl)-11-methyl-2,3,4,5-tetrahydro-8H-pyrido[4',3':4.5]thieno[3,2-f][1,2,4-triazolo[4,3-a][1,4]diazepine

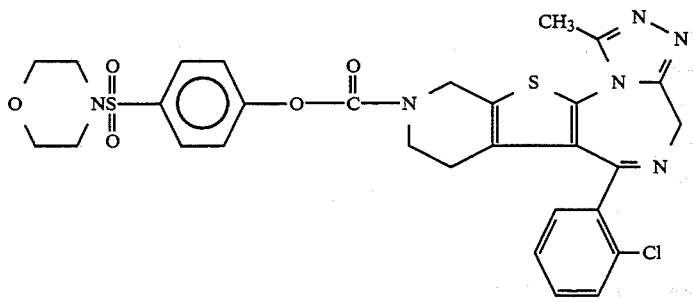

$^1$H-NMR(90 MHz, CDCl$_3$) δ: 1.60–2.40(m,4H), 2.74(s,3H), 2.80–3.10(m,4H), 3.60–3.80(m,4H), 3.10–5.10(m,4H), 4.90–7.60(m,8H)
MS:m/z 639

EXAMPLE 57

6-(2-Chlorophenyl)-3-(2-cyanoethylmethylamino)carbonyl-11-methyl-2,3,4,5-tetrahydro-8H-pyrido[4',3':4,5]thieno[3,2-f][1,2,4]triazolo[4,3-a][1,4]diazepine

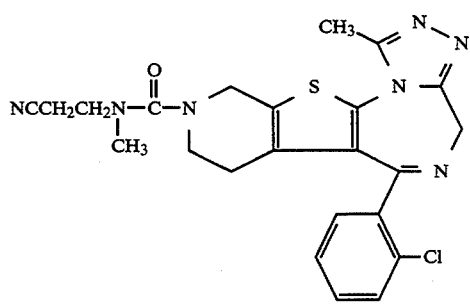

$^1$H-NMR(90 MHz, CDCl$_3$) δ: 1.57–2.22(m,2H), 2.61(t,J=7Hz,2H), 2.67(s,3H), 2.94(s,3H), 3.00–5.80(m,6H), 3.43(t,J=7Hz,2H), 7.31(m,4H)
FABMS(M+H+) m/z: 480

EXAMPLE 58

6-(2-Chlorophenyl)-3-(1-ethynyl-1-cyclohexyloxy-1-carbonyl-11-methyl-2,3,4,5-tetrahydro-8H-pyrido[4',3':4,5]thieno[3,2-f][1,2-triazolo[4,3-a][1,4]diazepine

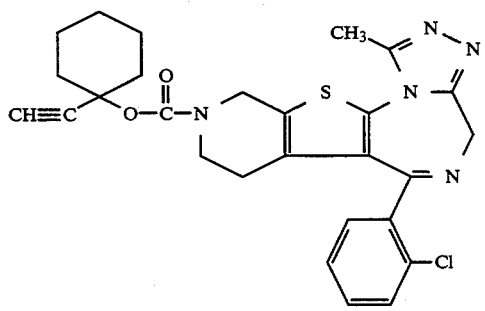

$^1$H-NMR(90 MHz, CDCl$_2$) δ: 1.04–2.35(m,12H), 2.59(s,1H), 2.67(s,3H), 2.78–5.78(m,6H), 7.30(m,4H)
FABMS(M+H+) m/z: 520

EXAMPLE 59

6-(2-Chlorophenyl)-11-methyl-3-(1-phenyl-2-propynyloxycarbonyl)-2,3,4,5-tetrahydro-8H-pyrido[4',3':4.5]thieno[3,2-f][1,2,4]triazolo[4,3-a][1,4]diazepine

$^1$H-NMR(90 MHz, CDCl$_3$) δ: 1.63–2.30(m,2H), 2.57(d,J=2Hz,1H), 2.65(s,3H), 2.97–5.71(m,6H), 6.35(d,J=2Hz,1H), 7.11–7.64(m,9H)
FABMS(M+H+) m/z: 528

EXAMPLE 60

6-(2-Chlorophenyl)-3-(2-cyanoethoxy)carbonyl-11-methyl-2,3,4,5-tetrahydro-8H-pyrido[4',3':4,5]-thieno[3,2-f][1,2,4]triazolo[4,3-a][1,4]diazepine

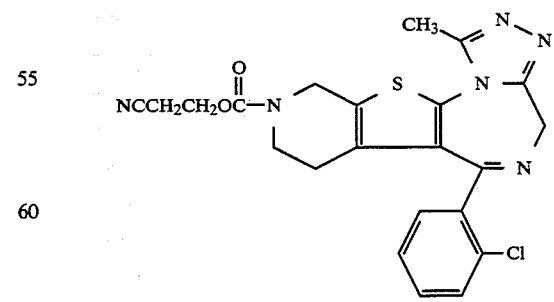

$^1$H-NMR(90 MHz, CDCl$_3$) δ: 1.40–2.34(m,2H), 2.66(s,3H), 2.70(t,J=7Hz,2H), 2.79–5.76(m,6H), 4.28(t,J=7Hz,2H), 7.30(m,4H)
FABMS(M+H+) n/z: 467

EXAMPLE 61

6-(2-Chlorophenyl)-11-methyl-3-(2-propynyl)aminocarbonyl-2,3,4,5-tetrahydro-8H-pyrido[4',3':4.5]thieno[3,2-f][1,2,4]triazolo[4,3-a][1,4diazepine

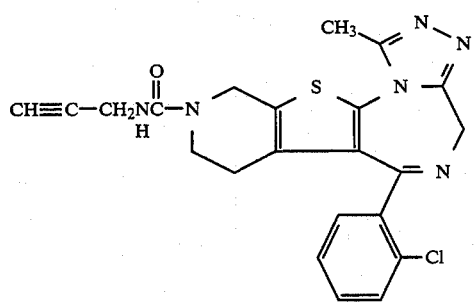

¹H-NMR(90 MHz, CDCl₃) δ: 1.56–2.08(m,2H), 2.19(d,J=2Hz,1H), 2.65(s,3H), 2.96–5.70(dd,J=2Hz,7Hz,6H), 3.98(dd,J=2Hz,7Hz,2H), 4.83(t,J=7Hz,1H), 7.28(m,4H))

FABMS(M+H+) m/z: 541

EXAMPLE 62

3-(2-Butynyloxycarbonyl)-6-(2-chlorophenyl)-11-methyl-2,3,4,5-tetrahydro-8H-pyrido[4',3':4,5]thieno[3,2-f][1,2,4]triazolo[4,3-a][1,4]diazepine

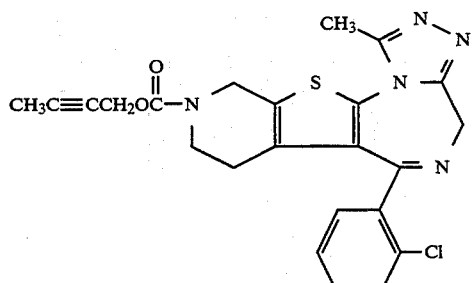

¹H-NMR(90 MHz, CDCl₃) δ: 1.43–2.15(m,2H), 1.84(t,J=2Hz,3H), 2.66(s,3H), 2.80–5.74(m,6H), 4.64(q,J=2Hz,2H), 7.30(m,4H)

FABMS(M+H+) m/Z: 466

EXAMPLE 63

6-(2-Chlorophenyl)-11-methyl-3-[2-pyridyl)ethylaminocarbonyl)]-2,3,4,5-tetrahydro-8H-pyrido[4',3':4,5]thieno[3,2-f][1,2,4]triazolo[4,3-a][1,4]diazepine

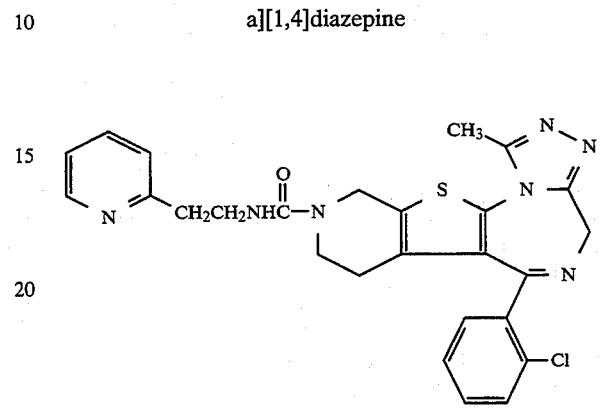

¹H-NMR(90 MHz, CDCl₃) δ: 1.46–2.25(m,2H), 2.65(s,3H), 2.76–5.76 (m,6H), 2.92(t,J=7Hz,2H), 3.42–3.68(m,2H), 5.95–6.24(m,1H), 6.93–7.39(m,6H), 7.40–7.66(m,1H), 8.25–8.40(m,1H)

MS m/z: 517

EXAMPLE 84

6-(2-Chlorophenyl)-3-[2-(morpholin-4-yl)ethylaminocarbonyl)]-11-methyl-2,3,4,5-tetrahydro-8H-pyrido[4',3':4,5]thieno[3,2-f][1,2,4]triazolo[4,3-a][1,4]diazepine

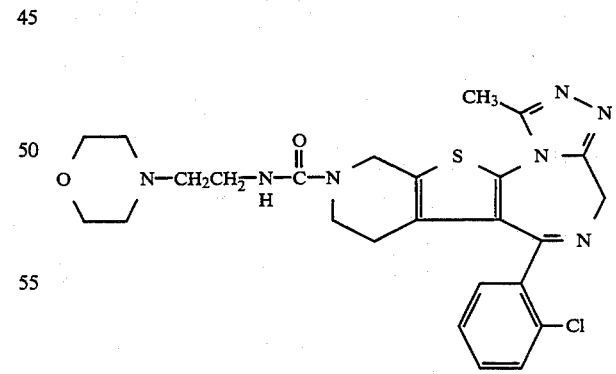

¹H-NMR(90 MHz, CDCl₃) δ: 1.54–2.20(m, 2H), 2.30–258 (m,6H), 2.67(s,3H), 2.88–5.80(m, 6H), 3.17–3.42(m,2H), 3.55–3.74(m,4H), 5.03–5.19(m,1H), 7.30(m,4H)

MS m/z: 525

EXAMPLE 65

6-(2-Chlorophenyl)-3-[4-(morpholin-4-yl-carbonyloxy)-2-butynyloxycarbonyl]-11-methyl-2,3,4,5-tetrahydro-8H-pyrido[4',3':4,5]thieno[3,2-f][1,2,4]triazolo[4,3-a][1,4]diazepine

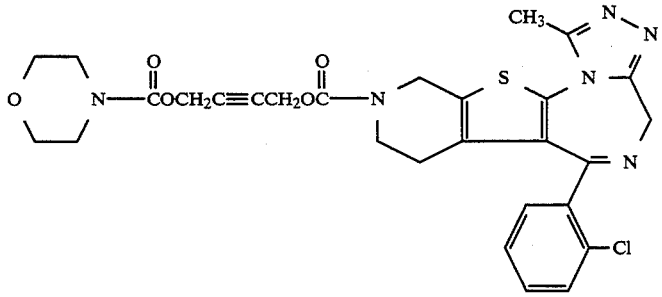

¹H-NMR(90 MHz, CDCl₃) δ: 1.55–2.28(m,2H), 2.66(s,3H), 2.87–5.75(m,6H), 3.34–3.54(m,4H), 3.54–3.72(m,4H), 4.75 (s,4H), 7.30(s,4H)
MS m/z: 594

EXAMPLE 66

6-(2-Chlorophenyl)-11-methyl-3-[4-(pyridin-2-yl-methylaminocarbonyloxy)-2-butynyloxycarbonyl]-2,3,4,5-tetrahydro-8H-pyrido[4',3':4,5]thieno[3,2-f][1,2,4]triazolo[4,3-a][1,4]diazepine

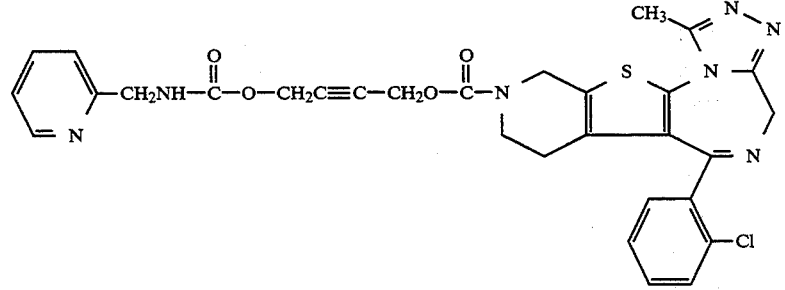

¹H-NMR(90 MHz, CDCl₃) δ: 1.6–2.2(m,2H), 2.70(s,3H), 3.0–5.75(m, 6H), 4.46(d,J=5Hz,2H), 4.72(s,4H), 5.90–6.20(m,1H), 7.1–7.6(m,6H), 7.5–7.9(m1H), 8.40–8.70(m,1H)
MS m/z: 615

EXAMPLE 67

6-(2-Chlorophenyl)-11-methyl-3-(4-pentynyloxycarbonyl)-2,3,4,5-tetrahydro-8H-pyrido[4',3':4,5]thieno[3,2-f][1,2,4]triazolo[4,3-a][1,4]diazepine

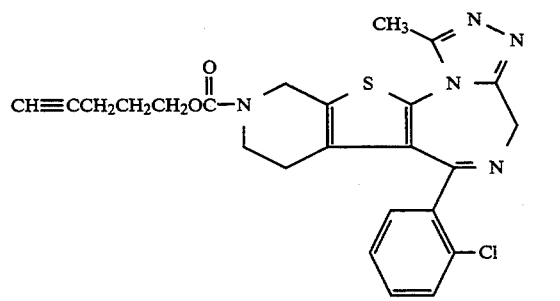

¹H-NMR (90 MHz, CDCl₃) δ: 1.52–2.08(m, 4H), 1.92(t,J=2Hz,1H), 2.08–2.40(m,2H), 2.66(s,3H), 2.84–5.72(m,6H), 4.17(t,J=7Hz,2H), 7.29(m,4H)
MS m/z: 479

EXAMPLE 68

6-(2-Chlorophenyl)-11-methyl-3-(2-propynyloxycarbonyl)-2,3,4,5-tetrahydro-8H-pyrido[4',3':4,5]thieno[3,2-f][1,2,4]triazolo[4,3-a][1,4]diazepine

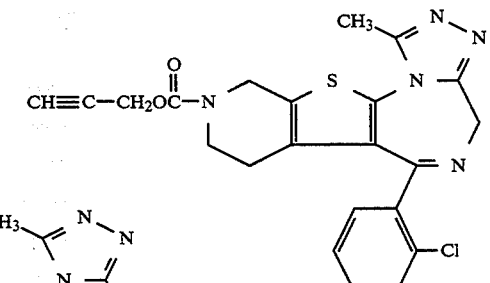

¹H-NMR(90 MHz, CDCl₃) δ: 1.68–2.15(m,2H), 2.50(t,J=3Hz,1H), 2.62(s,3H), 2.85–5.79(m,6H), 4.65(d,J=3Hz,2H), 7.40(m,4H)
MS m/z: 451

EXAMPLE 69

6-(2-Chlorophenyl)-11-methyl-3-[2-(pyridin-2-yl)-ethoxycarbonyl]-2,3,4,5-tetrahydro-8H-pyrido[4′,3′:4.5]thieno[3,2-f][1,2,4]triazolo[4,3-a][1,4-diazepine

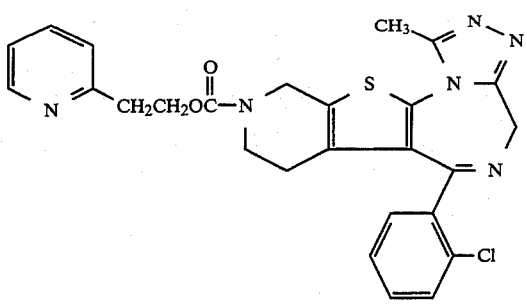

¹H-NMR(90 MHz, CDCl₃) δ: 1.64–2.25(m,2H), 2.50–5.74(m,6H), 2.71(s,3H), 2.90(t,J=7Hz,2H), 3.91(t,J=7Hz, 2H), 6.86–7.80(m,7H), 8.36–8.76(m,1H)
MS m/z: 518

EXAMPLE 70

6-(2-Chlorophenyl)-11-methyl-3-(tetrahydropyran-2-yl)-methoxycarbonyl)-2,3,4,5-tetrahydro-8H-pyrido[4′,3′:4,5]thieno[3,2-f][1,2,4]triazolo[4,3-a][1,4]diazepine

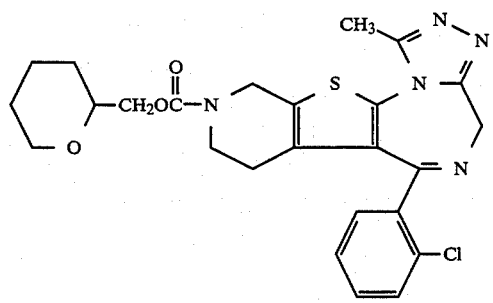

¹H-NMR(90 MHz, CDCl₃) δ: 1.12–2.32(m8H), 2.66(s,3H), 2.92–5.72(m,11H), 7.30(m,4H)
MS m/z: 499

EXAMPLE 71

6-(2-Chlorophenyl)-11-methyl-3-[2-(morpholin-2-yl)ethoxycarbonyl]-2,3,4,5-tetrahydro-8H-pyrido[4′,3′:4,5]-thieno[3,2-f][1,2,4]triazolo[4,3-a][1,4]diazepine

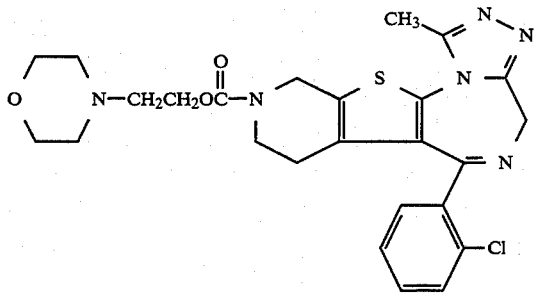

¹H-NMR(90 MHz, CDCl₃) δ: 1.54–2.24(m,2H), 2.36–2.64(m,6H), 2.68(s,3H), 3.04–5.84(m,6H), 3.52–3.80(m,4H), 4.24(t,J=7Hz,2H), 7.39(m,4H)
MS m/z: 526

PREPARATORY EXAMPLE 1

6-Acetyl-2-(2-bromopropionylamino)-3-(2chlorobenzoyl)-4,5,6,7-tetrahydro-thieno[2,3-C]pyridine

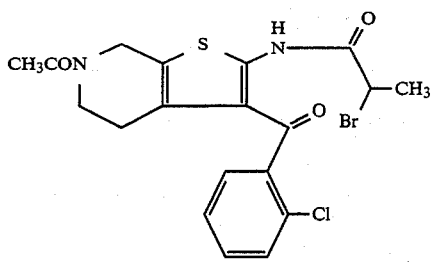

13.2 g of toluene and 3.66 liters of water were added to 600 g of 2-amino-3-(2-chlorobenzoyl)-6-acetyl-4,5,6,7-tetrahydro-thieno[2,3-C]pyridine, to which 301 g of sodium hydrogencarbonate was further added. While heating to 60° C., 301 ml of 2-bromopropionyl bromide was dropped into the solution. Further, 170 g of sodium hydrogencarbonate and 170 ml of 2-bromopropionyl bromide were added in order to complete the reaction. After cooling down to room temperature, 500 g of sodium hydrogencarbonate was added, after which the organic phase was separated. The aqueous phase was extracted twice with ethyl acetate, followed by combination with the organic phase, washing with water and drying with anhydrous magnesium sulfate. The solvent was distilled off under reduced pressure and the resultant solid matter was washed with ether to obtain 800 g of the intended product.

¹H-NMR(90 MHz, CDCl₃) δ: 1.7–2.4(m,2H), 1.99(d, J=7.2Hz, 3H), 2.06 and 2.14(each S, total 3H), 3.25–3.7(m,2H), 4.41(q, J=7.2Hz, 1H), 4.4–4.8(m,2H), 7.0–7.5(m,4H)

PREPARATORY EXAMPLE 2

6-Acetyl-2-(2-aminopropionylamino)-3-(2-chlorobenzoyl)-4,5,6,7-tetrahydro-thieno[2,3-C]pyridine

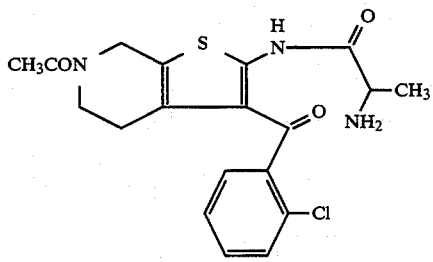

Process A 841 g of 6-acetyl-2-(2-bromopropionylamino)-3-(2-chlorobenzoyl)-4,5,6,7-tetrahydro-thieno[2,3-C]pyridine was dissolved in 0.72 liters of dichloroethane and 1.08 liters of ethyl acetate, into which ammonia gas was introduce at −10° C. The mixture was subjected to reaction in an autoclave at 100° C. for 1 hour. After completion of the reaction, excess ammonia gas was removed and the reaction solution was poured into 3N HCl under ice-cooling conditions. After extraction with a saturated sodium carbonate aqueous solution, followed by repeating extraction with chloroform. The resulting organic phase was washed with a saturated saline solution, followed by drying with anhydrous magnesium sulfate and removal of the solvent by distillation under reduced pressure to obtain 638.8 g of the intended compound.

1H-NMR(90 MHz, CDCl3) δ: 1.48(d, J=6.8Hz, 3H), 1.6–2.3(m,4H), 2.07 and 2.12(each S, total 3H), 3.25–4.0(m,3H), 4.35–4.75 (m,2H), 7.0–7.6(m,4H)

Process B

Ten grams of 2-amino-3-(2-chlorobenzoyl)-6-acetyl-4,5,6,7-tetrahydro-thieno(2,3-C)pyridine was dissolved in 150 ml of chloroform at the room temperature, 17 g of alanyl chloride hydrochloride was added little by little to the solution over a period of 1 hour at the room temperature, while agitated. After the reaction finished, 150 ml of water was added to the mixture. Agitation was conducted for 30 minutes. The aqueous phase was taken out. The phase in chloroform was treated with 150 ml of water for extraction. The two aqueous phases were collected into one. It was washed with chloroform. The aqueous phase was neutralized with sodium bicarbonate and extacted with chloroform. The resultant was treated with a reduced pressure distillation to remove out the solvent and obtain 10.1 grams of the intended compound in the form of yellow powder.

PREPARATORY EXAMPLE 3

8-Acetyl-5-[2-chlorophenyl)-3methyl-6.7,8,9-tetrahydro-1H,3H-pyrido[4',3',4,5]thieno[3,2-f][1,4-diazepin-2-one

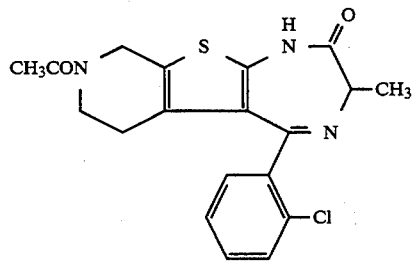

636.8 g of 6-acetyl-2-(2-aminopropionylamino)-3-(2-chlorobenzoyl)-4,5,6,7-tetrahydro-thieno[3,2-f][1,4]diazepin-2-one

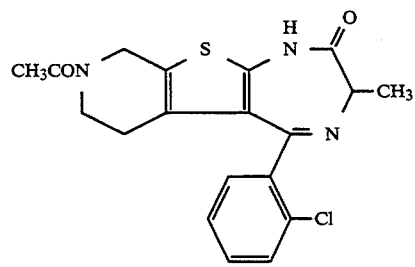

crystals to obtain 300 g of the intended product.

1H-NMR(90 MHz, CDCl3) δ: 1.3–2.6(m,2H), 1.76(d,J=6.8Hz,3H), 2.06 and 2.12(each S, total 3H), 2.8–4.1(m,2H), 3.87(q,J=6.8Hz,1H), 4.1–5.1)m,2H), 7.1–7.5(m,4H), 9.0–9.5(bs,1H)

PREPARATION EXAMPLE 4

3-Methyl-5-(2-chlorophenyl)-8-thioacetyl-6,7,8,9-tetrahydro-1H,3H-pyrido[4',3':4,5]thieno[3,2-f][1,4]diazepin-2-thione

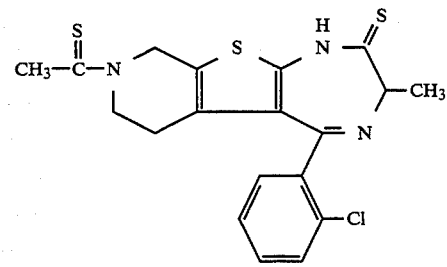

288 g of 3-methyl-5-(2-chlorophenyl)-8-acetyl-6,7,8,9-tetrahydro-1H,3H-pyrido[4',3':4,5]thieno[3,2-f][1,4]azepin-2-one was dissolved in 3 liters of dimethoxyethane, to which 186 g of sodium hydrogencarbonate and 364 g of phosphorus pentasulfide were added, followed by heating under reflux for 3 hours. The reaction solution was filtered through Celite, after which the solvent was once distilled off under reduced pressure. Methanol and dichloromethane were added to the resultant residue in small amounts for adsorption on silica gel, followed by drying and purification with dry column chromatography (elution solvent: dichloromethane:methanol=98:2), thereby obtaining 300 g of the intended compound.

PREPARATORY EXAMPLE 5

6-(2-Chlorophenyl)-3-thioacetyl-8,11-dimethyl-2,3,4-tetrahydro-8H-pyrido[4',3':4,5]thieno[3,2-f][1,2,4[triazolo[4,3-][1,4]diazepine

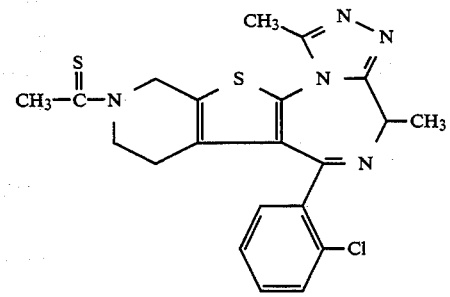

4.81 g of 3-methyl-5-(2-chlorophenyl-8-thioacetyl-6,7,8,9-tetrahydro-1H,3H-pyrido[4',3':4,5]thieno[3,2-f][1.4]diazepin-2-thione was dissolved in 70 ml of dioxane, to which 660 mg of acetohydrazide was added, followed by heating at 100° C. After cooling, the mixture was concentrated under reduced pressure and the resultant reside was purified by column chromatography (elution solvent: dichloromethane:methanol=98:2), thereby obtaining 750 g of the intended compound.

PREPARATION EXAMPLE 8

6-(2-Chlorophenyl)-8,11-dimethyl-2,3,4,5-tetrahydro-8H-pyrido[4',3':4,5]thieno[3,2-f][1,2,4]triazolo[4,3-a][1,4]diazepine

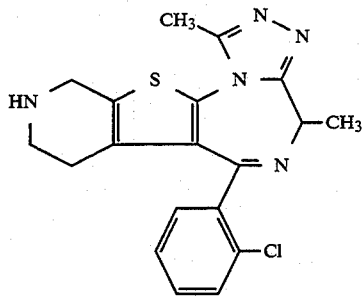

281 g of 6-(2-chlorophenyl)-8,11-dimethyl-3-thioacetyl-2,3,4,5-tetrahydro-8H-pyrido[4',3':4,5]thieno[3,2-f][1,2,4]triazolo[4,3-a][1,4]diazepine was dissolved in 1 liter of methanol, to which 0.81 liters of 4N sodium hydroxide, followed by heating under reflux. After cooling, the reaction solution was salted out and extracted with chloroform, followed by removal of the solvent by distillation under reduced pressure. The resultant residue was purified by silica gel column chromatography (elution solvent: dichloromethane:methanol=95:5), thereby obtaining 142 g of the intended compound.

$^1$H-NMR(90 MHz, CDCl$_3$) δ: 1.1-2.3(m,3H), 2.10(d,J=6.8Hz,3H), 2.45-3.3(m,2H), 2.66(s,3H), 3.85-4.1(m,2H), 4.26(q,J=6.8Hz,1H), 7.1-7.6(m,4H)
MS m/z(Pos. Fab): 384(M+H)$^-$

PREPARATORY EXAMPLE 7

(−)-6-(2-Chlorophenyl)-8,11-dimethyl-2,3,4,5-tetrahydro-8H-pyrido[4',3':4,5]thieno[3,2-f][1,2,4]triazolo[4,3-a][1,4]diazepine

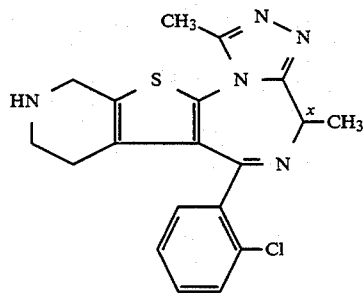

86 g of (±)-6-(2-chlorophenyl)-8,11-dimethyl-2,3,4,5-tetrahydro-8H-pyrido[4',3':4,5]thieno[3,2-f][1,2,4]triazolo [4,3-a][1,4]diazepine and 45.88 g of dibenzoyl-D-tartarate were dissolved under heating conditions in 980 ml of ethanol and 365 ml of water, and allowed to stand at room temperature. The resultant crystals were collected by filtration and washed with ether, followed by rendering free by means of a diluted sodium hydrogencarbonate aqueous solution and extraction twice with dichloromethane. The resultant organic phase was washed with a saturated saline solution and dried with anhydrous magnesium sulfate, followed by removal of the solvent by distillation under reduced pressure to obtain 11.0 g of the intended compound.

Further, the filtrate from which the tartarate had been once collected by filtration was subjected to a similar procedure set forth above, thereby obtaining 11.3 g of the intended compound.
[α]$_D^{20}$ −23.5° (C=1. EtOH)

PREPARATORY EXAMPLE 8

(+)-6-(2-Chlorophenyl)-3-(1-cyano-1-methylethoxycarbonyl)-8,11-dimethyl-2,3,4,5-tetrahydro-8H-pyrido[4',3':4,5]thieno[3,2-f][1,2,4]triazolo[4,3-a][1,4]diazepine

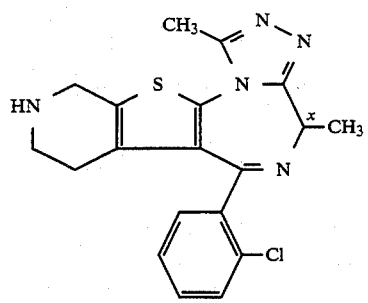

In the same manner as in Preparatory Example 7, dibenzoyl-L-tartaric acid was used to obtain the intended compound.
[α]$_D^{20}$ +17.56° (C=0.02, EtOH)

EXAMPLE 72

(+)-6-(2-Chlorophenyl)-3-(1-cyano-1-methylethoxycarbonyl)-8,11-dimethyl-2,3,4,5-tetrahydro-8H-pyrido[4',3':4,5]thieno[3,2-f][1,2,4]triazolo[4,3-a][1,4diazepine

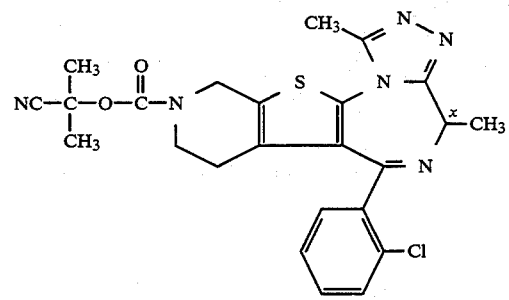

5 g of (−)-6-(2-chlorophenyl)-8,11-dimethyl-2,3,4,5-tetrahydro-8H-pyrido[4',3':4,5]thieno[3,2-f][1,2,4]triazolol-4,3-a][1,4]diazepine was dissolved in dichloromethane, to which 5 g of 1-cyano-1-methylethylphenyl carbonate was added, followed by reaction at 100° C. for 4 hours while removing the solvent by distillation. After completion of the reaction, the resultant residue was purified by column chromatography (elution solvent: chloroform:methanol=99:1), thereby obtaining 2.7 g of the intended compound.

$^1$H-NMR(90 MHz, CDCl$_3$) δ: 1.76(s,6H), 1.80-2.20(m,2H), 2.10(d,3H), 2.66(s,3H), 3.0-3.9(m,2H), 4.24(q,1H), 4.3-4.9(m,2H), 7.35(m,4H)
FABMS [M+H$^+$]481
[α]$_D^{20}$ +17.56° (C=0.02, EtOH)

EXAMPLE 73

(+)-3-(3-Butynyloxycarbonyl)-6-(2-chlorophenyl)-8,11-dimethyl-2,3,4,5-tetrahydro-8H-pyrido[4',3':4,5]-thieno]3,2-f][1,2,4]triazolo[4,3-a][1,4]diazepine

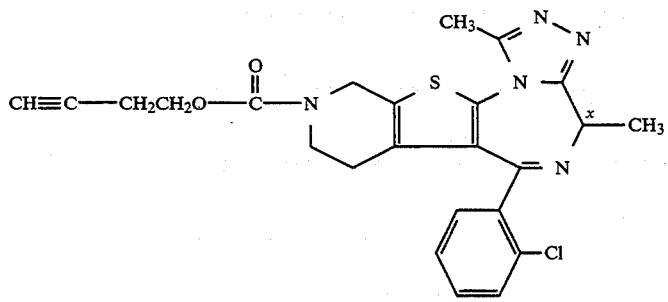

5 g of (−)-6-(2-chlorophenyl)-8,11-dimethyl-2,3,4,5-tetrahydro-8H-pyrido[4',3':4,5]thieno[3,2-f][1,2,4[trizolo[4,3-a][1,4]diazepine was dissolved in dichloromethane, to which 5g of 3-butynylphenyl carbonate, followed by reaction at 100° C. for 4 hours while distilling off the solvent. After completion of the reaction, the resultant residue was purified by column chromatography (elution solvent: dichloromethane:ethanol=99:1), thereby obtaining 1.6 g of the intended compound.

$^1$H-NMR(90 MHz, CDCl$_3$) δ: 7.4(5H,Ar), 4.9(1H,d,J=18Hz,N—CH$_{2l}$ [c-2]), 4.5(1H, d, J=18Hz, N—CH$_2$[C-2]), 4.2(1H,n,C$_8$—H), 4.1(2H,t, J=8Hz,O—CH$_3$), 2.7(3H,s), 2.5(2H,dt,J=1Hz,7Hz,≡—CH$_2$), 2.1(3H,d,J=7Hz,CHCH$_3$), 3.0–2.0 (5H,n)
[α]$_D^{24}$ +17.0° (C=1. CHCl$_3$)

EXAMPLE 74

(+)-6-(2-Chlorophenyl)-3-cyclopropanecarbonyl-8,11-dimethyl-2,3,4,5-tetrahydro-8H-pyrido[4',3':4,5]-thieno[3,2-f][1,2,4]triazolo[4,3-a][1,4]diazepine

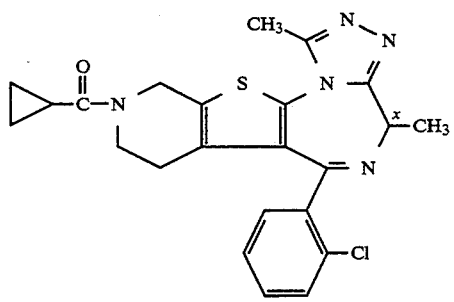

5 g of (−)-6-(2-Chlorophenyl)-3-cyclopropanecarbonyl-8,11-dimethyl-2,3,4,5-tetrahydro-8H-pyrido[4',3':4,5]thieno[3,2-f][1,2,4]triazolo[4,3-a][1,4]diazepine was dissolved in 70 ml of dichloromethane, to which 1.42 g of triethylamine was added, followed by dropping 1.44 g of cyclopropanecarbonyl chloride under ice-cooling conditions. After completion of the reaction, the reaction solution was washed with a saturated sodium hydrogen carbonate aqueous solution and then with a saturated saline solution, followed by drying with anhydrous magnesium sulfate and removal of the solvent by distillation under reduced pressure. The resultant residue was purified by silica gel column chromatography (elution solvent: dichloromethane:methanol=98:2), thereby obtaining 4.2 g of the intended compound.

$^1$H-NMR(90 MHz, CDCl$_3$) δ: 0.55–1.15(m,4H), 1.45–2.5(m,3H), 2.10(d,J=6.8Hz,3H), 2.66(s,3H), 2.8–4.8(m,3H), 4.26(q,J=6.8Hz,1H), 4.8–5.2(m,1H), 7.05–7.65(m,4H)

MS m/z(pos.Fab): 452(M+H)+
[α]$_D^{26}$ +4.97° (C=1, EtOH)
[α]$_D^{20}$ +14.91° (C=1, CHCl$_3$)

Other processes of preparing the compounds obtained in the foregoing examples are described in the following.

PREPARATORY EXAMPLE 9

1-(Cyano-1-methylethoxycarbonyl)-4-hydroxypiperidine

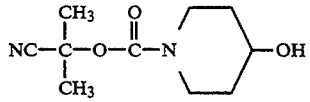

50 g of 1-cyano-1-methylethylphenyl carbonate and 25 g of 4-hydroxypiperidine were heated at 130° C. After completion of the reaction, the resulting product was purified by silica gel column chromatography (elution solvent: hexane:ethyl acetate=1:1−1:2−0:1), thereby obtaining 50.5 g of the intended compound.

$^1$H-NMR(90 MHz, CDCl$_3$) δ: 1.26–2.10(m,5H), 1.80(s,6H), 2.96–3.35(m,2H), 3.60 –4.15(m,3H)

PREPARATORY EXAMPLE 10

1-(Cyano-1-methylethoxycarbonyl)-4-piperidone

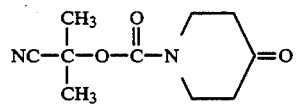

5.06 ml of dimethylsulfoxide was gradually dropped, at −78° C. into a solution of 4.15 ml of oxalyl chloride in dichloromethane (50 ml), into which a dichloromethane solution of 5.05 g of 1-(1-cyano-1-methylethoxycarbonyl)-4-hydroxypiperidine was dropped. After agitation at the temperature for 1 hour, 16.57 ml of triethylamine was added, followed by agitation at room temperature for 1 hour. The reaction solution was filtered, washed with water, and dried with anhydrous magnesium sulfate. The solvent was distilled off and the resultant residue was purified by silica gel column chromatography (elution solvent: ethyl acetate:n-hexane=1:9), thereby obtaining 3.9 g of the intended compound.

¹H-NMR(90 MHz, CDCl₃) δ: 1.80(s,6H), 2.48(t, J=7 Hz,4H), 3.74(t, J=7 Hz,4H)

PREPARATORY EXAMPLE 11

2-Amino-3-(2-chlorobenzoyl)-6-(1-cyano-1-methylethoxycarbonyl)-4,5,6,7-tetrahydro-thieno[2,3-C]pyridine

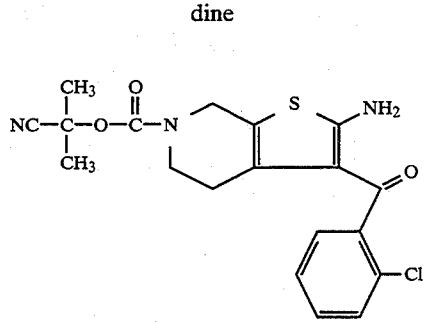

1.6 ml of triethylamine was added to a mixture of 3.9 g of the compound obtained in Preparatory Example 10, 0.6 g of sulfur, 3.3 g of 2-chlorocyanoacetophenone and 20 ml of N,N-dimethylformamide at 40° C. and agitated at 60° C. for 3 hours. After completion of the reaction, the solvent was evaporated to dryness and washed with ethyl acetate to obtain 5.0 g of the intended compound.

¹H-NMR(90 MHz, CDCl₃) δ: 1.60–1.95(m,2H), 1.75(s,6H), 3.40(m,2H), 4.32(m,2H), 7.10–7.50(m,6H)

PREPARATORY EXAMPLE 12

2-(2-Bromopropionylamino)-3-(2-chlorobenzoyl)-6-(1-cyano-1-methylethoxycarbonyl)-4,5,6,7-tetrahydro-thieno[2,3-C]pyridine

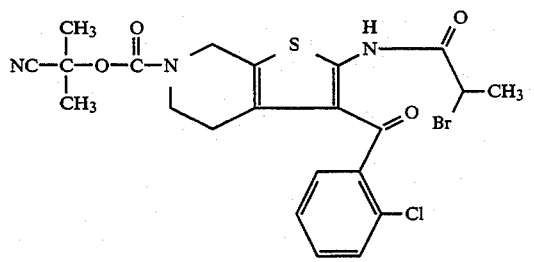

4.6 g of 2-bromopropionyl bromide was dropped into a mixture of 5.0 g of the compound obtained in Preparatory Example 11, 2.1 g of sodium hydrogencarbonate, 50 ml of water and 200 ml of toluene at 60° C. After completion of the reaction, ethyl acetate was added, fro which the aqueous phase was removed. The organic phase was washed with a saturated saline solution and dried with anhydrous magnesium sulfate. The solvent was distilled off to obtain 6.0 g of the intended compound.

¹H-NMR(90 MHz, CDCl₃) δ: 1.76(s,6H), 1.88(m,2H), 2.00(d, J=7 Hz, 3H), 3.24–3.60(m,2H), 4.20–4.68(m,2H), 4.62(q, J=7 Hz, 1H), 7.00–7.50(m,4H)

PREPARATORY EXAMPLE 13

2-(2-Aminopropionylamino)-3-(2-chlorobenzoyl)-6-(1-cyano-1-methylethoxycarbonyl)-5,6,7,8-tetrahydro-thieno[2,3-C]pyridine

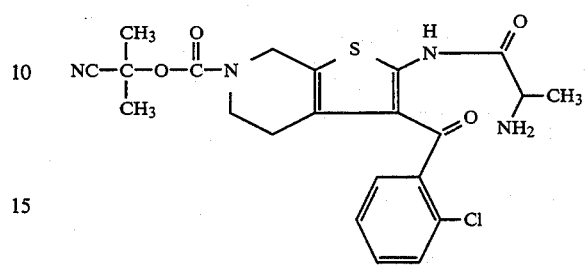

6.0 g of the compound obtained in Preparatory Example 12 was dissolved in 50 ml of ethyl acetate, into which ammonia was introduced at −20° C. for 2 hours, followed by agitation in a sealed tube at 100° C. for 5 hours. After completion of the reaction, the reaction produce was extracted with 2N hydrochloric acid and the resultant aqueous phase was neutralized with sodium hydrogencarbonate, which was subsequently saturated with sodium chloride and extracted with chloroform. After drying with anhydrous magnesium sulfate, the solvent was distilled off to obtain 0.7 g of the intended compound.

¹H-NMR(90 MHz, CDCl₃) δ: 1.51(d, J=7 Hz,3H), 1.50–2.04(m,2H), 1.78(s,6H), 3.28–3.60(m,2H), 3.62–3.96(m,1H), 4.50(m,2H), 7.20–7.54(m,4H)

PREPARATORY EXAMPLE 14

3-Methyl-5-(2-chlorophenyl)-8-(1-cyano-1-methylethoxycarbonyl)-6,7,8,9-tetrahydro-1H,3H-pyrido[4',3':4,5]thieno[2,3-e][1,4]diazepin-2-one

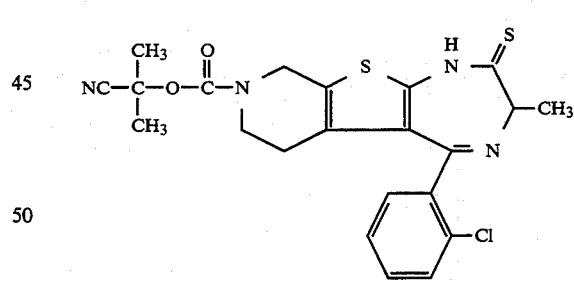

A mixture of 0.4 g of the compound obtained in Preparatory Example 13, 0.7 g of phosphorus pentasulfide. 0.4 g of sodium hydrogencarbonate and 40 ml of 1,2-dimethoxyethane was refluxed for 2 hours. After completion of the reaction, the solvent was distilled off, to which methanol was added, followed by removal of insoluble matters by filtration and concentration. The residue was purified by silica gel column chromatography (elution solvent: chloroform:methanol=99:1), thereby obtaining 0.3 g of the intended compound.

¹H-NMR(90 MHz, CDCl₃) δ: 1.50–2.0(m,2H), 1.76(s,6H), 1.92(d,J=7 Hz,3H), 3.0–4.0(m,2H), 4.0–4.3(m,1H), 4.3–5.0(m,2H), 7.1–7.6(m,4H)

EXAMPLE 75

3-(1-Cyano-1-methylethoxycarbonyl)-6-(2-chlorophenyl)-8,11-dimethyl-2,3,4,5-tetrahydro-8H-pyrido[4',3':4,5]thieno[3,2-f][1,2,4]triazolo[4,3-a][1,4]diazepine

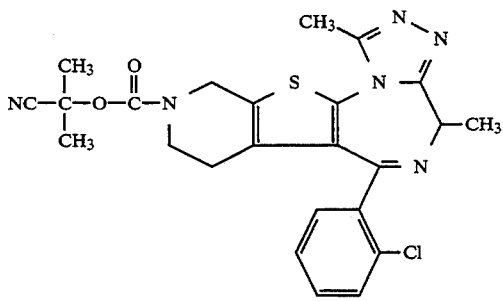

0.3 g of the compound obtained in Preparatory Example 14 and 0.3 g of acetohydrazide were dissolved in 20 ml of 1,4-dioxane and refluxed for 3 hours. After completion of the reaction, the solvent was distilled off and the residue was purified by silica gel column chromatography (elution solvent: chloroform:methanol=99:1), thereby obtaining 0.20 g of the intended compound.

¹H-NMR(90 MHz, CDCl₃) δ: 1.76(s,6H), 1.80–2.20(m,2H), 2.10(d,3H), 2.66(s,3H), 3.0–3.9(m,2H), 4.24(q,1H), 4.3–4.9(m,2H), 7.35(m,4H)

PREPARATORY EXAMPLE 15

N-(3-Butynyloxycarbonyl)-4-hydroxypiperidine

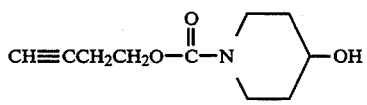

10.0 g of 3-butynylphenyl carbonate and 5.8 g of 4-hydroxypiperidine were heated in a solvent-free condition at 100° C. of 30 minutes. After completion of the reaction, silica gel column chromatography (elution solvent: hexane:ethyl acetate=1:1–1:2) was used for purification to obtain 10.6 g of the intended compound.

¹H-NMR(90 MHz, CDCl₃) δ: 1.16–2.1(m,5H), 1.98(t,J=2 Hz,1H), 1.42(dt,J=2 Hz,7 Hz,2H), 2.9–3.5(m,2H), 3.6–4.1(m,3H), 4.15(t,J=7 Hz,2H)

PREPARATORY EXAMPLE 16

N-(3-Butynyloxycarbonyl)-4-piperidone

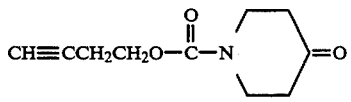

25 ml of oxalyl chloride was added to 500 ml of dichloromethane, into which 4 ml of dimethyl sulfoxide was gradually dropped in a stream of nitrogen at a temperature of from −50° C. to −70° C. Subsequently, 10.3 g of N-(3-butynyloxycarbonyl)-4-hydroxypiperidine was dissolved in 50 ml of dichloromethane, followed by gradually dropping into the reaction mixture. Finally, 120 ml of triethylamine was dropped, followed by gradually increasing the temperature up to room temperature. The reaction solution was charged into a saturated saline solution, extracted three times with dichloromethane and dried with anhydrous magnesium sulfate, after which the solvent was distilled off under reduced pressure. The resultant residue was purified by the use of silica gel column chromatography (elution solvent: hexane:ethyl acetate=3:1), thereby obtaining 8.9 g of the intended compound.

¹H-NMR(90 MHz, CDCl₃) δ: 2.0(t,J=2 Hz,1H), 2.3–2.8(m,6H), 3.76(t,J=7 Hz,4H), 4.21(t,J=7 Hz,2H)

PREPARATORY EXAMPLE 17

2-Amino-3-(2-chlorobenzoyl)-6-(3-butynyloxycarbonyl)-4,5,6,7-tetrahydro-thieno[2,3-C]pyridine

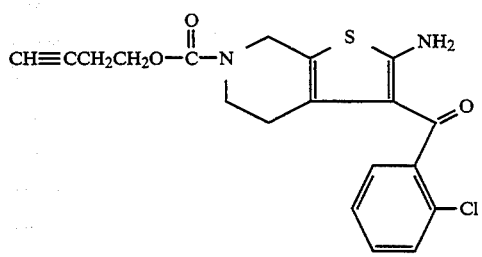

7.4 g of N-(3-butynyloxycarbonyl)-4-piperidone, 1.21 g of sulfur and 61.5 g of 2-chlorocyanoacetophenone were dissolved in 25 ml of dimethylformamide, to which 3.5 ml of triethylamine was further added, followed by agitation at 60° C. for 1 hour. After completion of the reaction, silica gel column chromatography (elution solvent: dichloromethane:methanol=99:1) was used for purification, thereby obtaining 11.2 g of the intended compound.

¹H-NMR(90 MHz, CDCl₃) δ: 1.64–1.90(m,2H), 1.96(t,J=2 Hz,1H), 2.3–2.7(t,J=2 Hz,7 Hz,2H), 3.4(t,J=7 Hz,2H), 4.14(t,J=7 Hz,2H), 4.3–4.5(m,2H), 7.0–7.5(m,6H)

PREPARATORY EXAMPLE 18

2-(2-Bromopropionylamino)-3-(2-chlorobenzoyl)-6-(3-butynyloxycarbonyl)-4,5,6,7-tetrahydro-thieno[2,3-C]pyridine

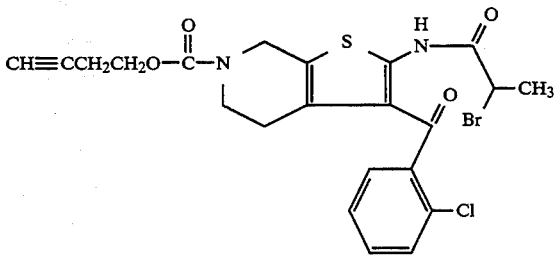

1.35 g of 2-amino-3-(2-chlorobenzoyl)-6-(3-butynyloxycarbonyl)-4,5,6,7-tetrahydro-thieno[2,3-C]pyridine was dissolved in 20 ml of dioxane, to which 0.33 g of pyridine was added, followed by dropping at 0° C. 0.90 g of 2-bromopropionyl bromide. After completion of the reaction, the reaction mixture was charged into water, extracted with dichloromethane and dried with anhydrous magnesium sulfate, after which the solvent was distilled off under reduced pressure. The resultant residue was purified by silica gel column chromatography (elution solvent: dichloromethane:hexane=1:1–1:0), thereby obtaining 1.19 g of the intended compound.

¹H-NMR(90 MHz, CDCl₃) δ: 2.02(t,J=7 Hz,3H), 1.7–2.2(m,3H), 3.5(dt,J=2 Hz,7 Hz,2H), 3.44(t,J=7 Hz,2H), 4.16(t,J=7 Hz,2H), 4.4–4.8(m,3H), 7.0–7.5(m,5H)

PREPARATORY EXAMPLE 19

2-(2-Aminopropionylamino)-3-(2-chlorobenzoyl)-6-(3-butynyloxycarbonyl)-4,5,6,7-tetrahydro-thieno[2,3-C]pyridine

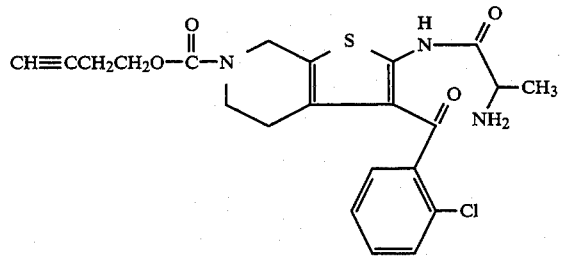

1.16 g of 2-(2-bromopropionylamino)-3-(2-chlorobenzoyl)-6-(3-butynyloxycarbonyl)-4,5,6,7-tetrahydro-thieno[2,3-C]pyridine was dissolved in 36 ml of ethyl acetate, into which ammonia gas was introduced under cooling conditions, followed by heating in a sealed tube at 100° C. After completion of the reaction, the mixture was cooled, to which 50 ml of ethyl acetate was added. The mixture was washed with 1N hydrochloric acid, after which the aqueous phase was neutralized with a sodium carbonate aqueous solution and extracted with chloroform. The resultant organic phase was dried with anhydrous magnesium sulfate. The solvent was distilled off under reduced conditions and the resultant residue was purified by the use of silica gel column chromatography (elution solvent: dichloromethane), thereby obtaining 0.36 g of the intended compound.

¹H-NMR(90 MHz, CDCl₃) δ: 1.5(t,J=7 Hz,3H), 1.6–1.8(brs,2H), 1.8–2.1(m,3H), 2.52(dt,J=2 Hz,2H), 3.44(t,J=7 Hz,2H), 3.76(q,J=7 Hz,1H), 4.16(t,J=7 Hz,2H), 4.5–4.64(m,2H), 7.1–7.7(m,5H)

PREPARATORY EXAMPLE 20

3-Methyl-5-(2-chlorophenyl)-8-(3-butynyloxycarbonyl)-6,7,8,9-tetrahydro-1H,3H-pyrido[4',3':4,5]-thieno[3,2-f][1,4]diazepin-2-one

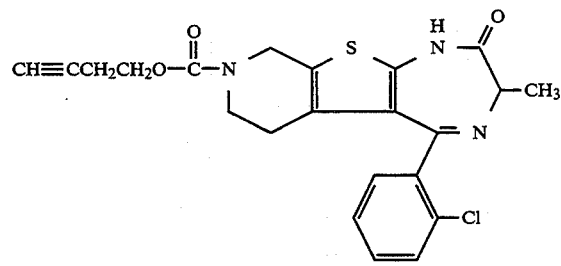

0.36 g of 2-(2-aminopropionylamino)-3-(2-chlorobenzoyl)-6-(3-butynyloxycarbonyl)-4,5,6,7-tetrahydro[2,3-C]pyridine was dissolved in 10 ml of toluene and 0.8 ml of pyridine, to which 0.18 ml of acetic acid, followed by refluxing while removing the resultant water. After completion of the reaction, the toluene was distilled off under reduced pressure and dichloromethane was added to the distilled reaction solution, followed by washing with water and drying with anhydrous magnesium sulfate. The solvent was distilled off under reduced pressure and the resultant residue was purified by the use of silica gel column chromatography (elution solvent)dichloromethane:methanol=100:0–97:3), thereby obtaining 0.22 g of the intended compound.

¹H-NMR(90 MHz, CDCl₃) δ: 1.76(d,J=7 Hz,3H), 1.6–2.2(m,3H), 2.5(dt,J=2 Hz,7 Hz,2H), 2.9–4.0(m,2H), 3.86 (q,J=7 Hz,1H), 4.17(t,J=7 Hz,2H), 4.3–4.9(m,2H), 7.0–7.6(m,5H)

PREPARATORY EXAMPLE 21

3-Methyl-5-(2-chlorophenyl)-8-(3-butynyloxycarbonyl)-6,7,8,9-tetrahydro-1H,3H-pyrido[4',3':4,5]-thieno[3,2-f][1,4]diazepin-2-thione

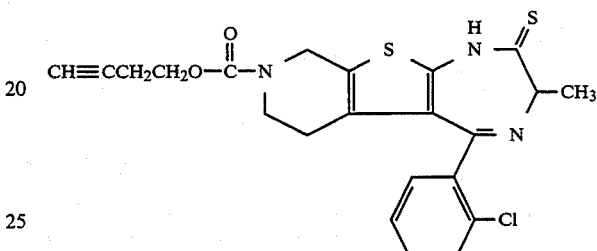

0.21 g of 3-methyl-5-(2-chlorophenyl)-8-(3-butynyloxycarbonyl)-6,7,8,9-tetrahydro-1H,3H-pyrido[4',3':4,5]thieno[3,2-f][1,4]diazepin-2-one was dissolved in 10 ml of dimethoxyethane, to which 0.11 g of sodium hydrogencarbonate and 0.22 g of phosphorus pentasulfide were added, followed by heating at 80° C. for 3 hours. After completion of the reaction, dichloromethane and methanol were added, and the mixture was filtered, followed by addition of silica gel to the resultant filtrate and evaporating the solvent to dryness. Silica gel column chromatography (elution solvent: dichloromethane:methanol=99:1) was used for purification, thereby obtaining 0.15 g of the intended compound.

¹H-NMR(90 MHz, CDCl₃) δ: 1.12–2.00(m,2H), 1.73(d,J=7 Hz,3H), 2.12(t,J=2 Hz,1H), 2.40(dt,J=2 Hz,7 Hz,2H), 2.64–3.80(m,2H), 4.01(q,J=7 Hz,1H), 4.02(t,J=7 Hz,2H), 4.10–4.76(m,2H), 7.28(m,2H)

EXAMPLE 76

3-(3-Butynyloxycarbonyl)-6-(2-chlorophenyl)-8,11-dimethyl-2,3,4,5-tetrahydro-8H-pyrido[4',3':4,5]-thieno[3,2-f][1,2,4]triazolo[4,3-a][1,4]diazepine

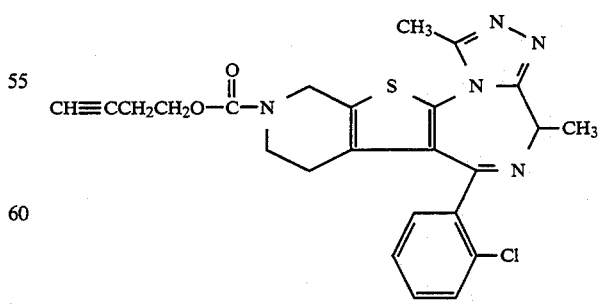

100 mg of acetohydrazide was added to 150 mg of 3-methyl-5-(2-chlorophenyl)-8-(3-butynyloxycarbonyl)-6,7,8,9-tetrahydro-1H,3H-pyrido[4',3':4,5]-thieno[3,2-f][1,4]diazepin-2-thione, to which 2 ml of dioxane was further added, followed by heating at 130° C. for 3 hours while distilling off the solvent. After completion of the reaction, the resultant residue was purified by the use of silica gel column chromatography (elution solvent: dichloromethane:methanol=98:2), thereby obtaining 80 mg of the intended compound.

$^1$H-NMR(90 MHz, CDCl$_3$) δ: 7.5(4H,Ar), 4.9(1H,d,J=18 Hz,N—CH$_2$[C-2:]), 4.5(1H,d,J=18 Hz,N—CH$_2$[C-2:]), 4.2(1H,m,C$_6$—H), 4.1(2H,t,J=8 Hz,O—CH$_2$), 2.7(3H,s), 2.5(2H,dt,J=1 Hz,7 Hz,=—CH$_2$), 2.1(3H,d,J=7 Hz,CH<u>CH</u>), 3.0–2.0(5H,m)

PREPARATORY EXAMPLE 22

1-Cyclopropanecarbonyl-4-hydroxypiperidine

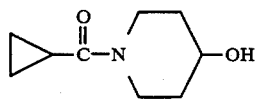

20 g of 4-hydroxypiperidine was dissolved in 400 ml of dichloromethane, to which 24 g of triethylamine was added. At −60° C., 100 ml of a dichloromethane solution containing 20.7 g of cyclopropanecarbonyl chloride was further added. After completion of the reaction, the reaction solution was extracted with chloroform under salting-out conditions and dried with anhydrous magnesium sulfate, and the solvent was distilled off under reduced pressure. The resultant residue was purified by the use of silica gel column chromatography (elution solvent: dichloroethane), thereby obtaining 32 g of the intended compound (yield 96%).

$^1$H-NMR(90 MHz, CDCl$_3$) δ: 0.55–1.55(m,4H), 1.15–2.15(m,5H), 2.4(bs,1H), 2.8–3.55(m,2H), 3.65–4.3(m,3H)

PREPARATORY EXAMPLE 23

1-Cyclopropanecarbonyl-4-piperidone

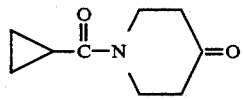

66 g of oxalic chloride was dissolved in 500 ml of dichloroethane, into which 61 g of dimethyl sulfoxide was gradually dropped at −67° C. 44 g of 1-cyclopropanecarbonyl-4-hydroxypiperidine dissolved in 200 ml of dichloromethane was dropped into the above solution at −67° C. At −67° C., 131 g of triethylamine was further added, followed by returning to room temperature. The resultant salt was removed by filtration and the filtrate was once concentrated, after which water was added to the concentrate, followed by extraction with ethyl acetate and drying with anhydrous magnesium sulfate. Moreover, the aqueous phase was extracted with chloroform and dried similarly. The solvent was distilled off under reduced pressure and the resultant reside was purified by the use of silica gel column chromatography (elution solvent: ethyl acetate:hexane=3:7), thereby obtaining 33 g of the intended compound (yield 76%).

$^1$H-NMR(90 MHz, CDCl$_3$) δ: 0.65–1.2(m,4H), 1.6–2.0(m,1H), 2.49(t,J=6.1 Hz,4H), 3.91(t,J=6 Hz,4H)

PREPARATORY EXAMPLE 24

2-Amino-3-(2-chlorobenzoyl)-6-cyclopropanecarbonyl-4,5,6,7-tetrahydro-thieno[2,3-C]pyridine

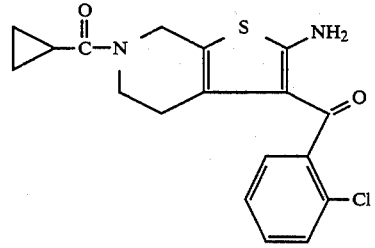

33 g of 1-cyclopropanecarbonyl-4-piperidone, 6.3 g of sulfur and 25.5 g of 2-chloro-cyanoacetophenone were dissolved in 330 ml of N,N-dimethylformamide, to which 20 g of triethylamine was added at 60° C. After completion of the reaction, the solvent was distilled off under reduced pressure and methanol was added to the resultant residue for crystallization. The crystals were filtered and washed with methanol to obtain 49.4 g of the intended compound (yield 69%).

$^1$H-NMR(90 MHz, CDCl$_3$) δ: 0.55–1.15(m,4H), 1.4–2.0(m,3H), 3.35–3.75(m,2H), 4.3–4.7(m,2H), 7.0–7.7(m,4H)

PREPARATORY EXAMPLE 25

2-(2-Bromopropionylamino)-3-(2-chlorobenzoyl)-6-cyclopropanecarbonyl-4,5,6,7-tetrahydro-thieno[2,3-C]pyridine

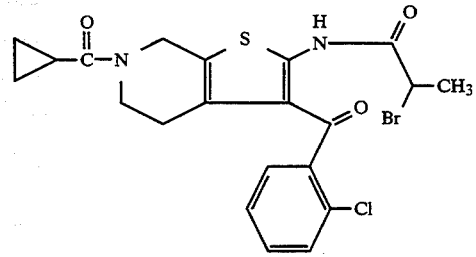

450 ml of toluene and 150 ml of water were added to 21.83 g of 2-amino-3-(2-chlorobenzoyl)-6-cyclopropanecarbonyl-4,5,6,7-tetrahydro-thieno[2,3-C]pyridine. 10.16 g of sodium hydrogencarbonate was further added, to which 9.5 ml of 2-bromopropionyl bromide was added while heating to 50° to 60° C. Moreover, a sodium hydrogencarbonate aqueous solution (10.6 g of sodium hydrogencarbonate and 150 ml of water1) and 5 ml of 2-bromopropionyl bromide were added to complete the reaction. After the completion of the reaction, ethyl acetate was added and the reaction solution was washed once with a saturated saline solution and dried with anhydrous magnesium sulfate, and the solvent was distilled off under reduced pressure to obtain 29.9 g of the intended compound (at a quantitative yield).

$^1$H-NMR(90 MHz, CDCl$_3$) δ: 0.55–1.2(m,4H), 1.6–2.2(m,3H), 1.99(d,J=7.2 Hz,3H), 3.35–3.8(m,2H), 4.45–4.85(m,2H), 4.61(q,J=7.2 Hz,1H), 7.0–7.6(m,4H)

PREPARATORY EXAMPLE 26

2-(2-Aminopropionylamino)-3-(2-chlorobenzoyl)-6-cyclopropanecarbonyl-4,5,6,7-tetrahydro-thieno-[2,3-C]pyridine

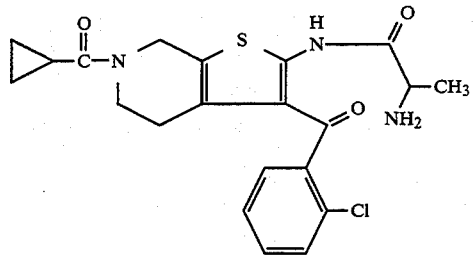

23.04 g of 2-(2-bromopropionylamino)-3-(2-chlorobenzoyl)-6-cyclopropanecarbonyl-4,5,6,7-tetrahydro-thieno[2,3-C]pyridine was dissolved in 65 ml of 1,2dichloroethane and 65 ml of ethyl acetate, into which ammonia gas was passed at −15° C. for 1 hour. This solution was placed in a sealed tube and reacted at 110° C. for 2 hours. In order to complete the reaction, ammonia was again passed into the solution at −15° C. for 30 minutes in the sealed tube where the reaction was continued at 110° C. for 1.5 hours. After ice-cooling, the reaction solution was charged into ice-cooled 2N hydrochloric acid, to which ethyl acetate was added, from which the resultant aqueous phase was collected. Sodium carbonate was added to the aqueous phase under ice-cooling conditions so that the pH was adjusted to 8, followed by extraction with chloroform under salting-out conditions. The extract was washed with a saturated saline solution and dried with anhydrous magnesium sulfate, followed by filtration and concentration to obtain 12.97 g (yield 64%) of the intended compound.

$^1$H-NMR(90 MHz, CDCl$_3$) δ: 0.45–1.2(m,4H), 1.48(d,J=7.2 Hz,3H), 1.4–2.4(m,3H), 3.35–3.85(m,2H), 3.74(q,J=7.2 Hz,1H), 4.45–4.85(m,2H), 7.0–7.7(m,4H)

PREPARATORY EXAMPLE 27

5-(2-Chlorophenyl)-8-cyclopropanecarbonyl-3-methyl-6,7,8,9-tetrahydro-1H,3H-pyrido[4',3':4,5]thieno[3,2-f][1,4]diazepin-2-one

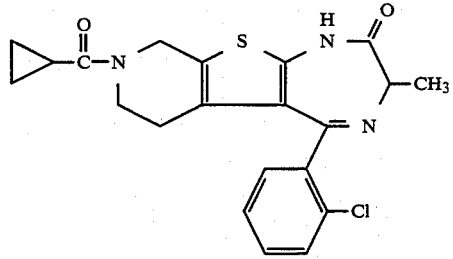

12.95 g of 2-(2-aminopropionylamino)-3-(2-chlorobenzoyl)-6-cyclopropanecarbonyl-4,5,6,7-tetrahydro-thieno[2,3-C]pyridine was dissolved in 260 ml of toluene and 90 ml of pyridine, to which 5.4 g of acetic acid was added, followed by heating under reflux for 5 hours. After removal of the solvent by distillation, benzene was added and the resultant crystals were collected by filtration to obtain 2.96 g of the intended compound. The mother liquor was subjected to silica gel column chromatography (elution solvent: ethyl acetate:hexane=4:6) to obtain 3.84 g of the intended compound.

$^1$H-NMR(90 MHz, CDCl$_3$) δ: 0.5–1.25(m,4H), 1.3–2.3(m,3H), 1.75(d,J=6.5 Hz,3H), 2.8–5.25(m,5H), 7.0–7.65(m,4H)

PREPARATORY EXAMPLE 28

5-(2-Chlorophenyl)-8-cyclopropanethiocarbonyl-3-methyl-6,7,8,9-tetrahydro-1H,3H-pyrido[4',3':4,5]-thieno[3,2-f][1,4]diazepin-2-thione

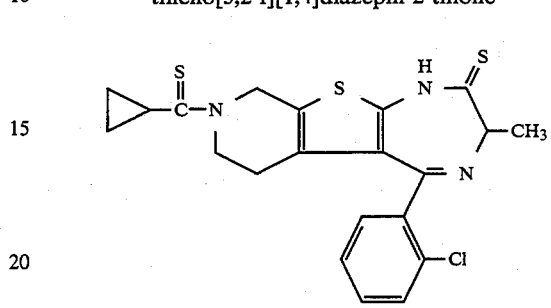

2.92 g of 5-(2-chlorophenyl)-8-cyclopropanecarbonyl-3-methyl-6,7,8,9-tetrahydro-1H,3H-pyrido[4',3':4,5]thieno[3,2-f][1,4]diazepin-2-one was suspended in 60 ml of 1,2-dimethoxyethane, to which 1.78 g of sodium hydrogencarbonate and 3.94 g of phosphorus pentasulfide were added, followed by heating under reflux for 4 hours. The reaction solution was filtered through Celite and and filter cake was washed sufficiently with 30% methanol-dichloromethane and combined with the filtrate. The methanol filtrate was concentrated and subjected to silica gel column chromatography (elution solvent: dichloromethane) to obtain 1.03 g of the intended compound (yield 33%).

$^1$H-NMR(90 MHz, 10%CD$_3$OD-CDCl$_3$) δ: 0.8–1.55(m,4H), 1.6 2.75 (m,3H), 2.00(d,J=6.1 Hz,3H), 3.2–5.2 and 5.6–6.2(each m, total 5H), 7.2–7.8(m,4H)

MS m/z(Pos. FAB): 446(M+H)$^-$

PREPARATORY EXAMPLE 29

6-(2-Chlorophenyl)-3-cyclopropanethiocarbonyl-8,11-dimethyl-2,3,4,5-tetrahydro-8H-pyrido[4',3':4,5]-thieno[3,2-f][1,2,4]triazolo[4,3-a][1,4]diazepine

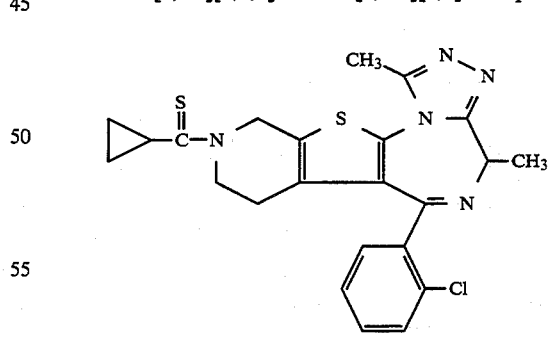

1.00 g of 5-(2-Chlorophenyl)-8-cyclopropanecarbonyl-3-methyl-6,7,8,9-tetrahydro-1H,3H-pyrido[4',3':4,5]thieno[3,2-f][1,4]diazepin-2-thione was dissolved in 40 ml of dioxane, to which 0.17 g of acetohydrazide was added, followed by agitation at an ambient temperature for 90° C. for 10 hours and then at 120° C. for 1 hour. 0.17 g of acetohydrazide was further added, followed by further agitation at 120° C. for 1 hour to complete the reaction. After removal of the solvent by distillation, the residue was subjected to silica gel column chromatography (elution solvent:dichloromethane:methanol=99:1) to obtain 280 mg of the intended compound (yield 27%).

¹H-NMR(90 MHz, CDCl₃) δ: 0.75–1.75(m,4H), 1.75–2.6(m,3H), 2.10(d,J=6.8 Hz,3H), 2.67(s,3H), 3.2–4.6(m,2H), 4.26(q,J=6.8 Hz,1H), 4.65–5.4 and 5.55–6.0(each m, total 2H), 7.0–7.65(m,4H)

EXAMPLE 77

6-(2-Chlorophenyl)-3-cyclopropanecarbonyl-8,11-dimethyl-2,3,4,5-tetrahydro-8H-pyrido[4',3':4,5]-thieno[3,2-f][1,2,4]triazolo[4,3-a][1,4]diazepine

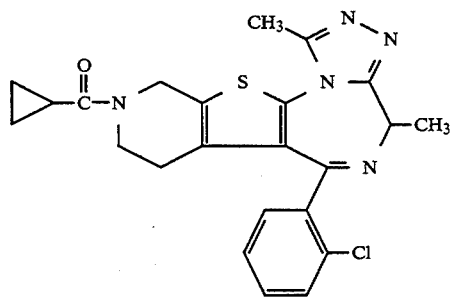

100 mg of 6-(2-chlorophenyl)-3-cyclopropanethiocarbonyl-8,11-dimethyl-2,3,4,5-tetrahydro-8H-pyrido[4',3':4,5]thieno[3,2-f][1,2,4-triazolo[4,3-a][1,4]diazepine was dissolved in 10 ml of dichloromethane, to which 10 ml of 4N hydrochloric acid was added, followed by further addition of 1 ml of an aqueous solution containing 30 mg of sodium nitrite under agitation. The solution was ice-cooled, to which sodium carbonate was added for adjustment of the pH to 8, followed by extraction with dichloromethane, washing with a saturated saline solution and drying with anhydrous magnesium sulfate. The solution was filtered and a concentrated residue was subjected to silica gel column chromatography (elution solvent: dichloromethane:methanol=99:1), thereby obtaining 69.9 mg of the intended compound (yield 72%).

¹H-NMR(90 MHz, CDCl₃) δ: 0.55–1.15(m,4H), 1.45–2.5(m,3H), 2.10(d,J=6.8 Hz,3H), 2.66(s,3H), 2.8–4.8(m,3H), 4.26(q,J=8 Hz,1H), 4.8–5.2(m,1H), 7.05–7.65(m,4H)

MS m/z(Pos. FAB): 452(M+H)⁻

EXAMPLE 78

3-[3-(Tetrahydropyran-4-yl)oxyethyl]oxycarbonyl-6-(2-chlorophenyl)-11-methyl-2,3,4,5-tetrahydro-8H-pyrido[4',3':4,5]thieno[3,2-f][1,2,4]triazolo[4,3-a][1,4]diazepine

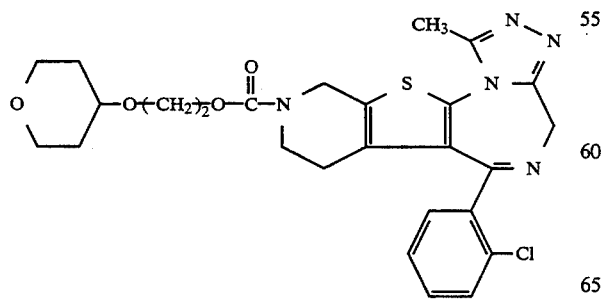

¹H-NMR(90 MHz, CDCl₃) δ: 1.30–2.40(m,6H), 2.68(s,3H), 2.80–5.70(m,15H), 7.20–7.54(m,4H)

EXAMPLE 79

6-(2-Chlorophenyl)-3-cyclohexylethoxycarbonyl-11-methyl-2,3,4,5-tetrahydro-8H-pyrido[4',3':4,5]-thieno[3,2-f][1,2,4]triazolo[4,3-a][1,4]diazepine

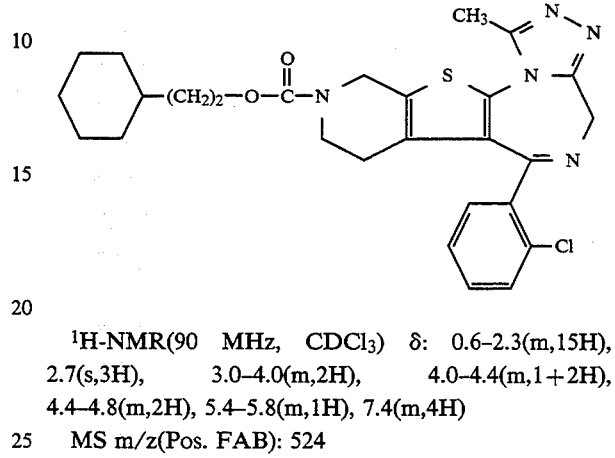

¹H-NMR(90 MHz, CDCl₃) δ: 0.6–2.3(m,15H), 2.7(s,3H), 3.0–4.0(m,2H), 4.0–4.4(m,1+2H), 4.4–4.8(m,2H), 5.4–5.8(m,1H), 7.4(m,4H)

MS m/z(Pos. FAB): 524

EXAMPLE 80

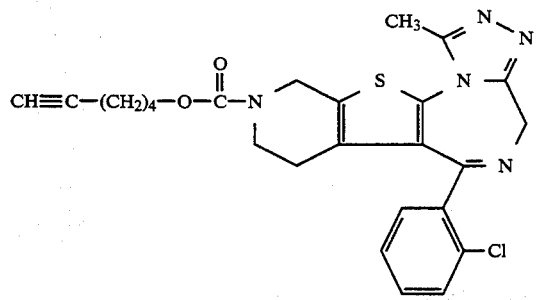

¹H-NMR(90 MHz, CDCl₃) δ: 1.20–2.32(m,6H), 1.94(t,J=2 Hz,1H), 2.21(dt,J=2 Hz,7 Hz,2H), 2.66(s,3H), 2.84–5.76(m,6H), 4.08(t,J=7 Hz,2H), 7.28(m,4H)

MS m/z(Pos. FAB): 495(M+H⁺)

EXAMPLE 81

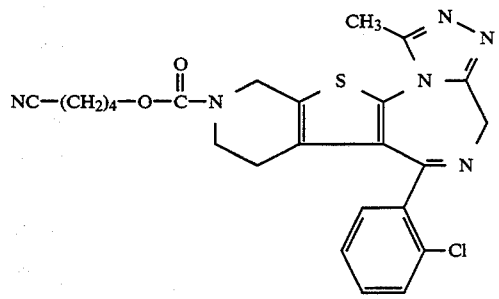

¹H-NMR(90 MHz, CDCl₃) δ: 1.40–2.21(m,6H), 2.37(t,J=7 Hz,2H), 2.67(s,3H), 2.92–5.80(m,6H), 4.11(t,J=7 Hz,2H), 7.31(m,4H)

MS m/z(Pos. FAB): 494(M+H⁺)

EXAMPLE 82

6-(2-Chlorophenyl)-3-(1-cyanoethoxy)carbonyl-11-methyl-2,3,4,5-tetrahydro-8H-pyrido[4',3':4,5]-thieno[3,2-f][1,2,4]triazolo[4,3-a][1,4]diazepine

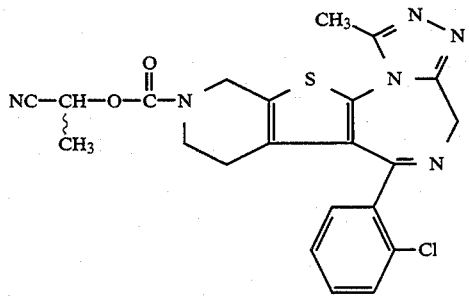

$^1$H-NMR(90 MHz, CDCl$_3$) δ: 1.70(t,J=7.0 Hz,3H), 1.75(m,1H), 2.15(m,1H), 2.69(s,3H), 3.25(m,1H), 3.85(m,1H), 4.20(m,1H), 4.53(m,1H), 4.85(m,1H), 5.43(m,1H), 5.65(m,1H), 7.23–7.65(m,4H)
MS m/z(Pos. FAB): 467(M$^+$)

EXAMPLE 83

6-(2-Chlorophenyl)-3-cyclobutyloxycarbonyl-11-methyl-2,3,4,5-tetrahydro-8H-pyrido[4',3':4,5]thieno[3,2-f][1,2,4]triazolo[4,3-a][1,4]diazepine

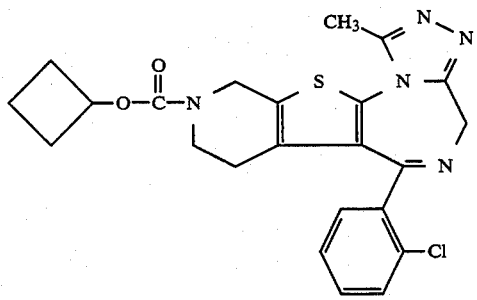

$^1$H-NMR(90 MHz, CDCl$_3$) δ: 1.5–2.5(m,8H), 2.7(s,3H), 3.0–4.0(m,2H), 4.0–4.9(m,1+1+2H), 5.4–5.8(m,1H), 7.4(m,4H)
MS m/z(Pos. FAB): 468

EXAMPLE 84

6-1(2-Chlorophenyl)-3-(2methyl-2-cyanopropyloxy)-carbonyl-11-methyl-2,3,4,5-tetrahydro-8H-pyrido[4',3':4,5]thieno[3,2-f][1,2,4]triazolo[4,3-a][1,4]diazepine

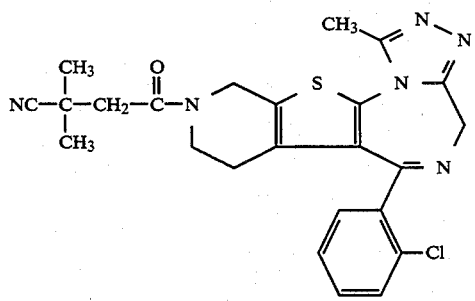

$^1$H-NMR(90 MHz, CDCl$_3$) δ: 1.35(s,3H), 1.45(s,3H), 1.75(m,1H), 2.12(m,1H), 2.70(s,3H), 3.25(m,1H), 3.90(m,1H), 4.08(s,2H), 4.22(m,1H), 4.55(m,1H), 4.56(m,1H), 5.62(m,1H), 7.30–7.45(m,4H)
MS m/z(Pos. FAB): 495(M$^+$)

EXAMPLE 85

6-(2-Chlorophenyl)-11-methyl-3-(2-methylcyclohexyloxycarbonyl)-2,3,4,5-tetrahydro-8H-pyrido[4',3':4,5]-thieno[3,2-f][1,2,4]triazolo[4,3-a][1,4]diazepine

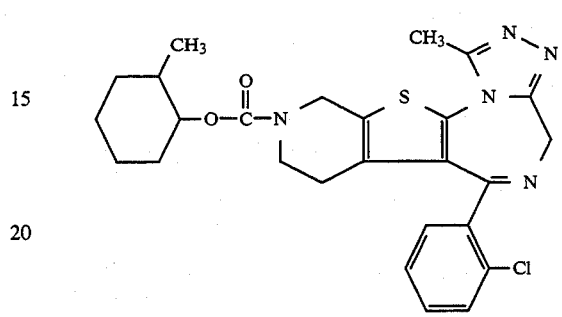

6-(2-Chlorophenyl)-11-methyl-3-(3-methylcyclohexyloxycarbonyl)-2,3,4,5-tetrahydro-8H-pyrido[4',3':4,5]-thieno[3,2-f][1,2,4]triazolo[4,3-a][1,4]diazepine

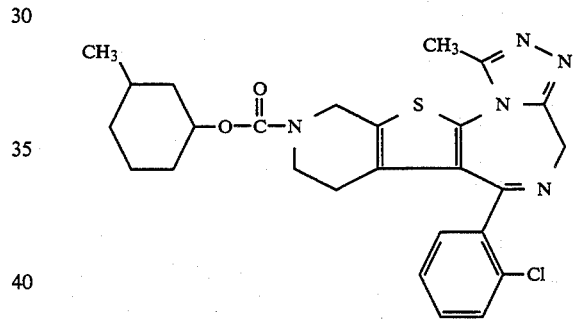

6-(2-Chlorophenyl)-11-methyl-3-(4-methylcyclohexyloxycarbonyl)-2,3,4,5-tetrahydro-8H-pyrido[4',3':4,5]-thieno[3,2-f][1,2,4]triazolo[3,2-a][1,4]diazepine

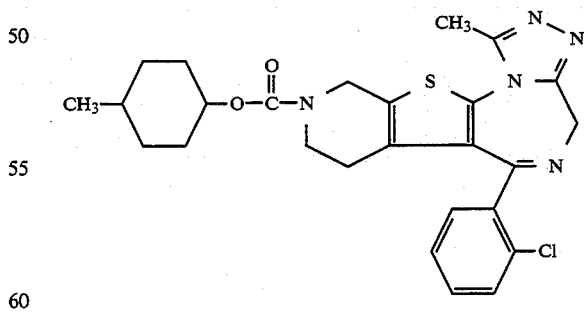

The above compounds had all the same NMR values as indicated below.

$^1$H-NMR(90 MHz, CDCl$_3$) δ: 0.7–1.0(d,3H), 1.0–2.2(m,11H), 2.7(s,3H), 3.0–4.0(m,2H), 4.0–4.9(m,1+1+2H), 5.3–5.8(m,1H), 7.4(m,4H)
MS m/z(Pos. FAB): 510

PREPARATORY EXAMPLE 30

3-Cyclopropylpropionic acid

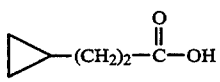

100 ml of methanol, 100 ml of tetrahydrofuran and 2 g of 10% palladium-carbon (containing 50% water) were added to 5.06 g of ethyl 3-cyclopropylacrylate, followed by hydrogenation reaction overnight at normal temperature and normal pressure conditions. The catalyst was removed by filtration and the solvent was distilled off. 20 ml of methanol, 20 ml of tetrahydrofuran, 10 ml of water and 7 g of sodium hydroxide were added to the residue and agitated at 80° C. for 3.5 hours. The solvent was distilled off, to which water was added, followed by washing with ethyl acetate. A hydrochloric acid aqueous solution was added to the resultant aqueous phase under ice-cooling conditions to adjust the pH to 3, followed by extraction with chloroform under slating-out conditions and drying with anhydrous magnesium sulfate. This was filtered and, after removal of the solvent by distillation, the resulting residue was subjected to silica gel column chromatography (developing solvent: dichloromethane) to obtain 1.80 g of the intended compound.

$^1$H-NMR(90 MHz, CDCl$_3$) δ: 0.65–1.1(m,2H), 1.1–1.85(m,5H), 2.33(t,J=7.2 Hz,2H), 8.9(bs,1H)

EXAMPLE 86

6-(2-Chlorophenyl)-3-(3-cyclopropyl)propionyl)-11-dimethyl-2,3,4,5-tetrahydro-8H-pyrido[4',3':4,5]-thieno[3,2-f][1,2,4]triazolo[4,3-a][1,4]diazepine

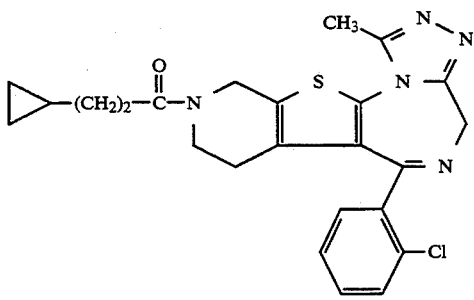

50 mg of 3-cyclopropylpropionic acid, 120 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine and 60 mg of 1-hydroxybenzotriazole.-monohydrate were dissolved in 8 ml of N,N-dinmethylformamide, to which 80 mg of N,N'-dicyclohexylcarbodiimide was added under ice-cooling conditions. After agitation for about 10 minutes, the mixture was further agitated overnight at 4° C. Thereafter, it was agitated at room temperature for about 1 hour, after which the solvent was distilled off. A saturated sodium hydrogencarbonate aqueous solution was added to the distilled product, which was extracted with chloroform and dried with anhydrous magnesium sulfate. The solution was filtered and the solvent was distilled off, after which the residue was subjected to silica gel column chromatography (developing solvent: dichloromethane:methanol=99:1), thereby obtaining 100 mg of the intended compound.

$^1$H-NMR(90 MHz, CDCl$_3$) δ: 0.7–1.05(m,3H), 1.05–2.4(m,6H), 2.27(t,J=7 Hz,2H), 2.67(s,3H), 2.8–5.9(m,6H), 7.1–7.55(m,4H)

EXAMPLE 87

6-(2-Chlorophenyl)-3-cinnamoyl-11-methyl-2,3,4,5-tetrahydro-8H-pyrido[4',3':4,5]thieno[3,2-f][1,2,4]triazolo[4,3-f][1,4]diazepine

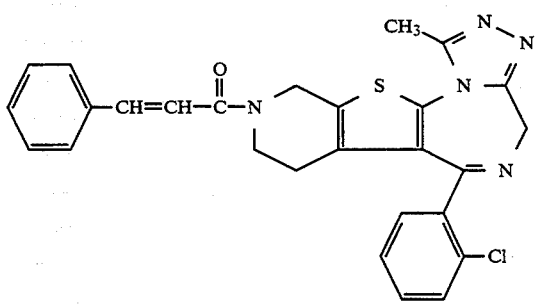

80 mg of cinnamoyl chloride was dissolved in 8 ml of N,N-dimethylformamide, into which 4 ml of an N,N-dimethylformamide solution of 120 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine and 160 mg of triethylamine was dropped at −60° C., followed by agitation for 30 minutes as it is. After removal of the solvent by distillation, a saturated sodium hydrogencarbonate aqueous solution was added, followed by extraction with chloroform and drying with anhydrous magnesium sulfate. This was filtered off and the solvent was distilled off. The resultant residue was subjected to silica gel column chromatography (developing solvent: methanol:dichloromethane=1:99) to obtain 110 mg of the intended compound (yield 68%).

$^1$H-NMR(CDCl$_3$) δ: 1.2–2.6(m,2H), 2.48(s,3H), 2.8–5.9(m,6H), 6.74(t,J=15.1 Hz,1H), 7.1–7.7(m,9H), 7.64(d,J=15.1 Hz,1H)

MS m/z(Pos. FAB): 500(M+H)+

EXAMPLE 88

6-(2-Chlorophenyl)-11-methyl-3-(2-methylcyclopropanecarbonyl)-2,3,4,5-tetrahydro-8H-pyrido[4,',3':4,5]thieno[3,2-f][1,2,4]triazolo[4,3-a][1,4diazepine

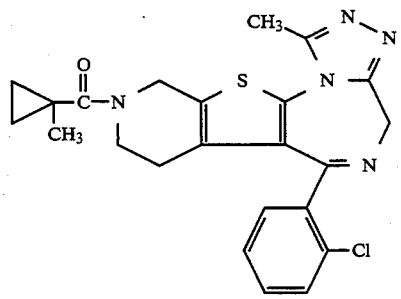

50 mg of 2-methylcyclopropanecarboxylic acid, 130 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine and 70 mg of 1-hydroxybenzotriazole.-monohydrate were dissolved in 8 ml of N,N-dimethylformamide, to which 90 mg of N,N'-dicyclohexylcarbodiimide was added under ice-cooling conditions, followed by agitation for about 10 minutes. Thereafter, agitation was continued at 4° C. overnight and then at room temperature for 1 hour. After removal of the solvent by distillation, a saturated sodium hydrogencarbonate aqueous solution was added, followed by extraction with chloroform and drying with anhydrous magnesium sulfate. This was filtered off and the solvent was distilled off, followed by subjecting the resultant residue to silica gel column chromatography (developing solvent: dichloromethane:methanol=99:1) to obtain 120 mg of the intended compound (yield 76%).

$^1$H-NMR(CDCl$_3$) δ: 0.4–0.72(m,1H), 0.72–1.0(m,1H), 1.26(s,3H), 1.4–2.4(m,2H), 2.68(s,3H), 2.9–5.9(m,6H), 7.1–7.7(m,4H)

MS m/z(Pos. FAB): 452(M+H)+

EXAMPLE 89

6-(2-Chlorophenyl)-11-methyl-3-phenylacetyl-2,3,4,5-tetrahydro-8H-pyrido[4',3':4,5]thieno[3,2-f][1,2,4-triazolo[4,3-a][1,4]diazepine

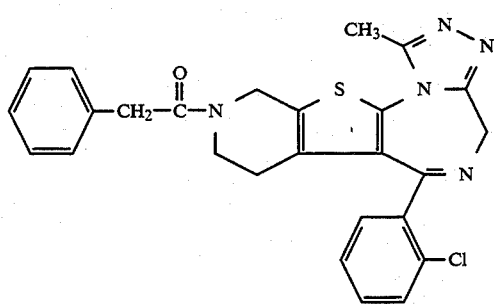

120 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine and 160 ml of triethylamine were dissolved in 4 ml of N,N-dimethylformamide, which was dropped into 5 ml of an N,N-dimethylformamide solution dissolving 60 mg of phenylacetic acid chloride at −60° C. After completion of the reaction, the solvent was distilled off from the reaction solution, to which a saturated sodium hydrogencarbonate solution was added, followed by extraction with chloroform and drying with anhydrous magnesium sulfate. This was filtered off and the solvent was distilled off, after which the resultant residue was subjected to silica gel column chromatography (developing solvent: dichloromethane:methanol=99:1) to obtain 110 mg of the intended compound. (yield 69%).

$^1$H-NMR(CDCl$_3$) δ: 1.0–2.6(m,2H), 2.61 and 2.66(each s, total 3H), 2.8–6.0(m,6H), 3.69 and 3.77(each bs, total 2H), 6.8–7.7(m,9H)

MS m/z(Pos. FAB): 488(M+H)+

EXAMPLE 90

6-(2-Chlorophenyl)-11-methyl-3-(3-methylcrotonoyl)-2,3,4,5-tetrahydro-8H-pyrido[4',3':4,5]thieno[3,2-f][1,2,4]triazolo[4,3-a][1,4]diazepine

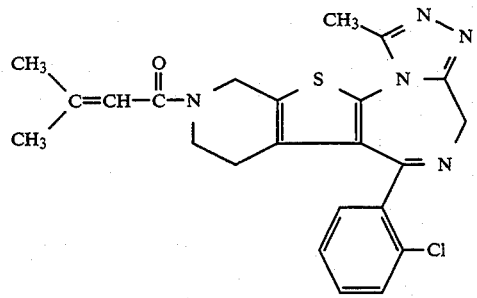

120 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine and 160 mg of triethylamine were dissolved in 4 ml of N,N-dimethylformamide, which was dropped into 5 ml of an N,N-dimethylformamide solution dissolving 50 mg of 3-methylcrotonic acid chloride at −60° C. After completion of the reaction, the reaction solution was distilled off, to which a saturated sodium hydrogencarbonate aqueous solution was added, followed by extraction with chloroform and drying with anhydrous magnesium sulfate. This was filtered off and the solvent was also distilled off, after which the resultant residue was subjected to silica gel column chromatography (developing solution: dichloromethane:methanol=99:1) to obtain 130 mg of the intended compound.

$^1$H-NMR(CDCl$_3$) δ: 1.0–2.5(m,8H), 2.70(s,3H), 2.8–5.9(m,6H), 6.73(bs,1H), 7.1–7.6(m,4H)

MS m/z(Pos. FAB): 452(M+H)+

EXAMPLE 91

6-(2-Chlorophenyl)-11-methyl-3-((trans)-2-phenylcyclopropanecarbonyl-2,3,4,5-tetrahydro-8H-pyrido[4',3':4,5]thieno[3,2-f][1,2,4]triazolo[4,3-a][1,4]diazepine

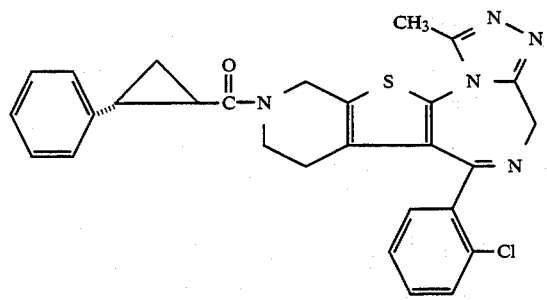

70 mg of (trans)-2-phenyl-1-cyclopropanecarboxylic acid, 120 mg of 6-(2-chlorophenyl)-11-methyl-2,3,4,5-tetrahydro-8H-pyrido[4',3':4,5]thieno[3,2-f][1,2,4]triazolo[4,3-a][1,4]diazepine and 60 mg of 1-hydroxybenzotriazole.monohydrate were dissolved in 12 ml of N,N-dimethylformamide, to which 80 mg of N,N'-dicyclohexylcarbodiimide was added under ice-cooling conditions. After agitation for about 10 minutes, the mixture was further agitated overnight at 4° C. and then at room temperature for 1 hours. After removal of the solvent by distillation, a saturated sodium hydrogencarbonate aqueous solution was added, followed by extraction with chloroform and drying with anhydrous magnesium sulfate. This sulfate was removed by filtration and the solvent was distilled off. The resultant residue was subjected to silica gel column chromatography (developing solvent: dichloromethane:methanol=99:1) to obtain 160 mg of the intended compound.

$^1$H-NMR(CDCl$_3$) δ: 1.4–2.8(m,6H), 2.66(s,3H), 2.8–5.8(m,6H), 6.5–7.7(m,9H)

MS m/z(Pos. FAB): 514(M+H)$^+$

EXAMPLE 92

6-(2-Chlorophenyl)-11-methyl-3-(α-methylcinnamoyl)-2,3,4,5-tetrahydro-8H-pyrido[4',3':4,5]thieno[3,2-f][1,2,4]triazolo[4,3-a][1,4]diazepine

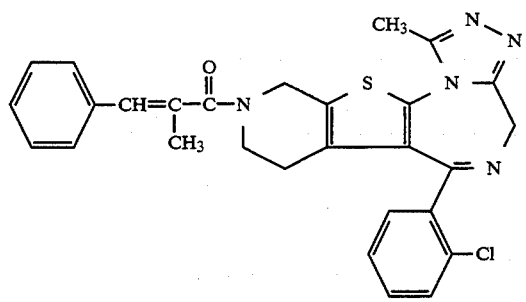

$^1$H-NMR(CDCl$_3$) δ: 1.7–2.5(m,2H), 2.14(d,J=1.4 Hz,3H), 2.72(s,3H), 2.8–5.9(m,6H), 6.87(q,J=4 Hz,1H), 7.0–7.7(m,9H)

MS m/z(Pos. FAB):

EXAMPLE 93

6-(2-Chlorophenyl)-11-methyl-3-(4-pyridylthio)acetyl-2,3,4,5-tetrahydro-8H-pyrido[4',3':4,5]thieno[3,2-f][1,2,4]triazolo[4,3-a][1,4]diazepine

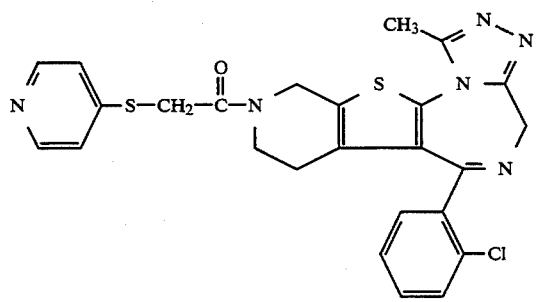

$^1$H-NMR(CD$_3$OD-CDCl$_3$) δ: 1.4–2.6(m,2H), 2.68(s,3H), 2.8–5.9(m,6H), 3.82(bs,2H), 7.05–7.6(m,6H), 8.1–8.6(m,2H)

MS M/z(Pos. FAB): 521((M+H)$^+$

EXAMPLE 94

6-(2-Chlorophenyl)-11-methyl-3-(3-phenylpropionyl)-2,3,4,5-tetrahydro-8H-pyrido[4',3':4,5]thieno[3,2-f][1,2,4]triazolo[4,3-a][1,4]diazepine

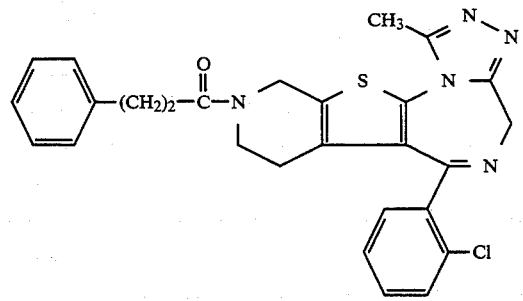

$^1$H-NMR(CDCl$_3$) δ: 1.0–2.3(m,4H), 2.66(s,3H), 2.65–3.15(m,2H), 2.8–5.9(m,6H), 6.65–7.65(m,9H)

MS m/z(Pos. FAB): 502((M+H)$^+$

EXAMPLE 95

6-(2-Chlorophenyl)-11-methyl-3-[3-(3-pyridyl)acryloyl]-2,3,4,5-tetrahydro-8H-pyrido[4',3':4,5]-thieno[3,2-f][1,2,4]triazolo[4,2-a][1,4]diazepine

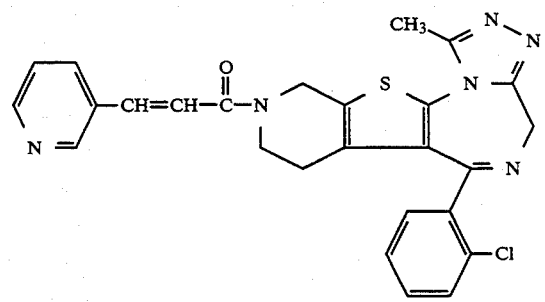

$^1$H-NMR(CDCl$_3$) δ: 1.5–2.5(m,2H), 2.68(s,3H), 3.0–5.8(m,6H), 6.83(bd,J=15.5 Hz,1H), 7.15–7.9(m,6H), 7.60(d,J=15.5 Hz,1H), 8.3–8.5(m,1H), 8.64(bs,1H)

MS m/z(Pos. FAB): 501((M+H)$^+$

EXAMPLE 96

6-(2-Chlorophenyl)-3-(3-cyclohexylpropionyl)-11-methyl-2,3,4,5-tetrahydro-8H-pyrido[4',3':4,5]-thieno[3,2-f][1,2,4]triazolo[4,3-a][1,4]diazepine

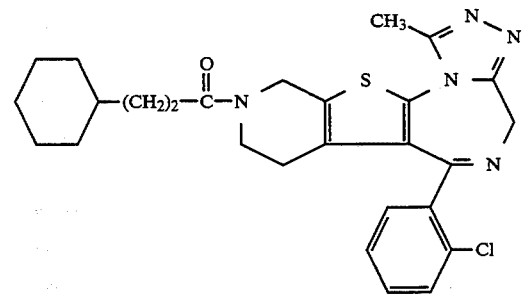

$^1$H-NMR(CDCl$_3$) δ: 0.6–2.5(m,15H), 2.28(bt,J=8 Hz,2H), 2.66(s,3H), 2.8–5.9(m,6H), 7.114 7.6(m,4H)

MS m/z(Pos. FAB): 508((M+H)$^+$

EXAMPLE 97

6-(2-Chlorophenyl)-3-(4-fluorophenyl)acetyl-11-methyl-2,3,4,5-tetrahydro-8H-pyrido[4',3':4,5]thieno[3,2-f][1,2,4]triazolo[4,a3-a][1,4]diazepine

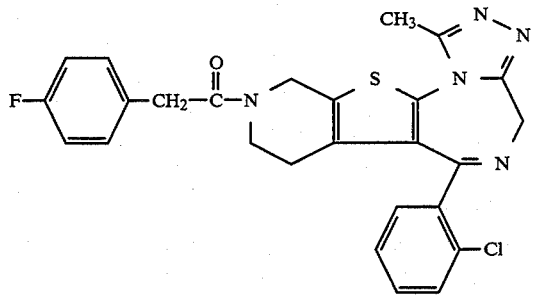

$^1$H-NMR(CDCl$_3$) δ: 1.0–2.4(m,2H), 2.66(s,3H), 2.8–5.9(m,6H), 3.65(bs,2H), 6.65–7.6(m,8H)
MS m/z(Pos. FAB): 506((M+H)$^+$

EXAMPLE 98

6-(2-Chlorophenyl)-3-(4-cyanobutanoyl)-11-methyl-2,3,4,5-tetrahydro-8H-pyrido[4',3':4,5]thieno[3,2-f][1,2,4]triazolo[4,3-a][1,4]diazepine

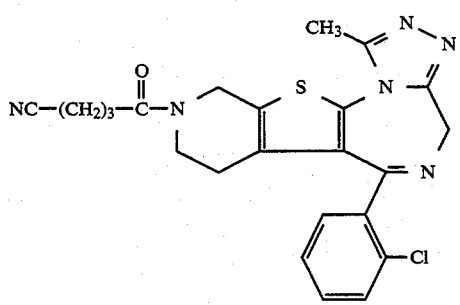

$^1$H-NMR(CDCl$_3$) δ: 1.4–2.3(m,4H), 2.3–2.65(m,4H), 2.67(s,3H), 2.8–5.8(m,6H), 7.1–7.6(m,4H)
MS m/z(Pos. FAB): 465((M+H)$^+$

PREPARATORY EXAMPLE 31

Ethyl tetrahydropyrane-Δ 4,a-acetate

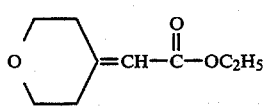

1.2 g (30 mmols) of sodium hydride was added to 100 ml of a dimethylformamide solution of 6.72g (30 mmols) of diethylphosphonoethyl acetate under ice-cooling conditions, and was agitated for 10 minutes. 2.5 g (25 mmols) of tetrahydro-4H-pyran-4-one was further added to the mixture under ice-cooling conditions and was returned to room temperature, followed by agitation at 80° C. for 2 hours. After completion of the reaction, ethyl acetate was added, followed by washing with a saturated saline solution and drying with magnesium sulfate. This was concentrated under reduced pressure and the resultant residue was subjected to silica gel column chromatography (elution solvent: hexane:ethyl acetate=9:1) thereby obtaining 4.2 g of the intended compound as a light yellow oily substance.

$^1$H-NMR(CDCl$_3$) δ: 1.3(t,J=7,2 Hz,3H), 2.0–2.3(m,2H), 3.0(bs,2H), 3.8(t,J=5.4 Hz,2H), 4.0–4.3(m,2H), 4.1(q,J=7.2 Hz,2H), 5.6(bs,1H)

PREPARATORY EXAMPLE 32

Ethyl 4-tetrahydropyranylacetate

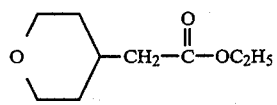

2.0 g of ethyl tetrahydropyran-Δ 4,a-acetate was dissolved in 50 ml of methanol, to which 10% palladium-carbon was added, followed by hydrogenation for 3 hours. After removal of the catalyst by filtration, the reaction mixture was concentrated under reduced pressure to obtain 1.6 g of the intended compound.

$^1$H-NMR(CDCl$_3$) δ: 1.1–2.3(m,7H), 1.3(t,J=7,2 Hz,3H), 3.2–3.6(td,J=12,6 Hz,2.9 Hz,2H), 3.8–4.3(m,2H), 4.1(q,J=7.2 Hz,2H)

PREPARATORY EXAMPLE 33

4-Tetrahydropyranylacetic acid

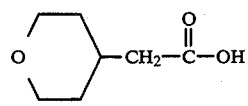

20 ml of methanol, 10 ml of water and 1 g of sodium hydroxide were added to 0.9 g of ethyl 4-tetrahydropyranylacetate and agitated at 80° C. for 1 hour. The solvent was removed by distillation, to which water was added. After washing with ethyl acetate, a hydrochloric acid aqueous solution was added to the resultant aqueous phase to an extract of pH of 3, followed by extraction with chloroform under salting-out conditions and drying with anhydrous magnesium sulfate. This was removed by filtration and the solvent was distilled off, thereby obtaining 0.87 g of a crude intended compound.

$^1$H-NMR(CDCl$_3$) δ: 1.0–2.4(m,5H), 2.28(bd,J=6.5 Hz,2H), 3.37(td,J=11.5 Hz,2.9 Hz,2H), 3.7–4.1(m,2H), 7.85(bs,1H)

EXAMPLE 99

6-(2-Chlorophenyl)-11-methyl-3-(tetraydropyran-4-yl)-acetyl-2,3,4,5-tetrahydro-8H-pyrido[4',3':4,5]-thieno[3,2-f][1,2,4]triazolo[3,2-a][1,4]diazepine

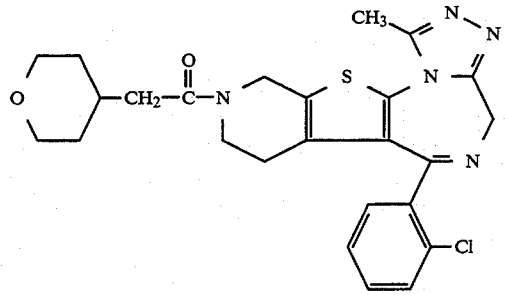

$^1$H-NMR(CD$_3$OD-CDCl$_3$) δ: 0.9–2.4(m,9H), 2.67(s,3H), 2.8–5.9(m,10H), 7.1–7.5(m,4H)
MS m/z(Pos. FAB): 496((M+H)$^+$

PREPARATORY EXAMPLE 34

Tetrahydropyran-Δ 4,a-acetic acid

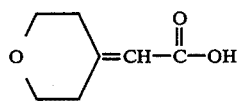

20 ml of methanol, 10 ml of water and 1 g of sodium hydroxide were added to 0.8 g of ethyl tetrahydropyran-Δ 4,a-acetate and agitated at 80° C. for 2 hours. After removal of the solvent by distillation, water was added to the mixture, followed by washing with ethyl acetate. A hydrochloric acid aqueous solution was added to the aqueous phase to render it acidic, followed by extraction with chloroform under salting-out conditions and drying with anhydrous magnesium sulfate. This was filtered off and the solvent was distilled off, followed by subjecting the resultant residue to silica gel column chromatography (developing solvent: dichloromethane) thereby obtaining 0.17 g of the intended compound (yield 25%).

$^1$H-NMR(CD$_3$OD-CDCl$_3$) δ: 2.34(bt,J=5.4 Hz,2H), 2.98(bt,J=5.4 Hz,2H), 3.5-3.95(m,4H), 5.66(bs,1H), 8.45(bs,1H)

EXAMPLE 100

6-(2-Chlorophenyl)-11-methyl-3-(tetrahydropyran-Δ 4,a-acetyl-2,3,4,5-tetrahydro-8H-pyrido[4',3':4,5]-thieno[3,2-f][1,2,4]triazolo[4,3-a][1,4]diazepine

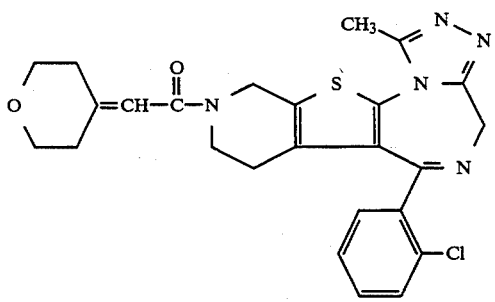

$^1$H-NMR(CDCl$_3$) δ: 1.4-2.5(m,2H), 2.1-2.41(m,2H), 2.41-2.8(m,2H), 2.67(s,3H), 2.8-5.9(m,6H), 3.45-3.9(m,4H), 5.72(bs,1H), 7.15-7.5(m,6H)
MS m/z(Pos. FAB): 494((M+H)+

EXAMPLE 101

6-(2-Chlorophenyl)-3-[(trans)-3-cyclopropylacryloyl]-11-methyl-2,3,4,5-tetrahydro-8H-pyrido[4',3':4,5]-thieno[3,2-f][1,2,4]triazolo[4,3-a][1,4]diazepine

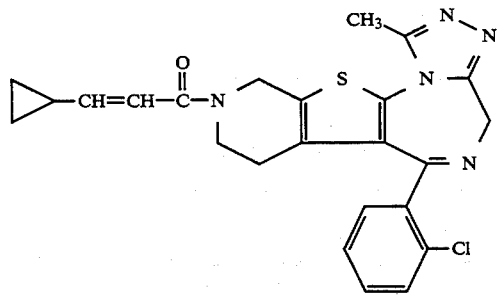

$^1$H-NMR(CDCl$_3$) δ: 0.4-1.15(m,4H), 1.2-2.6(m,3H), 2.66(s,3H), 2.8-6.0(m,6H), 6.13(d,J=21.6 Hz,1H), 6.25(dd,J=21.6, 14.4 Hz,1H), 7.1-7.5(m,4H)
MS m/z(Pos. FAB): 464((M+H)+

EXAMPLE 102

6-(2-Chlorophenyl)-3-[(trans)-3-cyclopropyl]acryloyl-8,11-dimethyl-2,3,4,5-tetrahydro-8H-pyrido[4',3':4,5]-thieno[3,2-f][1,2,4]triazolo[4,3-a][1,4]diazepine

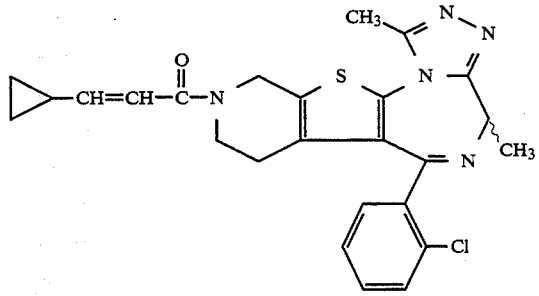

(1) Preparation of ethyl (trans)-3-cyclopropylacrylate

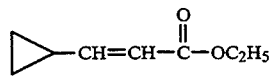

38.38 g of ethyl diethylphosphonoacetate was dissolved in 300 ml of N,N-dimethylformamide, to which 6.85 g of 60% sodium hydride at 0° C., followed by agitation at room temperature for 30 minutes and dropping 10 g of cyclopropanealdehyde at 0° C. After agitation at room temperature for 2 hours, iced water was added, followed by extraction with ether, washing with water and drying with anhydrous magnesium sulfate. This was removed by filtration and a concentrated residue was subjected to silica gel column chromatography (developing solvent: ethyl acetate:hexane=2:98), thereby obtaining 11.18 g of the intended compound as a trans product (yield 60%).

$^1$H-NMR(CDCl$_3$) δ: 0.4-1.1(m,4H), 1.26(t,J=7.2 Hz,3H), 1.3-1.8(m,1H), 4.13(q,J=7.2 Hz,2H), 5.82(d,J=15.5 Hz,1H), 6.37(dd,J=15.5 Hz,10.1 Hz,1H)

(2) Preparation of (trans)-3-cyclopropylacrylic acid

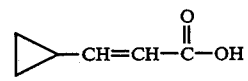

100 ml of methanol, 50 ml of water and 6.4 g of sodium hydroxide were added to 11.18 g of ethyl (trans)-3-cyclopropylacrylate obtained in the above method and subjected to reaction at 80° C. for 1.5 hours. After concentration, concentrated hydrochloric acid was added so as to render the reaction mixture acidic, followed by extraction with chloroform, washing with a saturated saline solution and drying with anhydrous magnesium sulfate. This sulfate was removed by filtration and the filtrate was concentrated to obtain 8.82 g of the intended compound (yield 99%).

$^1$H-NMR(CDCl$_3$) δ: 0.3-1.2(m,4H), 1.2-1.9(m,1H), 5.83(d,J=15.1 Hz,1H), 6.47(dd,J=15.1 Hz,6.5 Hz,1H), 9.06(bs,1H)

(3) 6-(2-Chlorophenyl)-3-[(trans)-3-cyclopropyl]acryloyl-8,11-dimethyl-2,3,4,5-tetrahydro-8H- pyrido[4',3':4,5]thieno[3,2-f][1,2,4]triazolo[4,3-a][1,4]diazepine

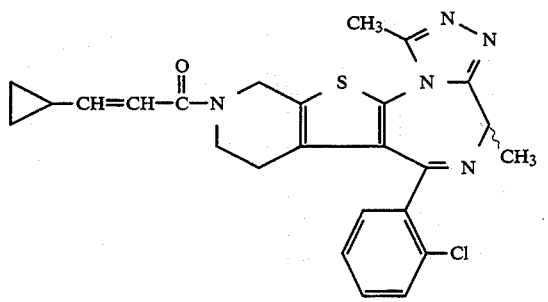

90 mg of (trans)-3-cyclopropylacrylic acid, 120 g of 1-hydroxybenzotriazole.monohydrate and 240 mg of 6-(2-chlorophenyl)-8,11-dimethyl-2,3,4,5-tetrahydro-8H-pyrido[4,',3':4,5]thieno[3,2-f][1,2,4]triazolo[4m3-a][1,4]-diazepine were dissolved in 12 ml of N,N-dimethylformamide, to which 160 mg of 1,3-dicyclohexylcarbodiimide was added under ice-cooling conditions, followed by agitation at 4° C. for 9 hours and then at room temperature for 1 hour. After concentration, a saturated sodium hydrogencarbonate aqueous solution was added, followed by extraction with chloroform and drying with anhydrous magnesium sulfate. This was removed by filtration and the resultant filtrate was concentrated, followed by the resultant residue to silica gel column chromatography (developing solvent: solvent-:dichloromethane=1:99) to obtain 240 mg of the intended compound (yield 80%).

$^1$H-NMR(CDCl$_3$) δ: 0.4–1.1(m,4H), 1.35–2.0(m,2H), 2.0–2.6(m,1H), 2.09(d,J=6.8 Hz,3H), 2.65(s,3H), 2.8–4.1(m,2H), 4.1–5.3(m,2H), 4.26(q,J=6.8 Hz,1H), 6.15(d,J=19.8 Hz,1H), 6.31(dd,J=19.8 Hz,15.1 Hz,1H), 7.1–7.55 (m,4H)

MS m/z(Pos. FAB): 478((M+H)+

EXAMPLE 103

6-(2-Chlorophenyl)-3-cyclobutanecarbonyl-8,11-dimethyl-2,3,4,5-tetrahydro-8H-pyrido[4',3':4,5]-thieno[3,2-f][1,2,4]triazolo[4,3-a][1,4]diazepine

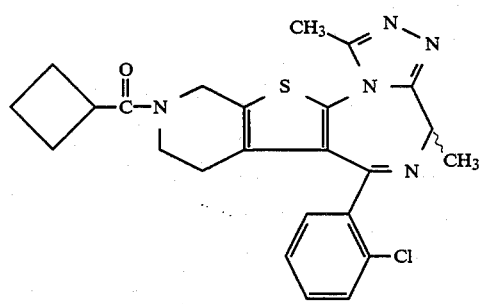

40 mg of cyclobutanecarboxylic acid and 120 mg of 6-(2-chlorophenyl)-8,11-dimethyl-2,3,4,5-tetrahydro-8H-pyrido[4',3':4,5]thieno[3,2-f][1,2,4]triazolo[4,3-a][1,4]diazepine were dissolved in 8 ml of N,N-dimethylformamide, to which 80 mg of 1,3-dicyclohexylcarbodiimide was added under ice-cooling conditions, followed by agitation at 4° C. for 9 hours and then at room temperature for 1 hour. After concentration, a saturated sodium hydrogencarbonate aqueous solution was added, followed by extraction with chloroform and drying with anhydrous magnesium sulfate. This was subjected to filtration and concentrated, and the resultant residue was subjected to silica gel column chromatography (developing solvent: methanol:dichloromethane=1:99) to obtain 120 mg of the intended compound (yield 82%).

$^1$H-NMR(CDCl$_3$) δ: 1.2–2.8(m,8H), 2.09(d,J=6.8 Hz,3H), 2.65(s,3H), 2.85–3.8(m,3H), 3.8–4.6(m,2H), 4.25(q,J=6.8 Hz,1H), 4.8–5.3(m,1H), 7.0–7.6(m,4H)

MS m/z(Pos. FAB): 466((M+H)+

EXAMPLE 104

6-(2-Chlorophenyl)-3-cyclopentanecarbonyl-8,11-dimethyl-2,3,4,5-tetrahydro-8H-pyrido[4',3':4,5]-thieno[3,2-f][1,2,4]triazolo[4,3-a][1,4]diazepine

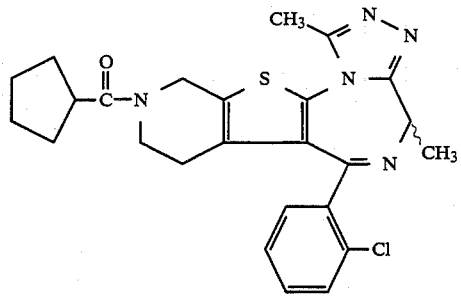

50 mg of cyclopentanecarboxylic acid and 120 mg of 6-(2-chlorophenyl)-8,11-dimethyl-2,3,4,5-tetrahydro-8H-pyrido[4',3':4,5]thieno[3,2-f][1,2,4]triazolo[4,3-a][1,4]diazepine were dissolved in 8 ml of N,N-dimethylformamide, to which 80 mg of 1,3-dicyclohexylcarbodiimide was added under ice-cooling conditions, followed by agitation at 4° C. for 9 hours and then at room temperature for 1 hour. After concentration, a saturated sodium hydrogencarbonate aqueous solution was added, followed by extraction with chloroform and drying with anhydrous magnesium sulfate. This was subjected to filtration and concentrated, and the resultant residue was subjected to silica gel column chromatography (developing solvent: methanol:dichloromethane=1:99) to obtain 110 mg of the intended compound (yield 73%).

$^1$H-NMR(CDCl$_3$) δ: 1.1–2.1(m,8H), 2.10(d,J=6.8 Hz,3H), 2.1–3.1(m,1H), 2.66(s,3H), 3.1–4.0(m,2H), 4.0–5.3(m,2H), 4.26(q,J=6.8 Hz,1H), 7.1–7.6 (m,4H)

MS m/z(Pos. FAB): 480((M+H)+

PREPARATORY EXAMPLE 35

N-(Benzyloxycarbonyl)-3-pyrrolidinol

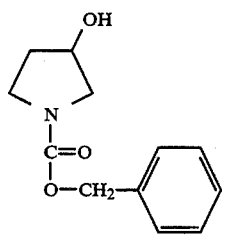

30 mg of 3-pyrrolidinol was dissolved in 500 ml of chloroform, to which 53 mg of triethylamine was added, followed by gradually dropping 52 ml of benzyloxycarbonyl chloride at room temperature. After completion of the reaction, the reaction solution was poured into water and extracted with chloroform. The solvent was distilled off under reduced pressure and the resultant residue was purified by column chromatography (eluting solvent: hexane-ethyl acetate) to obtain 70.67 g of the intended compound.

¹H-NMR(90 MHz, CDCl₃) δ: 1.7–2.1(m,2H), 2.8–3.2(m,1H), 3.2–3.7(m,4H), 4.2–4.5(m,1H), 5.1(s,2H), 7.3(s,5H)

PREPARATORY EXAMPLE 36

N-(Benzyloxycarbonyl)-3-pyrrolidone

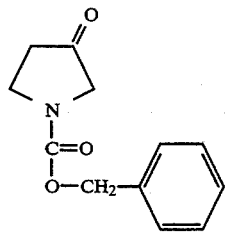

150 ml of oxalic acid chloride was added to 2 liters of dichloromethylene. 245 ml of dimethylsulfoxide was gradually added at −70° to −50° C. in a stream of argon. 70.67 g of N-(N-benzyloxycarbonyl)-3-pyrrolidinol dissolved in dichloromethylene was dropped. After gradual dropping of 720 ml of triethylamine, the mixture was raised to room temperature. After completion of the reaction, the reaction solution was poured into water and extracted with dichloromethylene, followed by removal of the solvent by distillation under reduced pressure. The residue was purified by column chromatography (eluting solvent: hexane-ethyl acetate), thereby obtaining 66.55 g of the intended compound).

¹H-NMR(90 MHz, CDCl₃) δ: 2.6(t,J=7.5 Hz,2H), 3.7–4.0(m,4H), 5.12(s,2H), 7.3(s,5H)

PREPARATORY EXAMPLE 37

2-Amino-3-(2-chlorobenzoyl)-5-benzyloxycarbonyl-4,6-dihydro-thieno[2,3-c]pyrrole

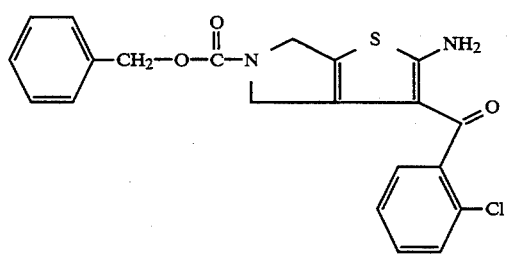

66.55 g of the compound obtained in Preparatory Example 36. 54.3 g of 2-chlorocyanoacetophenone and 9.9 g of sulfur were dissolved in 300 ml of dimethylformamide, to which 45 ml of triethylamine was added, followed by heating at 60° C. for 2 hours. After completion of the reaction, the solvent was distilled off under reduced pressure and the resultant residue was purified by column chromatography (eluting solvent: hexane-ethyl acetate), thereby obtaining 68.4 g of the intended compound.

¹H-NMR(90 MHz, CDCl₃) δ: 3.4–3.9(m,2H), 4.3–4.6(m,2H), 4.93 and 5.02(each s, total 2H), 70–7.6(m,11H)

PREPARATORY EXAMPLE 38

2-Bromoacetylamino-3-(2-chlorobenzoyl)-5-benzyloxycarbonyl-4,6-dihydro-thieno[2,3-c]pyrrole

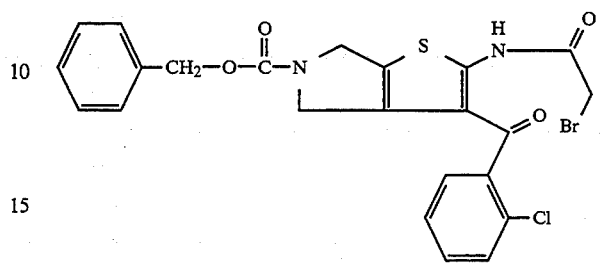

600 ml of toluene/150 ml water was added to 68.4 g of the compound obtained in Preparatory Example 37, to which 33.5 g of sodium hydrogencarbonate, followed by dropping 25 ml of bromoacetyl bromide at 60° C. After completion of the reaction, the reaction solution was poured into dichloromethylene and washed with water, followed by removal of the solvent by distillation under reduced pressure. The resultant residue was used for subsequent reaction as it is without any purification.

¹H-NMR(90 MHz, CDCl₃) δ: 3.5–3.95(m,2H), 4.08(s,2H), 4.3–4.7(m,2H), 5.03 and 5.07(each s, total 2H), 7.0–7.6(m,10H)

PREPARATORY EXAMPLE 39

2-Aminoacetylamino-3-(2-chlorobenzoyl)-5-benzyloxycarbonyl-4,6-dihydro-thieno[2,3-c]pyrrole

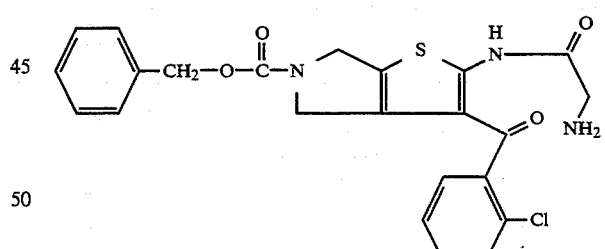

The compound obtaining Preparatory Example 38 was dissolved in 3.5 liters of ethyl acetate, which was saturated with ammonia gas. After introduction of the gas for 8 hours, insoluble inorganic matters were filtered off and the resultant filtrate was subjected to distillation under reduced pressure to remove the solvent, and the resultant crystals were collected by filtration to obtain 4.19 g of the intended compound.

¹H-NMR(90 MHz, CDCl₃) δ: 3.3–3.9(m,4H), 4.4–4.7(m,2H), 5.02 and 5.06(each s, total 2H), 7.0–7.5m,11H)

PREPARATORY EXAMPLE 40

5-(2-Chlorophenyl)-7-benzyloxycarbonyl-6,8-dihydro-1-3H,pyrrolo[4',3':4,5]thieno[3,2-f][1,4]diazepin-2-one

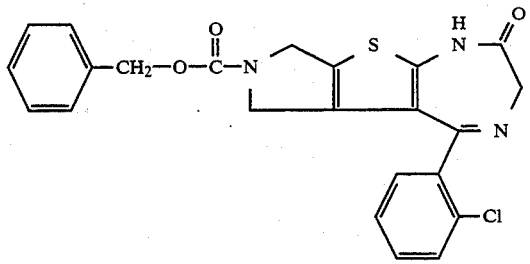

38.5 g of the compound obtained in Preparatory Example 39 was dissolved in 250 ml of benzene/500 ml pyridine, to which 5.2 ml of acetic acid was added, followed by removing produced water from the system while heating at 120° C. After completion of the reaction, the reaction solution as concentrated under reduced pressure and the resultant residue was purified by column chromatography (eluting solvent: hexane-ethyl acetate) to obtain 21.0 g of the intended compound.

$^1$H-NMR(90 MHz, CDCl$_3$) δ: 3.6–3.9(m,2H), 4.42(s,2H), 4.3–4.7(m,2H), 5.06(s,2H), 7.0–7.5(m,10H)

PREPARATORY EXAMPLE 41

5-(2-Chlorophenyl)-7-benzyloxycarbonyl-6,8-dihydro-1,3H-pyrrolo[4',3':4,5]thieno[3,2-f][1,4]diazepin-2-thione

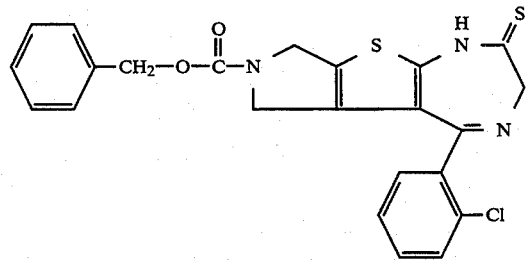

13.7 g of the compound obtained in Preparatory Example 40 was dissolved in 300 ml of toluene, to which 12.3 g of the Rhoson agent, [2,4-bis(4-methoxyphenyl)-1,3-dithia-2,4-diphosphetan-2,4-disulfide) was added, followed by heating at 80° C. for 15 minutes. After completion of the reaction, the solvent was distilled off under reduced pressure and the resultant residue was purified by column chromatography (elusion solvent: hexane-ethyl acetate) to obtain 9.3 g of the intended compound.

$^1$H-NMR(90 MHz, CDCl$_3$) δ: 3.5–3.9(m,2H), 4.3–4.7(m,4H), 5.0 and 5.06(each s, total 2H), 6.9–7.5(m,10H)

PREPARATORY EXAMPLE 42

3-Benzyloxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

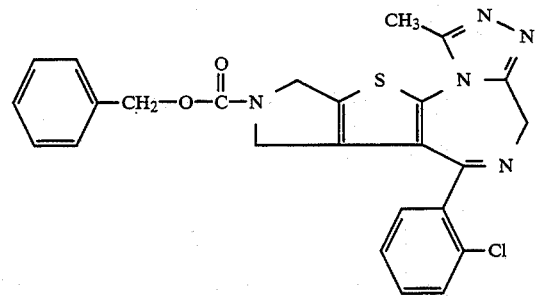

250 ml of methanol was added to 10.2 g of the compound obtained in Preparatory Example 41, to which 4.8 g of hydrazine monohydrate was added, followed by agitation at room temperature for 1 hour. After completion of the reaction, precipitated hydrazide was collected by filtration. 200 ml of triethyl ortho-acetate was added to it and heated at 80° C. for 40 minutes. After completion of the reaction, the reaction mixture was concentrated under reduced pressure and the resultant residue was purified by column chromatography (eluting solvent: benzene-acetone) to obtain 7.39 g of the intended compound.

$^1$H-NMR(90 MHz, CDCl$_3$) δ: 2.7(s,3H), 3.6–3.9(m,2H), 4.6–4.8(m,2H), 4.8–5.0(m,2H), 5.05 and 5.09(each s, total 2H), 7.0–7.5(m,9H)

PREPARATORY EXAMPLE 43

3H-5-(2-Chlorophenyl)-10-methyl-2,4-dihydro-2H,7H-pyrrolo[4',3':4,5]thieno[3,2-f][1,2,4]triazolo[4,3-a][1,4]diazepine

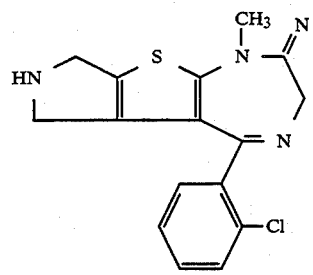

0.23 g of the compound obtained in Preparatory Example 42 was added 3 ml of dichloromethylene, to which 0.7 ml of iodotrimethylsilane, followed by agitation at room temperature. After completion of the reaction, methanol was added and the solvent was distilled off under reduced pressure. The resultant residue was purified by column chromatography (eluting solvent: dichloromethylene-methanol/ammonia solution) to obtain 0.1 g of the intended compound.

$^1$H-NMR(90 MHz, CDCl$_3$)δ: 2.7(s,3H), 3.6–3.9(m,2H), 4.5–4.7(m,2H), 4.8–5.2(m,2H), 7.0–7.6(m,4H)

EXAMPLE 105

3-(2'-Cyanoethyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

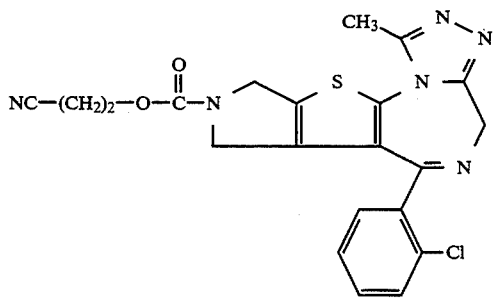

$^1$H-NMR(CDCl$_3$)δ: 2.67(t,J=7 Hz,1H), 2.75(t,J=7 Hz,1H), 2.75(s,3H), 3.64–3.90(m,2H), 4.25(t,J=7 Hz,1H), 4.31(t,J=7 Hz,1H), 4.64–4.82(m,2H), 4.80–5.12(m,2H), 7.26–7.46(m,4H)
MS m/z: 453

EXAMPLE 106

3-(3'-Butynyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

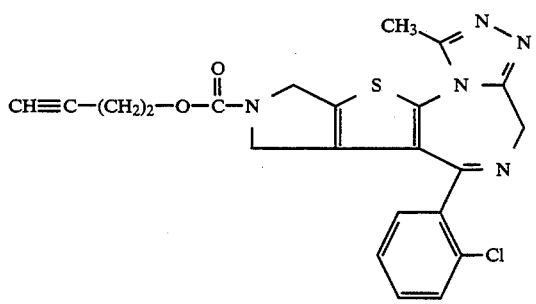

$^1$H-NMR(CDCl$_3$)δ: 2.00(t,J=7 Hz,1H), 2.46(dt,J=7 Hz,2 Hz,1H), 2.55(s,3H), 2.75(s,3H), 3.60–3.85(m,2H), 4.14(t,J=7 Hz,1H), 4.20(t,J=7 Hz,1H), 4.60–4.85(m,2H), 4.75–5.10(m,2H), 7.10–7.54(m,4H)
MS m/z: 452

EXAMPLE 107

3-[2-(Morpholin-4-yl)ethyl]-oxycarbonyl-5-(2-chlorophenyl)-10-methyl-2,4-dihydro-2H,7H-pyrrolo[4,',3':4,5]thieno[3,2-f][1,2,4]triazolo[4,3-a][1,4]diazepine

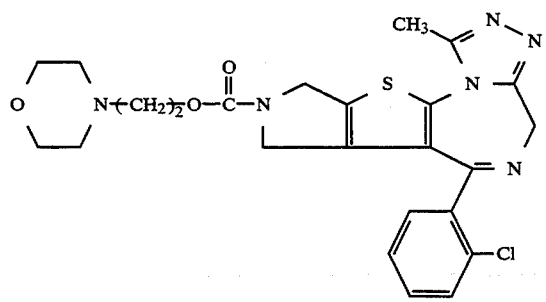

$^1$H-NMR(CDCl$_3$)δ: 2.20–2.85(m,6H), 2.76(s,3H), 3.50–3.90(m,6H), 4.20(t,J=7 Hz,1H), 4.28(t,J=7 Hz,1H), 4.55–4.80(m,2H), 4.80–5.15(m,2H), 7.20–7.55(m,4H)
MS m/z: 513

EXAMPLE 108

3-(3-Pyridylethyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

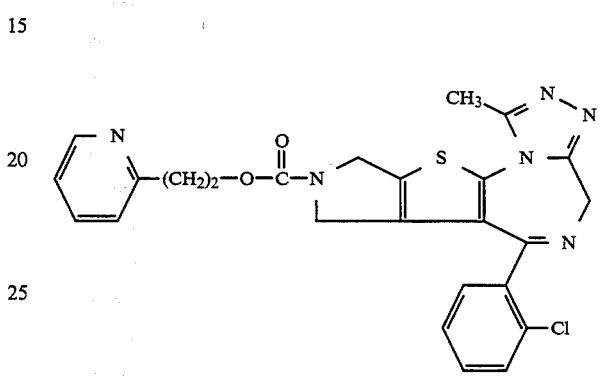

$^1$H-NMR(CDCl$_3$)δ: 2.72(s,3H), 3.04(t,J=7 Hz,1H), 3.12(t,J=7 Hz,1H), 3.48–3.85(m,2H), 4.30–4.80(m,4H), 4.70–5.18(m,2H), 4.70–5.18(m,2H), 6.95–7.70(m,7H), 8.40–8.56(m,1H)
MS m/z: 505

EXAMPLE 109

3-(Tetrahydropyran-4-yl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

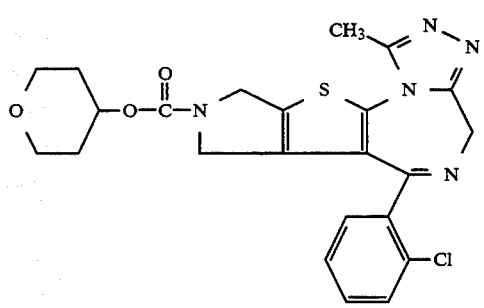

$^1$H-NMR(CDCl$_3$)δ: 1.40–2.30(m,4H), 2.74(s,3H), 3.32–4.05(m,7H), 4.60–5.08(m,4H), 7.20–7.56(m,4H)
MS m/z: 484

EXAMPLE 110

3-(3'-butyn-2'-yl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

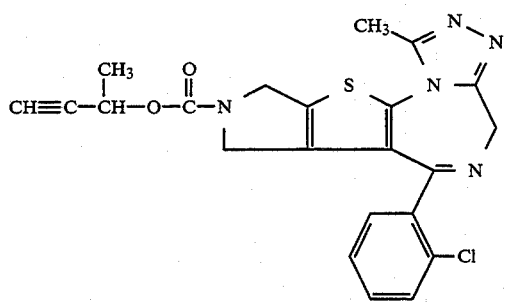

¹H-NMR(CDCl₃)δ: 1.54(d,J=7 Hz,3H), 2.48(d,J=2 Hz,1H), 2.72(s,3H), 3.60–3.86(m,2H), 4.60–4.82(m,2H), 4.78–5.10(m,2H), 5.18–5.46(m,1H), 7.12–7.54(m,4H)
MS m/z: 452

EXAMPLE 111

3-(3'-Morpholino-3'-oxopropyl)oxycarbonyl-5-(2-chlorophenyl)-10-methyl-2,4-dihydro-2H,7H-pyrrolo[4,',3':4,5]thieno[3,2-f][1,2,4]triazolo[4,3-a][1,4]diazepine

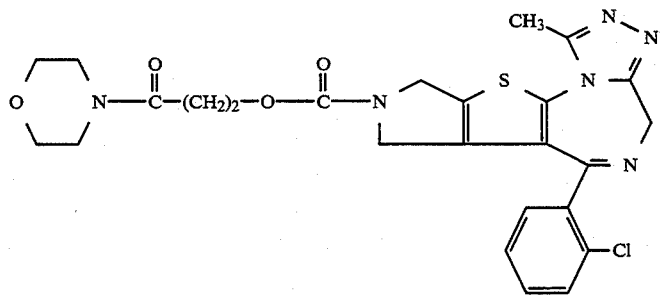

¹H-NMR(CDCl₃)δ: 2.50–2.83(m,2H), 2.72(s,3H), 3.32–3.85(m,10H), 4.34(t,J=7 Hz,1H), 4.40(t,J=7 Hz,1H), 4.52–4.80(m,2H), 4.72–5.10(m,2H), 7.20–7.52(m,4H)
MS m/z: 541

EXAMPLE 112

3-Cyclohexylmethyloxycarbonyl-5-(2-chlorophenyl)-10-methyl-2,4-dihydro-2H,7H-pyrrolo[4',3':4,5]-thieno[3,2-f][1,2,4]triazolo[4,3-a][1,4]diazepine

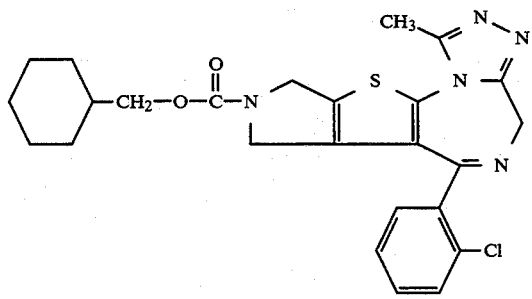

¹H-NMR(CDCl₃)δ: 0.68–1.96(m,11H), 2.75(s,3H), 3.56–4.00(m,4H), 4.65–4.80(m,2H), 4.82–5.18(m,2H), 7.20–7.58(m,4H)
MS m/z: 496

EXAMPLE 113

3-Benzylaminocarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

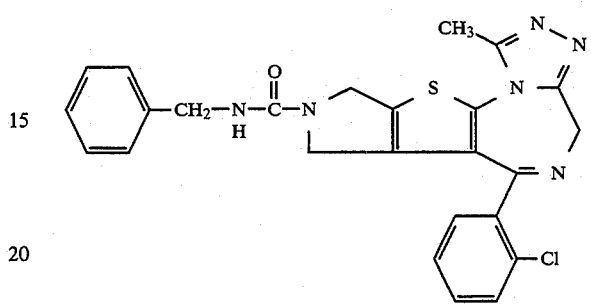

¹H-NMR(CDCl₃)δ: 2.68(s,3H), 3.60–3.94(m,2H), (4.36(d,J=5.4 Hz,2H), 4.50–5.08(m,4H), 7.04–7.50(m,10H)
MS m/z: 489

EXAMPLE 114

3-(n-hexyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

¹H-NMR(CDCl₃)δ: 0.75–1.04(m,3H), 1.10–1.80(m,8H), 2.72(s,3H), 3.54–3.84(m,2H), 4.02(t,J=7 Hz,1H), 4.08(t,J=7 Hz,1H), 4.58–4.80(m,2H), 4.78–5.10(m,2H), 7.20–7.48(m,4H)
MS m/z: 484

EXAMPLE 115

3-Phenetyloxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

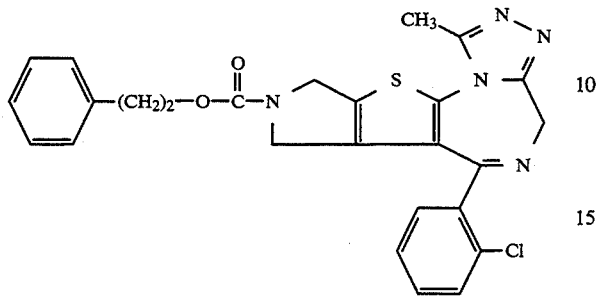

$^1$H-NMR(CDCl$_3$)δ: 2.72(s,3H), 2.86(t,J=7 Hz,1H), 2.94(t,J=7 Hz,1H), 3.55–3.84(m,2H), 4.24(t,J=7 Hz,1H), 4.30(t,J=7 Hz,1H), 4.50–4.75(m,2H), 4.78–5.10(m,2H), 6.98–7.50(m,9H)
MS m/z: 504

EXAMPLE 116

3-(4'-Chlorobenzyl)oxycarbonyl-5-(2-chlorophenyl)-10-methyl-2,4-dihydro-2H,7H-pyrrolo[4',3':4,5]-thieno[3,2-f][1,2,4]triazolo[4,3-a][1,4]diazepine

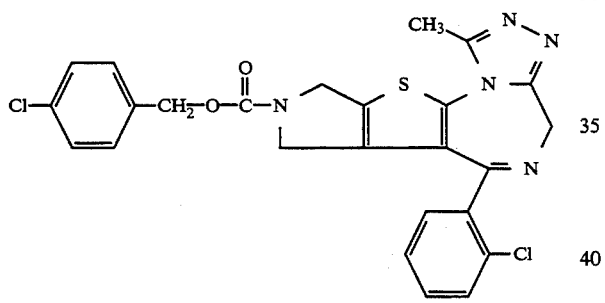

$^1$H-NMR(CDCl$_3$)δ: 2.72(s,3H), 3.60–3.92(m,2H), 4.60–4.80(m,2H), 4.80–5.04(m,2H), 5.08(s,2H), 7.26(ABq,J=6 Hz,4H), 7.10–7.46(m,4H)
MS m/z: 524

EXAMPLE 117

3-(1'-Cyano-1-'-methylethyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

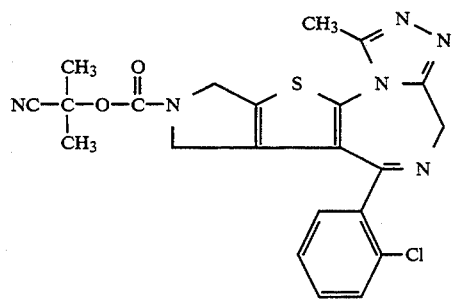

$^1$H-NMR(CDCl$_3$)δ: 1.52(s,3H), 1.80(s,3H), 2.72(s,3H), 3.50–3.86(m,2H), 4.56–4.76(m,2H), 4.78–5.10(m,2H), 7.20–7.45(m,4H)
MS m/z: 467

EXAMPLE 118

3-(3'-Nitrobenzyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

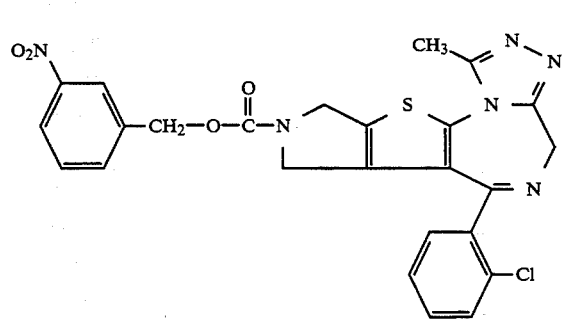

$^1$H-NMR(CDCl$_3$)δ: 2.72(s,3H), 3.66–3.88(m,2H), 4.67–4.82(m,2H), 4.82–5.08(m,2H), 5.18(d,J=2.8 Hz,) 7.20–7.72(m,6H), 7.96–8.24(m,2H)
MS m/z: 535

EXAMPLE 119

3-(4'-Trifluoromethylbenzyl)oxycarbonyl-5-(2-chlorophenyl)-10-methyl-2,4-dihydro-2H,7H-pyrrolo[4',3':4,5]thieno[3,2-f][1,2,4]triazolo[4,3-a][1,4]diazepine

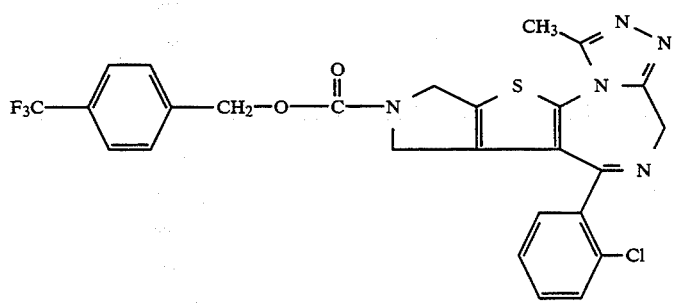

¹H-NMR(CDCl₃)δ: 2.76(s,3H), 3.70–3.92(m,2H), 4.70–4.86(m,2H), 4.88–5.10(m,2H), 5.22(s,2H), 7.25–7.60(m,4H), 7.56(ABq,J=7 Hz,4H)
MS m/z: 558

EXAMPLE 120

3-(2′-Cyanoethyl)aminocarbonyl-5-(2-chlorophenyl)-10-methyl-2,4-dihydro-2H,7H-pyrrolo[4′,3′:4,5]-thieno[3,2-f][1,2,4]triazolo[4,3-a][1,4]diazepine

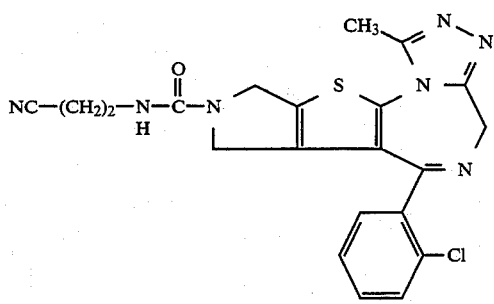

¹H-NMR(CDCl₃)δ: 2.60(t,J=7 Hz,2H), 2.70(s,3H), 3.40(t,J=7 Hz,1H), 3.46(t,J=7 Hz,1H), 4.58–4.80(m,2H), 4.80–5.10(m,2H), 5.30–5.58(m,1H), 7.20–7.50(m,4H)
MS m/z: 452

PREPARATORY EXAMPLE 44

1-Benzyloxycarbonyl-4-(2-hydroxyethyl)piperidine

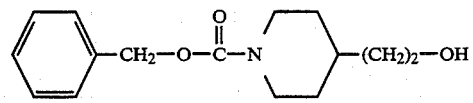

50 g of 4-piperidine ethanol and 49.2 g of sodium hydrogencarbonate were dissolved in 480 ml of water, in which 55.2 ml of benzyloxycarbonyl chloride was gradually dropped under ice-cooling conditions, followed by agitation for 1 hour as it is. The reaction solution was extracted with chloroform and dried with anhydrous magnesium sulfate. The sulfate was filtered off and the solvent was distilled off, after which the resultant residue was subjected to silica gel column chromatography (developing solvent: ethyl acetate:hexane=30:70) to obtain 66.0 g of the captioned compound (yield: 65%).

¹H-NMR(CDCl₃)δ: 0.75–1.85(m,7H), 2.5–3.0(m,2H), 3.4–3.8(m,2H), 3.9–4.3(m,2H), 5.11(s,2H), 7.1–7.4(m,5H)

PREPARATORY EXAMPLE 45

1-Benzyloxycarbonyl-4-(formylmethyl)piperidine

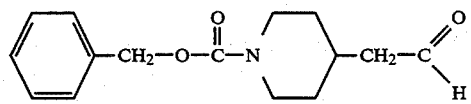

159 g of oxalic acid chloride was dissolved in one liter of dichloromethane, in to which 195.8 g of dimethyl sulfoxide was dropped at −67° C., followed by agitation for 30 minutes. Thereafter, 200 ml of dichloromethane dissolving 66 g of 1-benzyloxycarbonyl-4-(2-hydroxyethyl)piperidine was dropped at −67° C. Subsequently, 380 g of triethylamine was dropped at −67° C., followed by agitation for about 1 hour. After removal of the solvent by distillation, ethyl acetate was added and insoluble matters were removed by filtration, and the resultant filtrate was washed with water and dried with anhydrous magnesium sulfate, followed by filtration and removal of the solvent by distillation. The resultant residue was subjected to silica gel column chromatography (developing solvent: ethyl acetate:hexane=20:80) to obtain 55.0 g of the captioned compound (yield 84%).

¹H-NMR(90 MHz, CDCl₃)δ: 0.8–1.85(m,4H), 1.85–2.45(m,1H), 2.36(dd,J=6.1 Hz,1.8 Hz,2H), 2.5–3.0(m,2H), 3.9–4.35(m,2H), 5.07(s,2H), 7.1–7.5(m,5H), 9.67(t,J=1.8 Hz,1H)

PREPARATORY EXAMPLE 46

2-Amino-5-[4-(1-benzyloxycarbonyl)piperidyl]-3-(2-chlorobenzoyl)thiophene

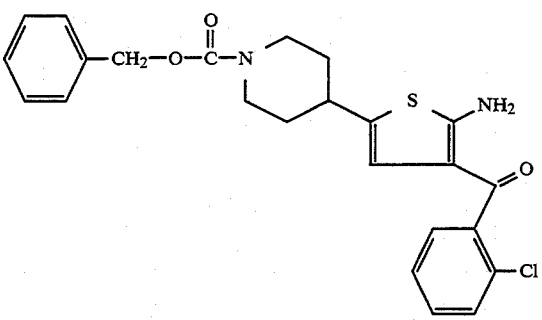

55.0 g of 1-benzyloxycarbonyl-4-(formylmethyl)-piperidine, 6.75 g of sulfur and 38.87 g of 2-chlorocyanoacetophenone were suspended in 250 ml of N,N-dimethylformamide, to which 7.75 g of triethylamine was added at 40° C., followed by agitation for 1.5 hours. After removal of the solvent by distillation, ethyl acetate was added, followed by washing with water and then with a saturated saline solution and drying with anhydrous magnesium sulfate. The reaction solution was filtered and after removal of the solvent by distillation, the resultant residue was subjected to silica gel column chromatography (developing solvent: ethyl acetate:hexane=30:70) to obtain 67.9 g of the captioned compound (yield: 76%).

¹H-NMR(90 MHz, CDCl₃)δ: 1.15–2.1(m,4H), 3.4–4.05(m,3H), 3.95–4.35(m,2H), 5.06(s,2H), 6.04(bs,1H), 6.94(bs,2H), 7.1–7.55(m,9H)

PREPARATORY EXAMPLE 47

2-[4-(1-benzyloxycarbonyl)piperidyl]-5-(bromoacetylamino)-4-(2-chlorobenzoyl)thiophene

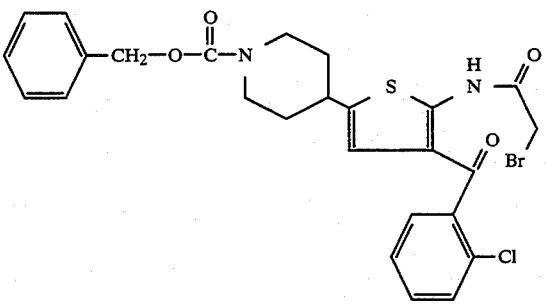

1.5 liters of toluene, 350 ml of water and 27 g of sodium hydrogencarbonate were added to 67.9 g of the compound obtained in Preparatory Example 46, to which was further added 48.61 g of bromoacetic acid bromide at 60° C. After completion of the reaction, ethyl acetate was added, and the resultant organic phase was collected, washed with a saturated saline solution and dried with anhydrous magnesium sulfate. The solution was filtered and the solvent was distilled off to obtain the captioned compound.

¹H-NMR(90 MHz, CDCl₃)δ: 1.1–2.2(m,4H), 2.55–3.05(m,3H), 4.07(s,2H), 4.0–4.45(m,2H), 5.06(s,2H), 6.36(bs,1H), 7.1–7.6(m,9H), 12.47(bs,1H)

PREPARATORY EXAMPLE 48

2-(Aminoacetylamino)-5-[4-(1-benzyloxycarbonyl)-piperidyl]-3-(2-chlorobenzoyl)thiophene

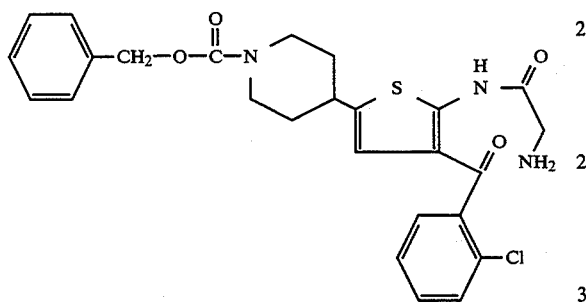

2 liters of ethyl acetate was added to the whole amount of the compound obtained in Preparatory Example 47, after which ammonia gas was passed into the mixture while agitating at room temperature for 3 hours, followed by continuing the agitation for further 12 hours. After passage of nitrogen gas for about 30 minutes, an organic phase was collected under salting-out and the resultant aqueous phase was extracted with chloroform under salting-out. Both organic phases were dried with anhydrous magnesium sulfate. The solution was filtered and the solvent was distilled off to obtain the captioned compound.

¹H-NMR(90 MHz, CDCl₃)δ: 1.1–2.15(m,4H), 2.5–3.05(m,3H), 4.61(bs,2H), 3.9–4.4(m,2H), 5.06(s,2H), 6.32(bs,1H), 7.1–7.6(m,9H)

PREPARATORY EXAMPLE 49

2-[4-(1-benzyloxycarbonyl)piperidyl]-4-(2-chlorophenyl)-thieno[3,2-f][1,4]diazepin-7-one

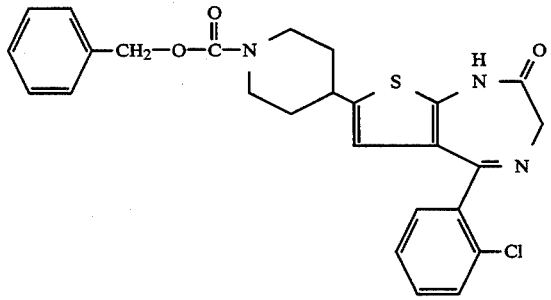

600 ml of benzene, 1.5 liters of pyridine and 9.6 g of acetic acid were added to the whole amount of the compound obtained in Preparatory Example 48, followed by refluxing for 25 hours while removing the water to outside. After removal of the solvent by distillation, the resultant residue was subjected to silica gel column chromatography (developing solvent: ethyl acetate:hexane=60:40) to obtain 61.21 g of the captioned compound (total yield of the three steps: 77%).

¹H-NMR(90 MHz, CDCl₃)δ: 1.0–2.15(m,4H), 2.35–3.0(m,3H), 3.9–4.4(m,2H), 4.43(m,2H), 5.07(s,2H), 6.16(bs,1H), 7.05–7.55(m,9H), 8.93(bs,1H)

PREPARATORY EXAMPLE 50

2-[4-(1-benzyloxycarbonyl)piperidyl]-4-(2-chlorophenyl)-thieno[3,2-f][1,4]diazepin-7-thione

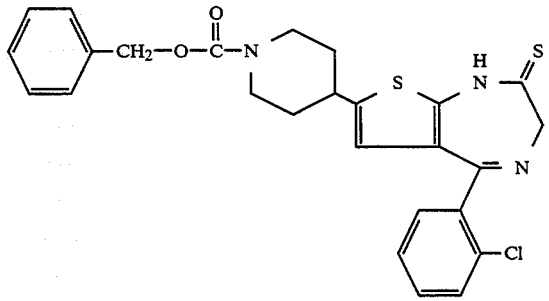

61.21 g of the compound obtained in Preparatory Example 49, 13.53 of sodium hydrogencarbonate and 27.54 g of phosphorous pentasulfide were suspended in 1 liter of 1,2-dimethoxyethane, and agitated at 80° C. for 1.5 hours. The reaction solution was filtered through the Celite membrane and the resultant filter cake was washed with chloroform and methanol (Ca 7:3). The washing was combined with the filtrate. The solvent was distilled off and the residue was subjected to silica gel column chromatography (developing solvent: dichloromethane containing 2–8% of methanol) to obtain 62.6 g of the captioned compound (yield 99%).

¹H-NMR(90 MHz, CDCl₃)δ: 1.15–2.1(m,4H), 2.5–3.1(m,3H), 3.95–4.45(m,2H), 4.83(bs,2H), 5.07(bs,2H), 6.18(bs,1H), 7.0–7.6(m,9H)

PREPARATORY EXAMPLE 51

2-[4-(1-benzyloxycarbonyl)piperidyl]-4-(2-chlorophenyl)-9-methyl-6H-thieno[3,2-f][1,2,4]triazolo[4,3-a][1,4]diazepine

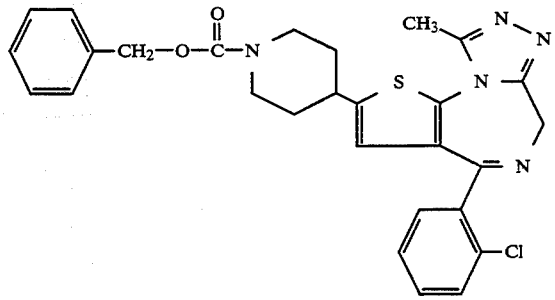

62.6 g of the compound obtained in Preparatory Example 50 was suspended in 3.5 liters of methanol, to which 33.5 g of hydrazine monohydrate was added, followed by agitation at room temperature for 1 hour. After removal of the solvent by distillation, and agitated at 80° C. for 1 hour. After removal of the solvent by distillation, the resultant residue was subjected to silica gel column chromatography (developing solvent: dichloromethane:methanol=98:2) to obtain 21.5 g of the captioned compound (yield 33%).

1H-NMR(90 MHz, CDCl3)δ: 1.2–2.2(m,4H), 2.6–3.05(m,3H), 2.67(s,2H), 4.0–4.4(m,2H), 4.88(bs,2H), 5.07(bs,2H), 6.34(bs,1H), 7.1–7.5(m,9H)

PREPARATORY EXAMPLE 52

4-(2-Chlorophenyl)-9-methyl-2-(4-piperidyl)-6H-thieno[3,2-f][1,2,4]triazolo[4,3-a][1,4]diazepine

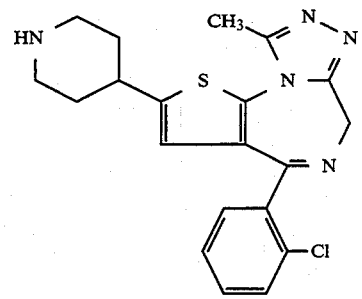

6.65 g of the compound obtained in Preparatory Example 51 was dissolved in 140 ml of dichloromethane, to which 17 ml of trimethylsilyl iodide was added in a stream of nitrogen, followed by agitation in nitrogen for 25 minutes. After cooling, 40 ml of methanol was added and the solvent was distilled off. The resultant residue was subjected to silica gel column chromatography (developing solvent: dichloromethane:methanol:triethylamine=94.5:5.0:0.5) to obtain 4.45 g of the captioned compound (yield 90%).

1H-NMR(90 MHz, CDCl3)δ: 1.1–2.05(m,4H), 2.35–3.2(m,5H), 2.60(s,3H), 4.77(bs,2H), 6.37(bs,1H), 7.2–7.6(m,4H)

MS m/z (Pos. FAB): 398(M+H)−

EXAMPLE 121

4-(2-Chlorophenyl)-9-methyl-2-[4-(1-phenylpropiolyl-piperidyl)]-6H-thieno[3,2-f][1,2,4]triazolo[4,3-a][1,4]diazepine

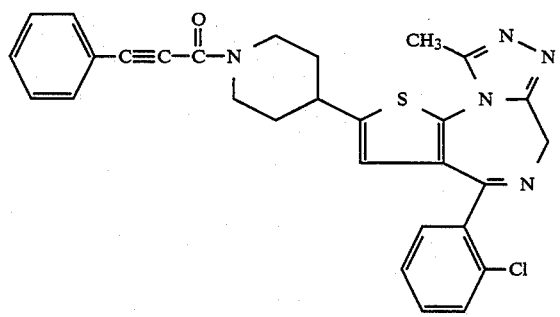

50 mg of phenylpropiolic acid, 110 mg of the piperidine product obtained in Preparatory Example 52 and 50 mg of 1-hydroxybenzotriazole monohydrate were dissolved in 8 ml of N,N-dimethylformamide, to which 70 mg of N,N'-dicycohexylcarbodiimide under ice-cooling conditions, followed by agitation at 4° C. overnight and then at room temperature for 1 hour. After removal of the solvent by distillation, a saturated sodium hydrogencarbonate aqueous solution was added, followed by extraction with chloroform and drying with anhydrous magnesium sulfate. The solution was filtered, from which the solvent was distilled off and the resultant residue was subjected to silica gel column chromatography (developing solvent: dichloromethane:methanol=99:1) to obtain 130 mg of the captioned compound (yield 89%).

1H-NMR(90 MHz, CDCl3)δ: 1.4–2.4(m,4H), 2.55–3.5(m,3H), 2.68(s,3H), 4.35–4.9(m,2H), 4.88(bs,2H), 6.37(bs,1H), 7.05–7.65(m,9H)

MS m/z (Pos. FAB): 526(M+H)−

EXAMPLE 122

4-(2-Chlorophenyl)-2-[4-{1-(3-cyanopropionyl)-piperidyl}]-9-methyl-6H-thieno[3,2-f][1,2,4]triazolo[4,3-a][1,4]diazepine

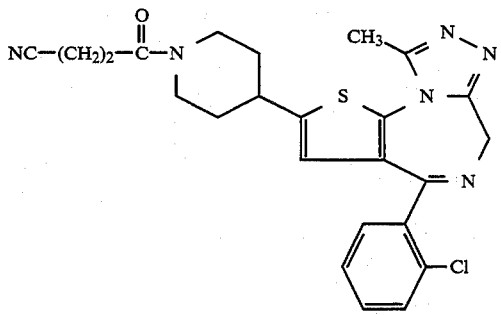

10 ml of methanol, 1 ml of water and 1.34 g of potassium carbonate were added to 1 g of methyl 3-cyanopropionate and agitated at 60° C. for 2 hours. After removal of the solvent by distillation, chloroform was added and insoluble matters were collected by filtration and washed with chloroform. Methanol was added to the crystals and insoluble matters were removed by filtration, followed by removal of the solvent by distillation to obtain 1.31 g of a mixture of potassium 3-cyanopropionate and an inorganic salt.

100 mg of the mixture, 150 mg of the piperidine product obtained in Preparatory Example 52 and 80 mg of 1-hydroxybenzotriazole monohydrate were dissolved in 10 ml of N,N-dimethylformamide, to which 80 mg of N,N'-dicyclohexylcarbodiimide was added under ice-cooling conditions, followed by agitation at 4° C. overnight and at room temperature for 4 hours. After removal of the solvent by distillation, a saturated sodium hydrogencarbonate aqueous solution, followed by extraction with chloroform and drying with anhydrous magnesium sulfate. The solution was filtered and, after removal of the solvent by distillation, the resultant residue was subjected to silica gel column chromatography (developing solvent: dichloromethane:methanol=99:1) to obtain 140 mg of the captioned compound (yield 78%).

1H-NMR(90 MHz, CDCl3)δ: 1.1–2.3(m,4H), 2.67(s,3H), 2.4–3.4(m,3H), 3.5–4.2(m,21), 4.4–5.9(m,1H), 4.88(bs,2H), 6.35(bs,1H), 7.1–7.5(m,4H)

MS m/z (Pos. FAB): 479(M+H)−

EXAMPLE 123

4-(2-Chlorophenyl)-9-methyl-2-[4-(1-morpholinoacetyl-piperidyl)]-6H-thieno[3,2-f][1,2,4]triazolo[4,3-a][1,4]diazepine

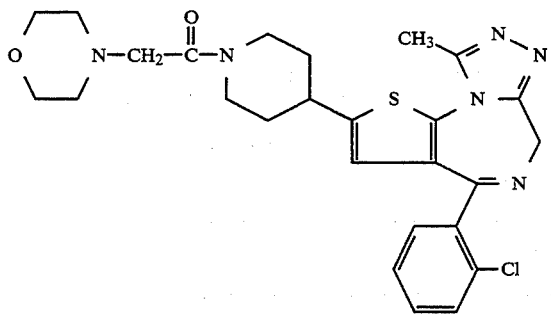

150 mg of the piperidine product obtained in Preparatory Example 52 and 150 mg of triethylamine were dissolved in 4 ml of N,N-dimethylformamide, which was dropped in 4 ml of N,N-dimethylformamide dissolving 60 mg of chloroacetyl chloride at −60° C. After completion of the reaction, a saturated sodium hydrogencarbonate aqueous solution, followed by extraction with chloroform and drying with anhydrous magnesium sulfate. The solution was filtered, from which chloroform alone was distilled off, to which 40 mg of morpholine and 100 mg of potassium carbonate were added, followed by agitation at 60° C. for 1.5 hours. After removal of the solvent by distillation, water was added, followed by extraction with chloroform and drying with anhydrous magnesium sulfate. The extract was filtered and the solvent was distilled off, after which the resultant residue was subjected to silica gel column chromatography (developing solvent: dichloromethane:methanol=98:2) to obtain 130 mg of the captioned compound.

$^1$H-NMR(90 MHz, CDCl$_3$)δ: 1.2–2.25(m,4H), 2.3–2.65(m,4H), 2.68(s,3H), 2.65–3.4(m,5H), 3.5–3.8(m,4H), 3.95–4.36(m,1H), 4.36–4.9(m,1H), 4.89(s,2H), 6.35(bs,1H), 7.1–7.5(m,4H)

MS m/z (Pos. FAB): 525(M+H)$^-$

EXAMPLE 124

4-(2-Chlorophenyl)-9-methyl-2-[4-{1-(4-pentinoyl)-piperidyl}]-6H-thieno[3,2-f][1,2,4triazolo[4,3-a][1,4]diazepine

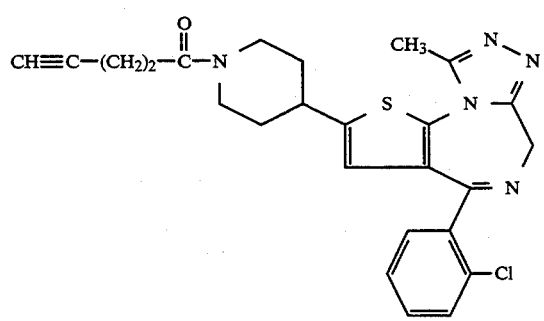

40 mg of 4-pentinic acid, 150 mg of the piperidine product obtained in Preparatory Example 52 and 60 mg of 1-hydroxybenzotriazole monohydrate were dissolved in 10 ml of N,N-dimethylformamide, to which 80 mg of N,N'-dicyclohexylcarbodiimide was added under ice-cooling conditions, followed by agitation at 4° C. overnight and at room temperature for 6 hours. After removal of the solvent by distillation, a saturated sodium hydrogencarbonate aqueous solution was added, followed by extraction with chloroform and drying with anhydrous magnesium sulfate. This was filtered and after removal of the solvent by distillation, the resultant residue was subjected to silica gel column chromatography (developing solvent: dichloromethane:methanol=99:1) to obtain 140 mg of the captioned compound (yield 78%).

$^1$H-NMR(90 MHz, CDCl$_3$)δ: 1.3–2.3(m,5H), 2.3–2.7(m,4H), 2.5–3.4(m,3H), 2.67(s,3H), 3.65–4.15(m,1H), 4.4–5.0(m,1H), 4.88(bs,2H), 6.35(bs,1H), 7.05–7.6(m,4H)

MS m/z (Pos. FAB): 478(M+H)$^+$

EXAMPLE 125

2-[4-{1-(4-Bromophenylacetyl)piperidyl}]-4-(2-chlorophenyl)-9-methyl-6H-thieno-[3,2-f][1,2,4]triazolo[4,3-a][1,4]diazepine

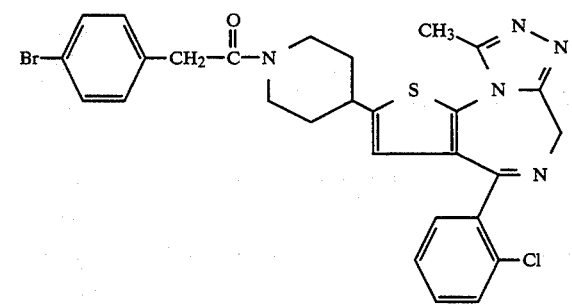

Example 121 was repeated using 4-bromophenyl acetic acid.

$^1$H-NMR(90 MHz, CDCl$_3$)δ: 1.15–2.2(m,4H), 2.49–3.3(m,5H), 2.87(s,3H), 3.55–4.1(m,1H), 4.45–5.0(m,1H), 4.88(bs,2H), 6.34(bs,1H), 6.6–7.11(m,4H), 7.11–7.6(m,4H)

MS m/z (Pos. FAB): 596[(M+H)$^-$, Cl=35, Br=81]

EXAMPLE 126

4-(2-Chlorophenyl)-2-[4-(1-cyanoacetylpiperidyl)]-9-methyl-6H-thieno-[3,2-f][1,2,4]triazolo[4,3-a][1,4]diazepine

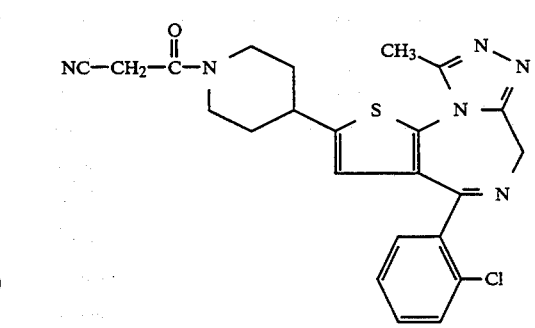

Example 121 was repeated using 4-cyanoacetic acid.

$^1$H-NMR(90 MHz, CDCl$_3$)δ: 1.4–2.4(m,4H), 2.45–3.55(m,3H), 2.67(s,3H), 3.47(s,2H), 3.55–4.0(m,1H), 4.4–4.9(m,1H), 4.87(bs,2H), 6.37(bs,1H), 7.1–7.5(m,4H)

MS m/z (Pos. FAB): 465(M+H)$^+$

EXAMPLE 127

4-(2-Chlorophenyl)-9-methyl-2-[4-[1-{4-(2-thienyl)propionyl}piperidyl]]-6H-thieno-[3,2-f][1,2,4triazolo[4,3-a][1,4]diazepine

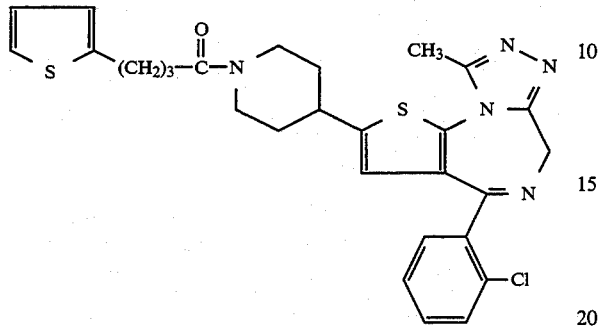

Example 121 was repeated using 4-(2-thienyl)-butanoic acid.

¹H-NMR(90 MHz, CDCl₃)δ: 1.1–2.2(m,6H), 2.4–3.32(m,3H), 2.67(s,3H), 3.32–4.45(m,4H), 4.45–5.05(m,2H), 4.88(bs,2H), 6.32(bs,1H), 6.95–7.6(m,7H)

MS m/z (Pos. FAB): 550(M+H)+

EXAMPLE 128

4-(2-Chlorophenyl)-2-[4-(1-cyclopropanecarbonyl-piperidyl)]-9-methyl-thieno[3,2-f][1,2,4]triazolo[4,3-a][1,4]diazepine

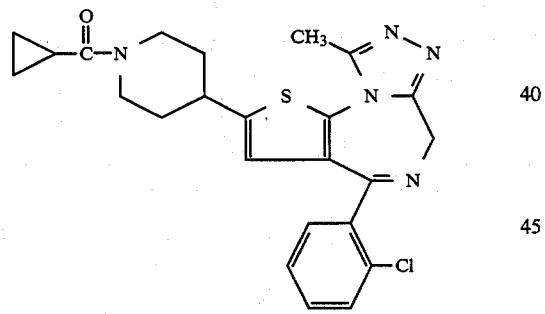

700 mg of the piperidine product obtained in Preparatory Example 52 and 900 mg of triethylamine were dissolved in 5 ml of N,N-dimethylformamide, in which 10 ml of an N,N-dimethylformamide solution dissolving 650 mg of 3-bromopropionyl chloride was dropped at −60° C. After removal of the solvent by distillation, a saturated sodium hydrogencarbonate aqueous solution was added, followed by extraction with chloroform and drying with anhydrous magnesium sulfate. This was filtered and after removal of the solvent by distillation, the resultant residue was subjected to silica gel column chromatography (developing solvent: dichloromethane:methanol=99:1) to obtain 400 mg of the captioned compound (yield 49%).

¹H-NMR(90 MHz, CDCl₃)δ: 0.6–1.15(m,4H), 1.2–2.25(m,5H), 2.4–3.5(m,3H), 2.68(s,3H), 3.7–5.0(m,2H), 4.89(bs,2H), 6.36(bs,1H), 7.1–7.5(m,4H)

EXAMPLE 129

4-(2-Chlorophenyl)-9-methyl-2-[4-(1-pentanoyl)-piperidyl]-6H-thieno[3,2-f][1,2,4]triazolo[4,3-a][1,4]diazepine

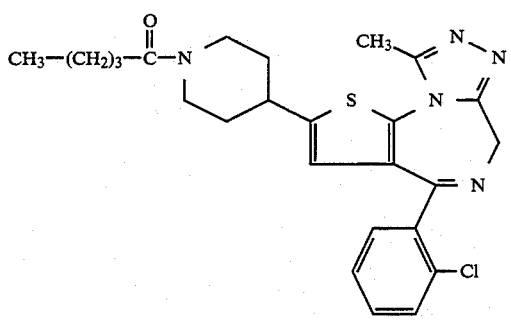

Prepared in the same manner as in Example 121 using valeric acid chloride.

¹H-NMR(90 MHz, CDCl₃)δ: 0.91(t,J=6.5 Hz,3H), 1.1–2.3(m,3H), 2.31(t,J=7.2 Hz,2H), 2.67(s,3H), 2.5–3.4(m,3H), 3.7–4.2(m,1H), 4.45–5.0(m,1H), 4.88(bs,2H), 6.35(bs,2H), 7.1–7.5(m,4H)

MS m/z(Pos. FAB): 482(M+H)+

EXAMPLE 130

4-(2-Chlorophenyl)-9-methyl-2-[4-(1-octanoyl)-piperidyl]-6H-thieno[3,2-f][1,2,4]triazolo[4,3-a][1,4]diazepine

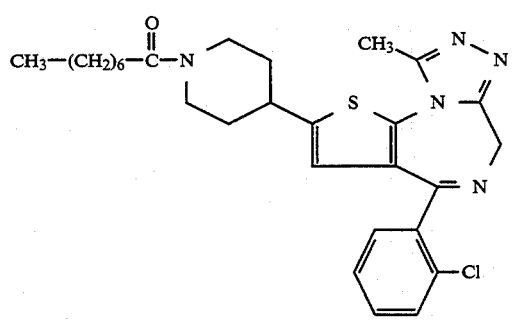

Prepared in the same manner as in Example 121 using octanoyl chloride.

¹H-NMR(90 MHz, CDCl₃)δ: 0.7–1.1(m,3H), 1.1–2.5(m,14H), 2.31(t,J=7.5 Hz,2H), 2.68(s,3H), 2.5–3.35(m,3H), 3.7–4.15(m,1H), 4.45–5.0(m,1H), 4.88(bs,2H), 6.35(bs,2H), 7.1–7.5(m,4H)

MS m/z(Pos. FAB): 524(M+H)+

EXAMPLE 131

4-(2-Chlorophenyl)-2-[4-(1-methoxyacetylpiperidyl)]-9-methyl-6H-thieno[3,2-f][1,2,4]triazolo[4,3-a][1,4]diazepine

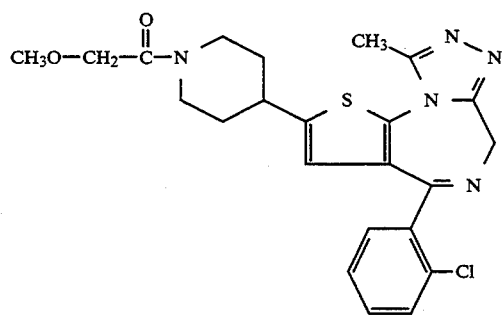

Prepared in the same manner as in Example 121 using methoxyacetic acid chloride.

$^1$H-NMR(90 MHz, CDCl$_3$)δ: 1.4–2.3(m,4H), 2.4–3.2(m,3H), 2.68(s,3H), 3.39(s,3 H), 3.7–4.2(m,1H), 4.06(s,2H), 4.4–4.9(m,1H), 4.89(m,1H), 6.36(bs,1H), 7.1–7.55(m,4H)

MS m/z(Pos. FAB): 470(M+H)$^+$

PREPARATORY EXAMPLE 53

2-Morpholinoethylphenyl carbonate

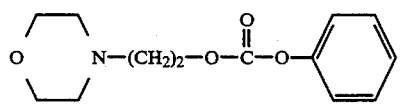

2 g of 4-(2-hydroxyethyl)morpholine and 3.6 g of pyridine were dissolved in 40 ml of dichloroethane, in which 5.97 g of phenyl chloroformate was dropped under ice-cooling conditions, followed by agitation for about 30 minutes as it is. A saturated sodium hydrogencarbonate aqueous solution was added and the resultant organic phase was collected. The aqueous phase was extracted with chloroform and the extract and the organic phase were combined, followed by washing with a saturated saline solution and drying with anhydrous magnesium sulfate. This was filtered and the solvent was distilled off, and the resultant residue was subjected to silica gel column chromatography (developing solvent: ethyl acetate:hexane=30:70) to obtain 3.39 g of the captioned compound (yield 89%).

$^1$H-NMR(90 MHz, CDCl$_3$)δ: 2.35–2.7(m,4H), 2.69(t,J=6.1 Hz,2H), 3.55–3.85(m,4H), 4.34(m,4H), 4.34(t,J=6.1 Hz,2H), 6.95–7.5(m,4H)

EXAMPLE 132

4-(2-Chlorophenyl)-9-methyl-2-[4-(2-morpholinoethyloxycarbonyl)piperidyl]-6H-thieno[3,2-f][1,2,4]triazolo[4,3-a][1,4]diazepine

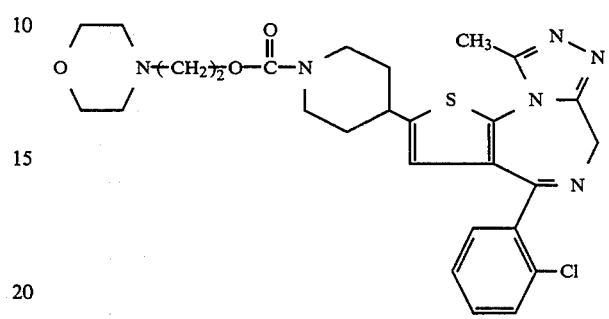

170 mg of the piperidine product obtained in Preparatory Example 52 and 290 mg of 2-morpholinoethylphenyl carbonate were dissolved in 6 ml of chloroform and evaporated to dryness while agitating at 80° C. Chloroform was added and the evaporation to dryness was repeated two or three times, thereby completing the reaction. The resultant product was subjected to silica gel column chromatography (developing solvent: dichloromethane:methanol=97:3) and dichloromethane was added to the resultant fraction, from which insoluble matters were removed by decantation. After removal of the dichloromethane by distillation, a small amount of dichloromethane was added, from which insoluble matters were again removed, followed by removal of the dichloromethane by distillation to obtain 170 mg of the captioned compound.

$^1$H-NMR(90 MHz, CDCl$_3$)δ: 1.2–2.2(m,4H), 2.25–3.15(m,7H), 2.54(t,J=6.1 Hz,2H), 2.68(s,3H), 3.55–3.55(m,4H), 3.95–4.45(m,2H), 4.18(5,J=6.1 Hz,2H), 4.89(bs,2H), 6.36(bs,1H), 7.1–7.55(m,4H)

MS m/z(Pos. FAB): 555(M+H)$^+$

PREPARATORY EXAMPLE 54

2-Cyanoethylphenyl carbonate

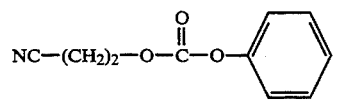

Prepared in the same manner as in Preparatory Example 53.

$^1$H-NMR(90 MHz, CDCl$_3$)δ: 4.83(s,2H), 6.9–7.5(m,5H)

EXAMPLE 133

4-(2-Chlorophenyl)-2-[4-{1-(2-cyanoethyloxycarbonyl)piperidyl}]-9-methyl-6H-thieno[3,2-f][1,2,4]triazolo[4,3-a][1,4]diazepine

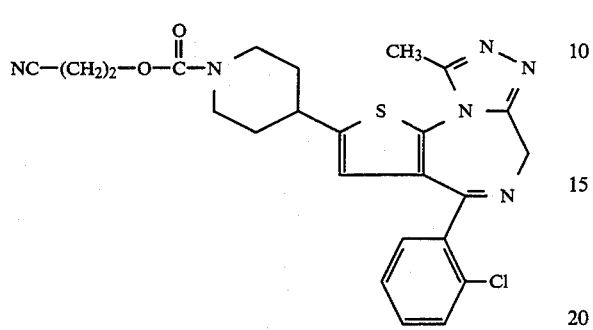

150 mg of the piperidine product obtained in Preparatory Example 52 and 180 mg of 2-cyanoethylphenyl carbonate were dissolved in 5 ml of chloroform, followed by evaporation to dryness while agitating at an ambient temperature of 110° C. The operation wherein chloroform was again added and heated to dryness while agitating was repeated until the reaction was completed. The resultant product was subjected to silica gel column chromatography (developing solvent: dichloromethane) to obtain 90 mg of the captioned compound.

$^1$H-NMR(90 MHz, CDCl$_3$)δ: 1.3–2.2(m,4H), 2.5–3.2(m,3H), 2.68(s,3H), 2.69(t,J=6.1 Hz,2H), 3.9–4.45(m,2H), 4.25(t,J=6.1 Hz,2H), 4.88(bs,2H), 6.36(bs,1H), 7.1–7.6(m,4H)

MS m/z(Pos. FAB): 495(M+H)+

EXAMPLE 134

4-(2-Chlorophenyl)-2-[4-(1-cyanomethyloxycarbonylpiperidyl]-9-methyl-6H-thieno[3,2-f][1,2,4]triazolo[4,3-a][1,4]diazepine

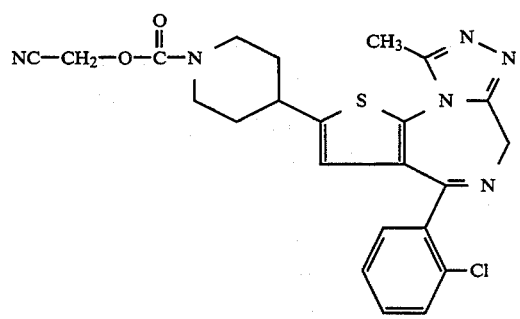

$^1$H-NMR(90 MHz, CDCl$_3$)δ: 1.1–2.4(m,4H), 2.6–3.3(m,3H), 2.68(s,3H), 3.9–4.5(m,2H), 4.89(bs,2H), 6.36(bs,1H), 7.1–7.5(m,4H)

MS m/z(Pos. FAB): 481(M+H)+

EXAMPLE 135

4-(2-Chlorophenyl)-2-[4-{1-(3-cyanopropyloxycarbonyl)piperidyl}]-9-methyl-6H-thieno[3,2-f][1,2,4]triazolo[4,3-a][1,4]diazepine

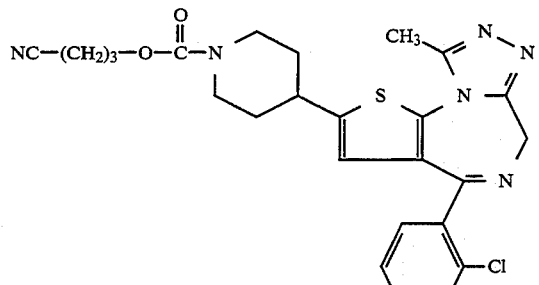

$^1$H-NMR(90 MHz, CDCl$_3$)δ: 1.1–2.3(m,6H), 2.42(t,J=6.8 Hz,2H), 2.68(s,3H), 2.6–3.3(m,3H), 3.85–4.45(m,2H), 4.16(t,J=5.8 Hz,2H), 4.48(bs,2H), 6.35(bs,1H), 7.1–7.55(m,4H)

MS m/z(Pos. FAB): 509(M+H)+

EXAMPLE 136

2-[4-{1-(3-Butinyloxycarbonylpiperidyl}]-4-(2-chlorophenyl)-9-methyl-6H-thieno[3,2-f][1,2,4]triazolo[4,3-a][1,4]diazepine

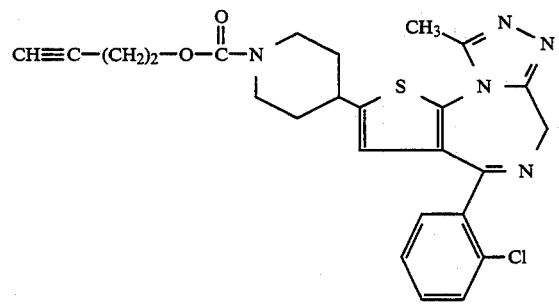

$^1$H-NMR(90 MHz, CDCl$_3$)δ: 1.2–2.2(m,4H), 1.96(t,J=2.9 Hz,1H), 2.3–3.15(m,3H), 2.51(td,J=6.8 Hz,2.9 Hz,2H), 2.68(s,3H), 3.9–4.5(m,2H), 4.15(t,J=6.8 Hz,2H), 4.89(bs,2H), 6.35(bs,1H), 7.1–7.6(m,4H)

MS m/z(Pos. FAB): 494(M+H)+

EXAMPLE 137

2-[4-(1-Butoxycarbonyl)piperidyl]-4-(2-chlorophenyl)-9-methyl-6H-thieno[3,2-f][1,2,4]triazolo[4,3-a][1,4]diazepine

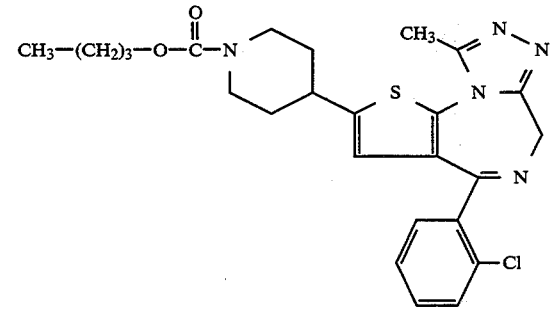

¹H-NMR(90 MHz, CDCl₃)δ: 0.92(t,J=6.1 Hz,3H), 1.1–2.2(m,8H), 2.68(s,3H), 2.5–3.15(m,3H), 3.9–4.4(t,J=6.5 Hz,2H), 4.88(bs,2H), 6.35(bs,1H), 7.1–7.55(m,4H)

MS m/z(Pos. FAB): 498(M+H)⁺

PREPARATORY EXAMPLE 55

2-Bromoethyl t-butyldimethylsilyl ether

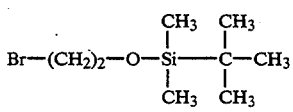

2 g of ethylene bromohydrin and 2.4 g of imidazole were dissolved in 40 ml of N,N-dimethylformamide, to which 2.65 g of t-butyldimethylsilyl chloride were added at room temperature. After completion of the reaction, benzene was added, followed by washing with water and a sodium hydrogencarbonate aqueous solution and drying with anhydrous magnesium sulfate. This was filtered and the solvent was distilled off, thereby obtaining 3.60 g of the captioned compound (yield 94%).

¹H-NMR(90 MHz, CDCl₃)δ: 0.13(s,6H), 0.94(s,9H), 3.38(t,J=6.5 Hz,2H), 3.88(t,J=6.5 Hz,2H)

PREPARATORY EXAMPLE 56

1-(2-Hydroxyethyl)imidazole

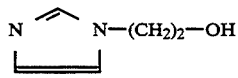

3.56 g of 2-bromoethyl t-butyldimethylsilyl ether and 1.97 g of imidazole were dissolved in 70 ml of N,N-dimethylformamide, to which 4 g of potassium carbonate were added, followed by agitation at 90° C. for 2 hours and 40 minutes. After removal of the solvent by distillation, ethyl acetate was added, followed by washing with water and drying with anhydrous magnesium sulfate. This was filtered and, after removal of the solvent by distillation, m the resultant residue was dissolved in tetrahydrofuran, to which 12.6 ml of tetrabutylammonium fluoride (1M tetrahydrofuran solution), followed by agitation at room temperature. After completion of the reaction, the solvent was distilled of and the resultant residue was subjected to silica gel column chromatography (developing solvent: dichloromethane) to obtain 0.59 g of the caption compound (yield 35%).

¹H-NMR(90 MHz, CDCl₃)δ: 3.28(bs,1H), 3.6–4.2(m,4H), 6.84(bs,1H), 7.28(bs,1H)

PREPARATORY EXAMPLE 57

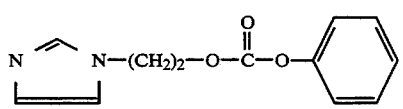

Prepared from the compound of Preparatory Example 56 in the same manner as in Preparatory Example 53.

EXAMPLE 138

4-(2-Chlorophenyl)-2-[4-[1-{2-(1-imidazoyl)ethyloxycarbonyl}piperidyl]]-9-methyl-6H-thieno[3,2-f][1,2,4]triazolo[4,3-a][1,4]diazepine

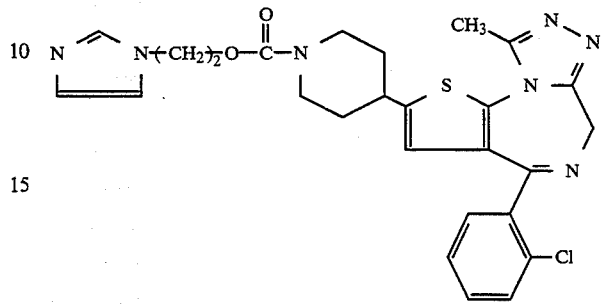

¹H-NMR(90 MHz, CDCl₃)δ: 1.2–2.2(m,4H), 2.4–3.1(m,3H), 2.68(s,3H), 3.9–4.5(m,6H), 4.87(bs,2H), 6.36(bs,1H), 7.1–7.6(m,4H), 7.42(bs,1H)

MS m/z(Pos. FAB): 536(M+H)⁺

EXAMPLE 139

4-(2-Chlorophenyl)-9-methyl-2-[4-{1-tetrahydropyran-4-yl-oxycarbonyl)piperidyl}]-6H-thieno[3,2-f][1,2,4]triazolo[4,3-a][1,4]diazepine

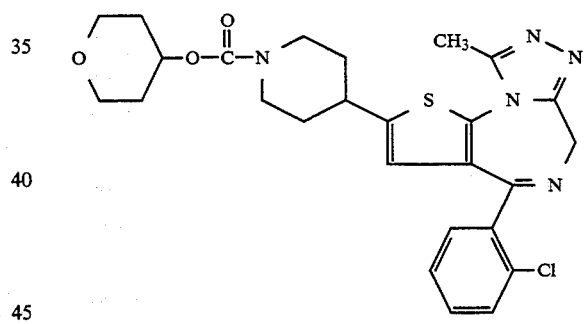

¹H-NMR(90 MHz, CDCl₃)δ: 1.0–2.2(m,8H), 2.5–3.2(m,3H), 2.68(s,3H), 3.25–3.67(m,2H), 3.67–4.0(m,2H), 4.0–4.39(m,2H), 4.5–5.05(m,1H), 4.88(s,2H), 6.35(bs,1H), 7.05–7.55(m,4H)

MS m/z(Pos. FAB): 526(M+H)⁺

PREPARATORY EXAMPLE 58

Phenyl 3-phenylpropylcarbonate

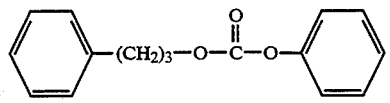

Prepared in the same manner as in Preparatory Example 53 at a yield of 70%.

¹H-NMR(90 MHz, CDCl₃)δ: 1.8–2.25(m,2H), 2.74(dd,J=9.0 Hz,6.5 Hz, 2H), 4.23(d,J=6.5 Hz,2H), 6.95–7.55(m,10H)

EXAMPLE 140

4-(2-Chlorophenyl)-9-methyl-2-[{1-(3-phenylpropyloxycarbonyl)piperidyl}]-6H-thieno[3,2-f][1,2,4]triazolo[4,3-a][1,4]diazepine

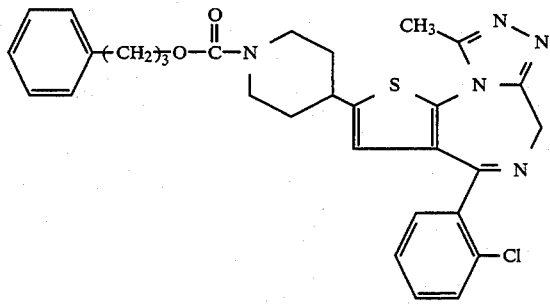

¹H-NMR(90 MHz, CDCl₃)δ: 1.0–2.2(m,6H), 2.4–3.2(m,5H), 2.68(s,3H), 3.8–4.4(m,2H), 4.07(t,J=6.5 Hz,2H), 4.87(bs,2H), 6.36(bs,1H), 6.7–7.6(m,9H)
MS m/z(Pos. FAB): 560(M+H)+

EXAMPLE 141

4-(2-Chlorophenyl)-9-methyl-2-[4-{1-(2-morpholinoethylaminocarbonyl)piperidyl}]-6H-thieno[3,2-f][1,2,4]triazolo[4,3-a][1,4]diazepine

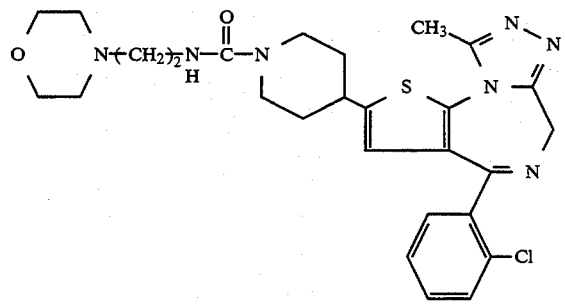

170 mg of the piperidine product obtained in Preparatory Example 52 and 210 mg of 4-[2-(phenyloxycarbonylamino)ethyl]morpholine were dissolved in 4 ml of chloroform and evaporated to dryness while agitating at 80° C. Chloroform was added and the evaporation-to-dryness operation was repeated twice, thereby comprising the reaction. This was subjected to silica gel column chromatography (developing solvent: dichloromethane:methanol=95:5). A small amount of dichloromethane was added to the resultant fraction and insoluble matters were removed by decantation. After removal of the dichloromethane by distillation, a small amount of dichloromethane was again added, followed by removal of insoluble matters by filtration. The dichloromethane was distilled off to obtain 160 mg of the captioned compound.

¹H-NMR(90 MHz, CDCl₃)δ: 1.0–2.25(m,4H), 2.25—3.1(m,9H), 2.67(s,3H), 3.1–3.5(m,2H), 3.5–3.85(m,4H), 3.85–4.2(m,3H), 4.88(bs,2H), 6.35(bs,1H), 7.1–7.6(m,4H)
MS m/z(Pos. FAB): 554(M+H)+

PREPARATORY EXAMPLE 59

4-(Phenyloxycarbonyl)morpholine

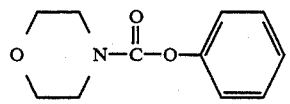

Prepared in the same manner as in Preparatory Example 53 and purified by silica gel column chromatography (developing solvent: ethyl acetate:hexane=5:95).
¹H-NMR(90 MHz, CDCl₃)δ: 3.4–3.9(m,8H), 6.9–7.5(m,5H)

EXAMPLE 142

4-(2-Chlorophenyl)-9-methyl-2-[4-(1-morpholinocarbonylpiperidyl)]-6H-thieno[3,2-f][1,2,4]triazolo[4,3-a][1,4]diazepine

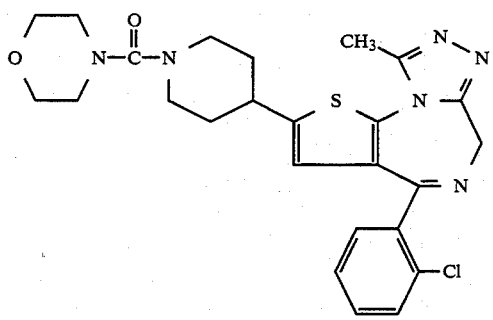

5 ml of chloroform was added to 180 mg of the piperidine obtained in Preparatory Example 52 and 250 mg of 4-(phenyloxycarbonyl)morpholine, followed by agitation at an ambient temperature of 130° C. for 12 hours while evaporating to dryness. This was subjected to silica gel column chromatography (developing solvent: dichloromethane) to obtain 38.8 mg of the captioned compound.

¹H-NMR(90 MHz, CDCl₃)δ: 1.2–2.4(m,4H), 2.6–3.2(m,3H), 2.68(s,3H), 3.0–3.45(m,4H), 3.45–3.95(m,6H), 4.88(bs,2H), 6.36(bs,1H), 7.05–7.5(m,4H)

PREPARATORY EXAMPLE 60

2-Ethoxyethyl p-toluenesulfonic acid

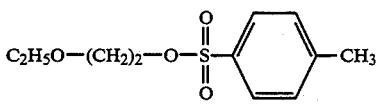

2 g of 2-ethoxyethanol were dissolved in 40 ml of pyridine, to which 5.66 g of p-toluenesulfonyl chloride was added under ice-cooling conditions, followed by raising to room temperature. Ethyl acetate was added, followed by washing with water and a saturated sodium hydrogencarbonate aqueous solution and drying with anhydrous magnesium sulfate. This was filtered and, after removal of the solvent by distillation, the resultant residue was subjected to silica gel column chromatography (developing solvent: ethyl acetate:hexane=5:95) to obtain 3.69 g of the captioned compound (yield 56%).

¹H-NMR(90 MHz, CDCl₃)δ: 1.12(t,J=7.2 Hz,3H), 2.42(s,3H), 3.42(q,J=7.2 Hz,2H), 3.4–3.7(m,2H), 4.0–4.2(m,2H), 7.26(bd,J=8.3 Hz,2H), 7.73(bd,J=8.3 Hz,2H)

EXAMPLE 143

4-(2-Chlorophenyl)-2-[4-{1-(2-ethoxyethyl)piperidyl}]-9-methyl-6H-thieno[3,2-f][1,2,4]triazolo[4,3-a][1,4]diazepine

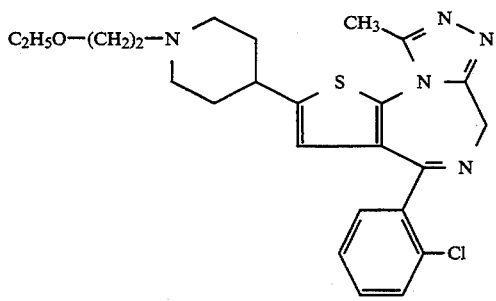

150 mg of the piperidine product obtained in Preparatory Example 52 and 140 mg of 2-ethoxyethyl p-toluenesulfonate were dissolved in 5 ml of N,N-dimethylformamide, to which 100 mg of potassium carbonate, followed by agitation at 90° C. for 2 hours. After removal of the solvent by distillation, water was added, followed by extraction with chloroform and drying with anhydrous magnesium sulfate. This was filtered and, after removal of the solvent by distillation, the resultant residue was subjected to silica gel column chromatography (developing solvent: dichloromethane:methanol=98:2) to obtain 120 mg of the captioned compound (yield 68%)

¹H-NMR(90 MHz, CDCl₃)δ: 1.20(t,J=7.2 Hz,3H), 1.5–2.4(m,6H), 2.4–3.0(m,1H), 2.64(t,J=6.1 Hz,2H), 2.71(s,2H), 2.8–3.25(m,2H), 3.51(q,J=7.2 Hz,2H), 3.59(t,J=6.1 Hz,2H), 4.95(bs,2H), 6.44(bs,1H), 7.2–7.6(m,4H)

MS m/z(Pos. FAB): 470(M+H)+

PREPARATORY EXAMPLE 61

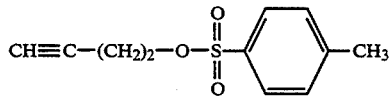

Prepared in the same manner as in Preparatory Example 60 at a yield of 70%.

¹H-NMR(90 MHz, CDCl₃)δ: 1.95(t,J=2.9 Hz,1H), 2.27(s,3H), 2.53(td,J=7.2 Hz,2.9 Hz,2H), 4.06(t,J=7.2 Hz,2H), 7.25(bd,J=8.3 Hz,2H), 7.73(bd,J=8.3 Hz,2H)

EXAMPLE 144

2-[4-{1-(3-Butynyl)piperidyl}]-4-(2-chlorophenyl)-9-methyl-6H-thieno[3,2-f][1,2,4-triazolo[4,3-a][1,4]diazepine

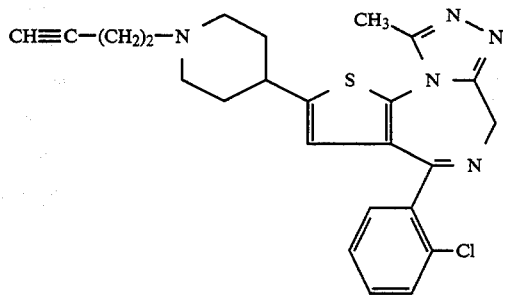

¹H-NMR(90 MHz, CDCl₃)δ: 1.4–3.0(m,11H), 1.97(t,J=2.5 Hz,1H), 2.68(s,3H), 2.8–3.2(m,2H), 4.88(bs,2H), 6.35(bs,1H), 7.1–7.5(m,4H)

MS m/z(Pos. FAB): 450(M+H)+

EXAMPLE 145

4-(2-chlorophenyl)-4-[1-(dimethylaminosulfonyl)-piperidyl]-9-methyl-6H-thieno[3,2-f][1,2,4]triazolo[4,3-a][1,4]diazepine

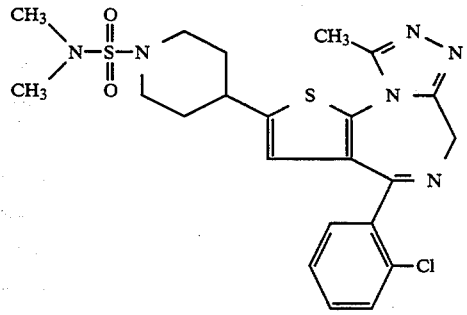

100 mg of the piperidine product obtained in preparatory Example 52 and 80 mg of triethylamine were dissolved in 3 ml of N,N-dimethylformamide, which was dropped in 4 ml of N,N-dimethylformamide dissolving 50 mg of dimethylsulfamoyl chloride at −60° C. Because the starting materials were left in large amounts, triethylamine and dimethylsulfamoyl chloride were added at room temperature until the starting materials disappeared. After removal of the solvent by distillation, a saturated sodium hydrogencarbonate aqueous solution was added, followed by extraction with chloroform and drying with anhydrous magnesium sulfate. This was filtered and subjected to silica gel column chromatography (developing solvent: dichloromethane:methanol=99:1) to obtain 90 mg of the captioned compound (yield 71%).

¹H-NMR(90 MHz, CDCl₃)δ: 1.5–2.2(m,4H), 2.5–3.1(m,3H), 2.68(s,3H), 2.80(s,6H), 3.55–3.9(m,2H), 4.89(bs,2H), 6.32(bs,1H), 7.1–7.5(m,4H)

MS m/z(Pos. FAB): 505(M+H)+

EXAMPLE 146

4-(2-chlorophenyl)-9-methyl-2-[4-{1-(2-thiophensulfonyl)piperidyl}]-6H-thieno[3,2-f][1,2,4]triazolo[4,3-a][1,4]diazepine

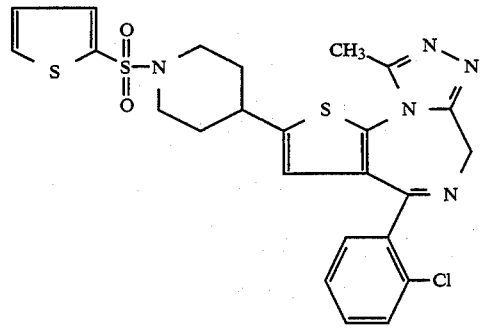

Prepared in the same manner as in Example 121 using 2-thiophensulfonyl chloride.

$^1$H-NMR(90 MHz, CDCl$_3$)δ: 1.5–2.3(m,4H), 2.3–2.95(m,1H), 2.44(td,J=12.2 Hz,3.6 Hz,2H), 2.67(s,3H), 3.65–4.15(m,2H), 4.88(bs,2H), 6.33(bs,1H), 6.8–7.7(m,7H)

What is claimed is:

1. A triazolo-1,4-di-azepine compound or a pharmacologically acceptable salt thereof, having the formula:

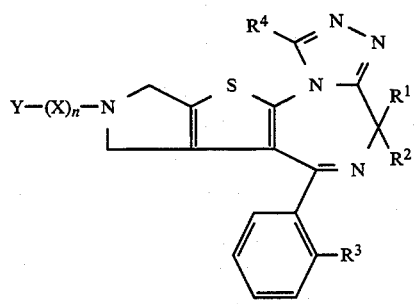

wherein R$^1$ and R$^2$ are the same or different and represent a hydrogen atom or a lower alkyl group, R$^3$ represents a hydrogen atom or a halogen atom, R$^4$ represents a hydrogen atom or a lower alkyl group, X represents (a) a group of the formula,

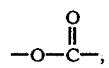

(b) a group of the formula,

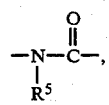

wherein R$^5$ represents a hydrogen atom or a lower alkyl group, (c) a group of the formula,

(d) a group of the formula,

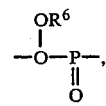

wherein R$^6$ represents a lower alkyl group, or (e) a group of the formula,

n is an integer of 0 or 1,
and Y represents (1) a cycloalkyl group,
(2) a cycloalkylalkyl,
(3) an alkynyl group,
(4) a group of the formula,

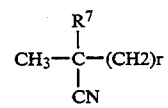

in which R$^7$ is hydrogen or methyl and r is zero, 1 or 2, (5) a group of the formula, NC—(CH$_2$)$_p$—, wherein p is an integer of from 1 to 6, (6) a group of the formula A—(CH$_2$)$_q$— wherein A represents a group selected from a pyridyl group, a pyranyl group and a morpholino group and q is an integer of from 0 to 6, (7) an alkynyl group having from 1 to 6 carbon atoms wherein a phenyl group or a cycloalkyl group is joined to any carbon atom, (8) a group of the formula,

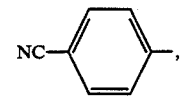

(9) a group of the formula,

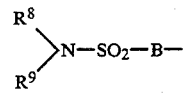

wherein R$^8$ and R$^9$ are the same or different and represent a hydrogen atom, a lower alkyl group, a pyridylmethyl group or a cycloalkyl group or R$^8$ and R$^9$ may be joined along with a nitrogen atom to form a ring selected from the group consisting of

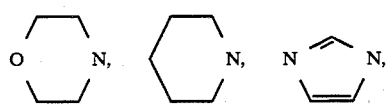

-continued

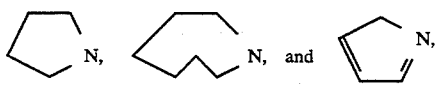

and B represents a phenylene group or a lower alkylene group having from 1 to 3 carbon atoms,

(10) a group of the formula,

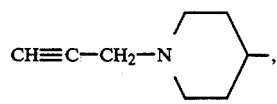

(11) a group of the formula,

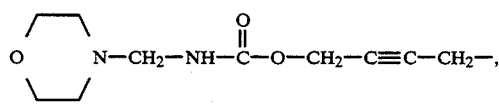

(12) a group of the formula,

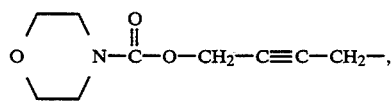

(15) a lower alkyl group,
(16) a cycloalkylalkenyl group,
(17)

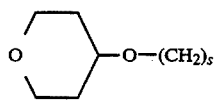

in which s is 1 or 2,
(18)

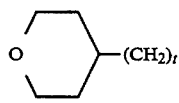

in which t is 1 or 2,
(19)

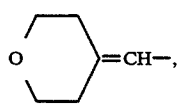

(20) an arylalkyl,
(21) an arylalkenyl,
(22)

in which $R^{10}$ is hydrogen or phenyl, $R^{11}$ is hydrogen or a lower alkyl, E is an alkenylene and u is zero or 1 with the proviso that $R^{10}$ and $R^{11}$ are not both hydrogen at the same time, (23)

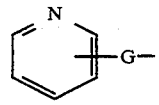

in which G is an alkenylene or —J—$(CH_2)_k$—, wherein J is oxygen or sulfur, and k is zero, 1 or 2, provided that when X is a group of the formula

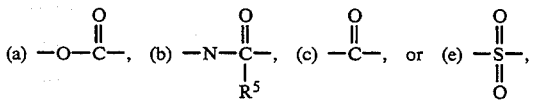

Y is a group selected from (1) to (12) and (16) to (23), when X is a group of the formula (d), Y is a lower alkyl of group (15), and when n is zero, Y is an alkynyl group of (3).

2. The compound as claimed in claim 1 wherein said arylalkenyl of group (21) is selected from the group consisting of

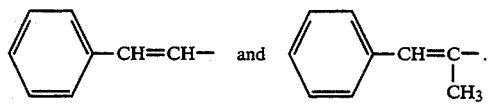

3. The compound as claimed in claim 1, wherein said alkynyl group of group (7) is

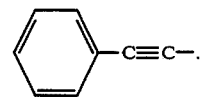

4. The compound as claimed in claim 1, wherein $R^1$ is hydrogen and $R^2$ is methyl.

5. The compound as claimed in claim 1, wherein Y is a cycloalkyl having 3 to 7 carbon atoms.

6. The compound as claimed in claim 5, wherein Y is cyclopropyl.

7. The compound as claimed in claim 1, wherein Y is one of groups (2), (3), (4), (6), or (16).

8. The compound as claimed in claim 1 in which $R^3$ is chlorine, $R^1$ is hydrogen, $R^4$ is methyl, n is 1, and Y—X— and $R^2$ are defined, respectively, with one of the following combinations:

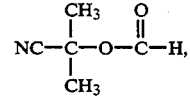

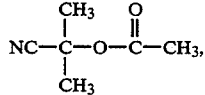

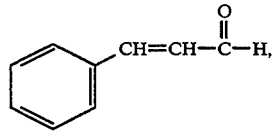

-continued

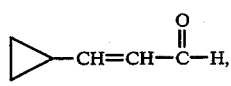

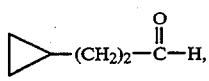

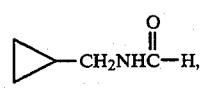

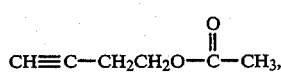

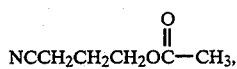

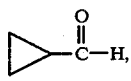

-continued

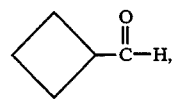

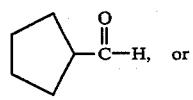

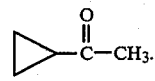

9. A pharmaceutical composition which comprises a pharmacologically effective amount of the compound or the salt thereof, defined in claim 1, and a pharmacologically acceptable carrier.

10. A method for treating a disease against which anti-PAF activity is effective, which comprises administering a pharmacologically effective amount of the compound or the salt thereof as defined in claim 1.

11. A method as claimed in claim 10, in which the disease is an allergic disease.

12. A method as claimed in claim 10, in which the disease is asthma.

* * * * *